(12) United States Patent
Emery et al.

(10) Patent No.: US 6,339,070 B1
(45) Date of Patent: Jan. 15, 2002

(54) GENE CONSTRUCT ENCODING A HETEROLOGOUS PRODRUG-ACTIVATING ENZYME AND A CELL TARGETING MOIETY

(75) Inventors: Stephen Charles Emery; David Charles Blakey, both of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/423,439

(22) PCT Filed: May 5, 1998

(86) PCT No.: PCT/GB98/01294

§ 371 Date: Nov. 9, 1999

§ 102(e) Date: Nov. 9, 1999

(87) PCT Pub. No.: WO98/51787

PCT Pub. Date: Nov. 19, 1998

(30) Foreign Application Priority Data

May 10, 1997 (GB) .............................. 9709421

(51) Int. Cl.[7] ........................ A61F 48/00; C12N 15/00; C12N 15/63; C12N 15/88

(52) U.S. Cl. .................... 514/44; 424/93.2; 435/320.1; 435/325; 435/455; 435/458

(58) Field of Search ................. 514/44; 536/23.1, 536/24.1; 435/320.1, 328, 456, 69.7; 424/93.21, 134.1, 178.1, 94.1, 277.1

(56) References Cited

U.S. PATENT DOCUMENTS 5,464,758 A * 11/1995 Gossen et al. ............. 435/69.1
5,589,466 A   12/1996 Feigner et al. ............. 514/144
5,645,835 A *  7/1997 Fell ........................ 424/134.1
5,683,694 A * 11/1997 Bagshawa et al. ....... 424/178.1

FOREIGN PATENT DOCUMENTS

| EP | 0 415 731 A2 | 3/1991 |
| WO | WO 91/02805 | 3/1991 |
| WO | WO 92/17210 | 10/1992 |
| WO | WO 93/19163 | 9/1993 |
| WO | WO 94/06920 | 3/1994 |
| WO | WO 94/10323 | 5/1994 |
| WO | WO 95/12678 | 5/1995 |
| WO | WO 95/14100 | 5/1995 |
| WO | WO 96/03151 | 2/1996 |
| WO | WO 96/16179 | 5/1996 |
| WO | WO 96/103151 | * 8/1996 |
| WO | WO 97/07769 | * 3/1997 |
| WO | WO 97/19180 | 5/1997 |
| WO | WO 97/26918 | 7/1997 |
| WO | WO 97/42329 | * 11/1997 |
| WO | WO 98/55607 | 12/1998 |

OTHER PUBLICATIONS

F. Herrmann. Cancer gene therapy: principles, problems, and perspectives. J. Mol Med. vol. 73: 157–163, 1995.*

W. French Anderson. Human gene therapy. Nature. vol. 392, 25–30, 1998.*

(List continued on next page.)

*Primary Examiner*—Dave T. Nguyen
(74) *Attorney, Agent, or Firm*—Pillsbury Winthrop LLP

(57) ABSTRACT

The invention provides a gene construct encoding a cell targeting moiety and a heterologous prodrug activating enzyme for use as a medicament in a mammalian host wherein the gene construct is capable of expressing the cell targeting moiety and enzyme as a conjugate within a target cell in the mammalian host and wherein the conjugate is directed to leave the cell thereafter for selective localisation at a cell surface antigen recognised by the cell targeting moiety.

34 Claims, 3 Drawing Sheets

| SS | A5B7 Fd | | CPG2/R6 |

L

OTHER PUBLICATIONS

Blakey et al. Anti-tumor effects of an antibody-carboxypeptidase G2 conjugate in combination with phenol mustard prodrugs. British J. Cancer. vol. 72. 1083–1088, 1995.*

R. G. Crystal. Transfer of genes to humans: early lessons and obstacles to success. Science. vol. 270, 404–410, 1995.*

Springer et al., Gene-directed enzyme prodrug therapy (GDEPT): choice of prodrugs, Advanced Drug Delivery Reviews, vol. 22, 1996, pp. 351–364.

Glick, Molecular Biotechnology, ASM Press, Chapter 5, pp. 113–118, 1994.*

Rodrigues et al., Cancer Res., 55, 63–70, 1995.*

* cited by examiner

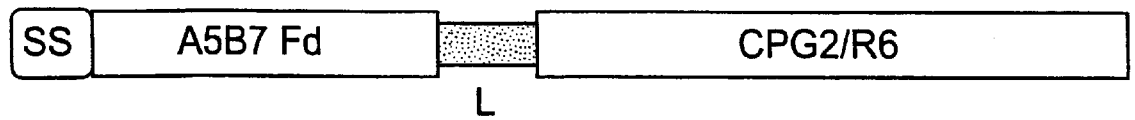
Fig. 1
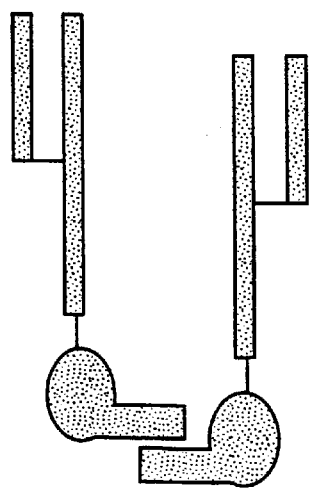 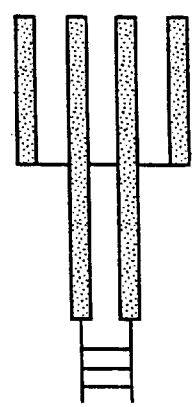
Fig. 2a Fig. 2b

SEQUENCE LISTING (1) GENERAL INFORMATION:

(iii) NUMBER OF SEQUENCES: 60

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 1:

GGGAATTCCT CGAGGAGCTC C                                         21

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 2:

CCGGGGAGCT CCTCGAGGAA TTCCCGC                                   27

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 3:

CAGAAGCGCG ACAACGTG                                             18

(2) INFORMATION FOR SEQ ID NO: 4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

CGAGGCCTTG CCGGTGATCT GGACCTGCAC GTAGGCGAT                      39

(2) INFORMATION FOR SEQ ID NO: 5:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

GGGGATGATG TTCGAGACCT GGCCGGCCTT GGCGATGGTC CACTGGAAGC GCAGGTTCTT    60

CGC                                                             63

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

CTTGCCGGCG CCCAGATC                                                      18

(2) INFORMATION FOR SEQ ID NO: 7:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 7:

GTCTCGAACA TCATCCCC                                                      18

(2) INFORMATION FOR SEQ ID NO: 8:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 8:

ATCACCGGCA AGGCCTCG                                                      18

(2) INFORMATION FOR SEQ ID NO: 9:

(i) SEQUENCE CHARACTERISTICS:
             (A) LENGTH: 1236 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 9:

ATGGATTTTC AAGTGCAGAT TTTCAGCTTC CTGCTAATCA GTGCTTCAGT CATAATGTCC        60

CGCGGGCAGA AGCGCGACAA CGTGCTGTTC CAGGCAGCTA CCGACGAGCA GCCGGCCGTG       120

ATCAAGACGC TGGAGAAGCT GGTCAACATC GAGACCGGCA CCGGTGACGC CGAGGGCATC       180

GCCGCTGCGG GCAACTTCCT CGAGGCCGAG CTCAAGAACC TCGGCTTCAC GGTCACGCGA       240

AGCAAGTCGG CCGGCCTGGT GGTGGGCGAC AACATCGTGG CAAGATCAA GGGCCGCGGC       300

GGCAAGAACC TGCTGCTGAT GTCGCACATG GACACCGTCT ACCTCAAGGG CATTCTCGCG       360

AAGGCCCCGT TCCGCGTCGA AGGCGACAAG GCCTACGGCC CGGGCATCGC CGACGACAAG       420

GGCGGCAACG CGGTCATCCT GCACACGCTC AAGCTGCTGA AGGAATACGG CGTGCGCGAC       480

TACGGCACCA TCACCGTGCT GTTCAACACC GACGAGGAAA AGGGTTCCTT CGGCTCGCGC       540

GACCTGATCC AGGAAGAAGC CAAGCTGGCC GACTACGTGC TCTCCTTCGA GCCCACCAGC       600

GCAGGCGACG AAAAACTCTC GCTGGGCACC TCGGGCATCG CCTACGTGCA GGTCCAGATC       660

ACCGGCAAGG CCTCGCATGC CGGCGCCGCG CCCGAGCTGG GCGTGAACGC GCTGGTCGAG       720

GCTTCCGACC TCGTGCTGCG CACGATGAAC ATCGACGACA AGGCGAAGAA CCTGCGCTTC       780

CAGTGGACCA TCGCCAAGGC CGGCCAGGTC TCGAACATCA TCCCCGCCAG CGCCACGCTG       840

AACGCCGACG TGCGCTACGC GCGCAACGAG GACTTCGACG CCGCCATGAA GACGCTGGAA       900

-continued

```
GAGCGCGCGC AGCAGAAGAA GCTGCCCGAG GCCGACGTGA AGGTGATCGT CACGCGCGGC      960

CGCCCGGCCT TCAATGCCGG CGAAGGCGGC AAGAAGCTGG TCGACAAGGC GGTGGCCTAC     1020

TACAAGGAAG CCGGCGGCAC GCTGGGCGTG AAGAGCGCA CCGGCGGCGG CACCGACGCG     1080

GCCTACGCCG CGCTCTCAGG CAAGCCAGTG ATCGAGAGCC TGGGCCTGCC GGGCTTCGGC     1140

TACCACAGCG ACAAGGCCGA GTACGTGGAC ATCAGCGCGA TTCCGCGCCG CCTGTACATG     1200

GCTGCGCGCC TGATCATGGA TCTGGGCGCC GGCAAG                               1236
```

(2) INFORMATION FOR SEQ ID NO: 10:

(i) SEQUENCE CHARACTERISTICS:
        (A) LENGTH: 412 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Met Asp Phe Gln Val Gln Ile Phe Ser Phe Leu Leu Ile Ser Ala Ser
1               5                  10                  15

Val Ile Met Ser Arg Gly Gln Lys Arg Asp Asn Val Leu Phe Gln Ala
            20                  25                  30

Ala Thr Asp Glu Gln Pro Ala Val Ile Lys Thr Leu Glu Lys Leu Val
        35                  40                  45

Asn Ile Glu Thr Gly Thr Gly Asp Ala Glu Gly Ile Ala Ala Ala Gly
    50                  55                  60

Asn Phe Leu Glu Ala Glu Leu Lys Asn Leu Gly Phe Thr Val Thr Arg
65                  70                  75                  80

Ser Lys Ser Ala Gly Leu Val Val Gly Asp Asn Ile Val Gly Lys Ile
                85                  90                  95

Lys Gly Arg Gly Gly Lys Asn Leu Leu Leu Met Ser His Met Asp Thr
            100                 105                 110

Val Tyr Leu Lys Gly Ile Leu Ala Lys Ala Pro Phe Arg Val Glu Gly
        115                 120                 125

Asp Lys Ala Tyr Gly Pro Gly Ile Ala Asp Asp Lys Gly Gly Asn Ala
    130                 135                 140

Val Ile Leu His Thr Leu Lys Leu Leu Lys Glu Tyr Gly Val Arg Asp
145                 150                 155                 160

Tyr Gly Thr Ile Thr Val Leu Phe Asn Thr Asp Glu Glu Lys Gly Ser
                165                 170                 175

Phe Gly Ser Arg Asp Leu Ile Gln Glu Glu Ala Lys Leu Ala Asp Tyr
            180                 185                 190

Val Leu Ser Phe Glu Pro Thr Ser Ala Gly Asp Glu Lys Leu Ser Leu
        195                 200                 205

Gly Thr Ser Gly Ile Ala Tyr Val Gln Val Gln Ile Thr Gly Lys Ala
    210                 215                 220

Ser His Ala Gly Ala Ala Pro Glu Leu Gly Val Asn Ala Leu Val Glu
225                 230                 235                 240

Ala Ser Asp Leu Val Leu Arg Thr Met Asn Ile Asp Asp Lys Ala Lys
                245                 250                 255

Asn Leu Arg Phe Gln Trp Thr Ile Ala Lys Ala Gly Gln Val Ser Asn
            260                 265                 270

Ile Ile Pro Ala Ser Ala Thr Leu Asn Ala Asp Val Arg Tyr Ala Arg
        275                 280                 285
```

```
Asn Glu Asp Phe Asp Ala Ala Met Lys Thr Leu Glu Glu Arg Ala Gln
            290                 295                 300

Gln Lys Lys Leu Pro Glu Ala Asp Val Lys Val Ile Val Thr Arg Gly
305                 310                 315                 320

Arg Pro Ala Phe Asn Ala Gly Glu Gly Gly Lys Lys Leu Val Asp Lys
                325                 330                 335

Ala Val Ala Tyr Tyr Lys Glu Ala Gly Gly Thr Leu Gly Val Glu Glu
            340                 345                 350

Arg Thr Gly Gly Gly Thr Asp Ala Ala Tyr Ala Ala Leu Ser Gly Lys
        355                 360                 365

Pro Val Ile Glu Ser Leu Gly Leu Pro Gly Phe Gly Tyr His Ser Asp
            370                 375                 380

Lys Ala Glu Tyr Val Asp Ile Ser Ala Ile Pro Arg Arg Leu Tyr Met
385                 390                 395                 400

Ala Ala Arg Leu Ile Met Asp Leu Gly Ala Gly Lys
                405                 410
```

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

```
CCACTCTCAC AGTGAGCTCG G                                         21
```

(2) INFORMATION FOR SEQ ID NO: 12:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

```
ACCGCTACCG CCACCACCAG AGCCACCACC GCCAACTGTC TTGTCCACCT TGGTG    55
```

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

```
ACCCCCTCTA GAGTCGAC                                             18
```

(2) INFORMATION FOR SEQ ID NO: 14:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

| | | | | |
|---|---|---|---|---|
| TCTGGTGGTG | GCGGTAGCGG | TGGCGGGGGT | TCCCAGAAGC | GCGACAACGT GCTG | 54 |

(2) INFORMATION FOR SEQ ID NO: 15:

(i) SEQUENCE CHARACTERISTICS:
        (A) LENGTH: 1929 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

| | | | | | |
|---|---|---|---|---|---|
| ATGGAGTTGT | GGCTGAACTG | GATTTTCCTT | GTAACACTTT | TAAATGGTAT | CCAGTGTGAG | 60 |
| GTGAAGCTGG | TGGAGTCTGG | AGGAGGCTTG | GTACAGCCTG | GGGGTTCTCT | GAGACTCTCC | 120 |
| TGTGCAACTT | CTGGGTTCAC | CTTCACTGAT | TACTACATGA | ACTGGGTCCG | CCAGCCTCCA | 180 |
| GGAAAGGCAC | TTGAGTGGTT | GGGTTTTATT | GGAAACAAAG | CTAATGGTTA | CACAACAGAG | 240 |
| TACAGTGCAT | CTGTGAAGGG | TCGGTTCACC | ATCTCCAGAG | ATAAATCCCA | AAGCATCCTC | 300 |
| TATCTTCAAA | TGAACACCCT | GAGAGCTGAG | GACAGTGCCA | CTTATTACTG | TACAAGAGAT | 360 |
| AGGGGGCTAC | GGTTCTACTT | TGACTACTGG | GGCCAAGGCA | CCACTCTCAC | AGTGAGCTCG | 420 |
| GCTAGCACCA | AGGGACCATC | GGTCTTCCCC | CTGGCCCCCT | GCTCCAGGAG | CACCTCCGAG | 480 |
| AGCACAGCCG | CCCTGGGCTG | CCTGGTCAAG | GACTACTTCC | CCGAACCGGT | GACGGTGTCG | 540 |
| TGGAACTCAG | GCGCTCTGAC | CAGCGGCGTG | CACACCTTCC | CGGCTGTCCT | ACAGTCCTCA | 600 |
| GGACTCTACT | CCCTCAGCAG | CGTCGTGACG | GTGCCCTCCA | GCAACTTCGG | CACCCAGACC | 660 |
| TACACCTGCA | ACGTAGATCA | CAAGCCCAGC | AACACCAAGG | TGGACAAGAC | AGTTGGCGGT | 720 |
| GGTGGCTCTG | GTGGTGGCGG | TAGCGGTGGC | GGGGGTTCCC | AGAAGCGCGA | CAACGTGCTG | 780 |
| TTCCAGGCAG | CTACCGACGA | GCAGCCGGCC | GTGATCAAGA | CGCTGGAGAA | GCTGGTCAAC | 840 |
| ATCGAGACCG | GCACCGGTGA | CGCCGAGGGC | ATCGCCGCTG | CGGGCAACTT | CCTCGAGGCC | 900 |
| GAGCTCAAGA | ACCTCGGCTT | CACGGTCACG | CGAAGCAAGT | CGGCCGGCCT | GGTGGTGGGC | 960 |
| GACAACATCG | TGGGCAAGAT | CAAGGGCCGC | GGCGGCAAGA | ACCTGCTGCT | GATGTCGCAC | 1020 |
| ATGGACACCG | TCTACCTCAA | GGGCATTCTC | GCGAAGGCCC | CGTTCCGCGT | CGAAGGCGAC | 1080 |
| AAGGCCTACG | GCCCGGGCAT | CGCCGACGAC | AAGGGCGGCA | ACGCGGTCAT | CCTGCACACG | 1140 |
| CTCAAGCTGC | TGAAGGAATA | CGGCGTGCGC | GACTACGGCA | CCATCACCGT | GCTGTTCAAC | 1200 |
| ACCGACGAGG | AAAAGGGTTC | CTTCGGCTCG | CGCGACCTGA | TCCAGGAAGA | AGCCAAGCTG | 1260 |
| GCCGACTACG | TGCTCTCCTT | CGAGCCCACC | AGCGCAGGCG | ACGAAAAACT | CTCGCTGGGC | 1320 |
| ACCTCGGGCA | TCGCCTACGT | GCAGGTCCAG | ATCACCGGCA | AGGCCTCGCA | TGCCGGCGCC | 1380 |
| GCGCCCGAGC | TGGGCGTGAA | CGCGCTGGTC | GAGGCTTCCG | ACCTCGTGCT | GCGCACGATG | 1440 |
| AACATCGACG | ACAAGGCGAA | GAACCTGCGC | TTCCAGTGGA | CCATCGCCAA | GGCCGGCCAG | 1500 |
| GTCTCGAACA | TCATCCCCGC | CAGCGCCACG | CTGAACGCCG | ACGTGCGCTA | CGCGCGCAAC | 1560 |
| GAGGACTTCG | ACGCCGCCAT | GAAGACGCTG | GAAGAGCGCG | CGCAGCAGAA | GAAGCTGCCC | 1620 |
| GAGGCCGACG | TGAAGGTGAT | CGTCACGCGC | GGCCGCCCGG | CCTTCAATGC | CGGCGAAGGC | 1680 |
| GGCAAGAAGC | TGGTCGACAA | GGCGGTGGCC | TACTACAAGG | AAGCCGGCGG | CACGCTGGGC | 1740 |
| GTGGAAGAGC | GCACCGGCGG | CGGCACCGAC | GCGGCCTACG | CCGCGCTCTC | AGGCAAGCCA | 1800 |
| GTGATCGAGA | GCCTGGGCCT | GCCGGGCTTC | GGCTACCACA | GCGACAAGGC | CGAGTACGTG | 1860 |

GACATCAGCG CGATTCCGCG CCGCCTGTAC ATGGCTGCGC GCCTGATCAT GGATCTGGGC    1920

GCCGGCAAG    1929

(2) INFORMATION FOR SEQ ID NO: 16:

(i) SEQUENCE CHARACTERISTICS:
        (A) LENGTH: 643 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

```
Met Glu Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Asn Trp Val Arg Gln Pro Pro Gly Lys Ala Leu
    50                  55                  60

Glu Trp Leu Gly Phe Ile Gly Asn Lys Ala Asn Gly Tyr Thr Thr Glu
65                  70                  75                  80

Tyr Ser Ala Ser Val Lys Gly Arg Phe Thr Ile Ser Arg Asp Lys Ser
                85                  90                  95

Gln Ser Ile Leu Tyr Leu Gln Met Asn Thr Leu Arg Ala Glu Asp Ser
            100                 105                 110

Ala Thr Tyr Tyr Cys Thr Arg Asp Arg Gly Leu Arg Phe Tyr Phe Asp
        115                 120                 125

Tyr Trp Gly Gln Gly Thr Thr Leu Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Gly Gly
225                 230                 235                 240

Gly Gly Ser Gly Gly Gly Gly Ser Gly Gly Gly Gly Ser Gln Lys Arg
                245                 250                 255

Asp Asn Val Leu Phe Gln Ala Ala Thr Asp Glu Gln Pro Ala Val Ile
            260                 265                 270

Lys Thr Leu Glu Lys Leu Val Asn Ile Glu Thr Gly Thr Gly Asp Ala
        275                 280                 285

Glu Gly Ile Ala Ala Ala Gly Asn Phe Leu Glu Ala Glu Leu Lys Asn
    290                 295                 300

Leu Gly Phe Thr Val Thr Arg Ser Lys Ser Ala Gly Leu Val Val Gly
305                 310                 315                 320

Asp Asn Ile Val Gly Lys Ile Lys Gly Arg Gly Gly Lys Asn Leu Leu
                325                 330                 335
```

```
Leu Met Ser His Met Asp Thr Val Tyr Leu Lys Gly Ile Leu Ala Lys
            340                 345                 350

Ala Pro Phe Arg Val Glu Gly Asp Lys Ala Tyr Gly Pro Gly Ile Ala
            355                 360                 365

Asp Asp Lys Gly Gly Asn Ala Val Ile Leu His Thr Leu Lys Leu Leu
            370                 375                 380

Lys Glu Tyr Gly Val Arg Asp Tyr Gly Thr Ile Thr Val Leu Phe Asn
385                 390                 395                 400

Thr Asp Glu Glu Lys Gly Ser Phe Gly Ser Arg Asp Leu Ile Gln Glu
                405                 410                 415

Glu Ala Lys Leu Ala Asp Tyr Val Leu Ser Phe Glu Pro Thr Ser Ala
            420                 425                 430

Gly Asp Glu Lys Leu Ser Leu Gly Thr Ser Gly Ile Ala Tyr Val Gln
            435                 440                 445

Val Gln Ile Thr Gly Lys Ala Ser His Ala Gly Ala Ala Pro Glu Leu
            450                 455                 460

Gly Val Asn Ala Leu Val Glu Ala Ser Asp Leu Val Leu Arg Thr Met
465                 470                 475                 480

Asn Ile Asp Asp Lys Ala Lys Asn Leu Arg Phe Gln Trp Thr Ile Ala
                485                 490                 495

Lys Ala Gly Gln Val Ser Asn Ile Ile Pro Ala Ser Ala Thr Leu Asn
                500                 505                 510

Ala Asp Val Arg Tyr Ala Arg Asn Glu Asp Phe Asp Ala Ala Met Lys
            515                 520                 525

Thr Leu Glu Glu Arg Ala Gln Gln Lys Lys Leu Pro Glu Ala Asp Val
            530                 535                 540

Lys Val Ile Val Thr Arg Gly Arg Pro Ala Phe Asn Ala Gly Glu Gly
545                 550                 555                 560

Gly Lys Lys Leu Val Asp Lys Ala Val Ala Tyr Tyr Lys Glu Ala Gly
                565                 570                 575

Gly Thr Leu Gly Val Glu Glu Arg Thr Gly Gly Thr Asp Ala Ala
            580                 585                 590

Tyr Ala Ala Leu Ser Gly Lys Pro Val Ile Glu Ser Leu Gly Leu Pro
            595                 600                 605

Gly Phe Gly Tyr His Ser Asp Lys Ala Glu Tyr Val Asp Ile Ser Ala
            610                 615                 620

Ile Pro Arg Arg Leu Tyr Met Ala Ala Arg Leu Ile Met Asp Leu Gly
625                 630                 635                 640

Ala Gly Lys (2) INFORMATION FOR SEQ ID NO: 17:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

ATGGATTTTC AAGTGCAGAT TTTCAGCTTC CTGCTAATCA GTGCTTCAGT CATAATGTCC      60

AGAGGACAAA CTGTTCTCTC CCAGTCTCCA GCAATCCTGT CTGCATCTCC AGGGGAGAAG     120

GTCACAATGA CTTGCAGGGC CAGCTCAAGT GTAACTTACA TTCACTGGTA CCAGCAGAAG     180

CCAGGTTCCT CCCCCAAATC CTGGATTTAT GCCACATCCA ACCTGGCTTC TGGAGTCCCT     240
```

```
GCTCGCTTCA GTGGCAGTGG GTCTGGGACC TCTTACTCTC TCACAATCAG CAGAGTGGAG    300

GCTGAAGATG CTGCCACTTA TTACTGCCAA CATTGGAGTA GTAAACCACC GACGTTCGGT    360

GGAGGCACCA AGCTCGAGAT CAAACGGACT GTGGCTGCAC CATCTGTCTT CATCTTCCCG    420

CCATCTGATG AGCAGTTGAA ATCTGGAACT GCCTCTGTTG TGTGCCTGCT GAATAACTTC    480

TATCCCAGAG AGGCCAAAGT ACAGTGGAAG GTGGATAACG CCCTCCAATC GGGTAACTCC    540

CAGGAGAGTG TCACAGAGCA GGACAGCAAG GACAGCACCT ACAGCCTCAG CAGCACCCTG    600

ACGCTGAGCA AAGCAGACTA CGAGAAACAC AAAGTCTACG CCTGCGAAGT CACCCATCAG    660

GGCCTGAGTT CGCCCGTCAC AAAGAGCTTC AACAGGGGAG AGTGT                    705
```

(2) INFORMATION FOR SEQ ID NO: 18:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

```
Met Asp Phe Gln Val Gln Ile Phe Ser Phe Leu Leu Ile Ser Ala Ser
1               5                   10                  15

Val Ile Met Ser Arg Gly Gln Thr Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Thr Tyr Ile His Trp Tyr Gln Gln Lys Pro Gly Ser Ser
    50                  55                  60

Pro Lys Ser Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
            85                  90                  95

Ser Arg Val Glu Ala Glu Asp Ala Ala Thr Tyr Tyr Cys Gln His Trp
            100                 105                 110

Ser Ser Lys Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

(2) INFORMATION FOR SEQ ID NO: 19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

```
AAGCTTGAAT TCGCCGCCAC TATGGATTTT CAAGTGCAG                    39
```

(2) INFORMATION FOR SEQ ID NO: 20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

```
TTAATTGGAT CCGAGCTCCT ATTAACACTC TCCCCTGTTG AAGC              44
```

(2) INFORMATION FOR SEQ ID NO: 21:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 21:

```
AAGCTTCCGG ATCCCTGCAG CCATGGAGTT GTGGCTGAAC TGGATTTTCC        50
```

(2) INFORMATION FOR SEQ ID NO: 22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 22:

```
AAGCTTAGTC TAGATTATCA CTTGCCGGCG CCCAGATC                     38
```

(2) INFORMATION FOR SEQ ID NO: 23:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 23:

```
CGGGGGATCC AGATCTGAGC TCCTGTAGAC GTCGACATTA ATTCCG            46
```

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 24:

```
GGAAAATCCA GTTCAGCCAC AACTCCATGG                                30
```

(2) INFORMATION FOR SEQ ID NO: 25:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 25:

```
ATGAAGTTGT GGCTGAACTG GATTTTCCTT GTAACACTTT TAAATGGAAT TCAGTGTGAG     60
GTGCAGCTGC AGCAGTCTGG GGCAGAGCTT GTGAGGTCAG GGGCCTCAGT CAAGTTGTCC    120
TGCACAGCTT CTGGCTTCAA CATTAAAGAC AACTATATGC ACTGGGTGAA GCAGAGGCCT    180
GAACAGGGCC TGGAGTGGAT TGCATGGATT GATCCTGAGA ATGGTGATAC TGAATATGCC    240
CCGAAGTTCC GGGGCAAGGC CACTTTGACT GCAGACTCAT CCTCCAACAC AGCCTACCTG    300
CACCTCAGCA GCCTGACATC TGAGGACACT GCCGTCTATT ACTGTCATGT CCTGATCTAT    360
GCTGGTTATT TGGCTATGGA CTACTGGGGT CAAGGAACCT CAGTCGCCGT GAGCTCGGCT    420
AGCACCAAGG GACCATCGGT CTTCCCCCTG GCCCCCTGCT CCAGGAGCAC CTCCGAGAGC    480
ACAGCCGCCC TGGGCTGCCT GGTCAAGGAC TACTTCCCCG AACCGGTGAC GGTGTCGTGG    540
AACTCAGGCG CTCTGACCAG CGGCGTGCAC ACCTTCCCGG CTGTCCTACA GTCCTCAGGA    600
CTCTACTCCC TCAGCAGCGT CGTGACGGTG CCCTCCAGCA ACTTCGGCAC CCAGACCTAC    660
ACCTGCAACG TAGATCACAA GCCCAGCAAC ACCAAGGTGG ACAAGACAGT TGGCGGTGGT    720
GGCTCTGGTG GTGGCGGTAG CGGTGGCGGG GGTTCCCAGA AGCGCGACAA CGTGCTGTTC    780
CAGGCAGCTA CCGACGAGCA GCCGGCCGTG ATCAAGACGC TGGAGAAGCT GGTCAACATC    840
GAGACCGGCA CCGGTGACGC CGAGGGCATC GCCGCTGCGG GCAACTTCCT CGAGGCCGAG    900
CTCAAGAACC TCGGCTTCAC GGTCACGCGA AGCAAGTCGG CCGGCCTGGT GGTGGGCGAC    960
AACATCGTGG GCAAGATCAA GGGCCGCGGC GGCAAGAACC TGCTGCTGAT GTCGCACATG   1020
GACACCGTCT ACCTCAAGGG CATTCTCGCG AAGGCCCCGT TCCGCGTCGA AGGCGACAAG   1080
GCCTACGGCC CGGGCATCGC CGACGACAAG GGCGGCAACG CGGTCATCCT GCACACGCTC   1140
AAGCTGCTGA AGGAATACGG CGTGCGCGAC TACGGCACCA TCACCGTGCT GTTCAACACC   1200
GACGAGGAAA AGGGTTCCTT CGGCTCGCGC GACCTGATCC AGGAAGAAGC CAAGCTGGCC   1260
GACTACGTGC TCTCCTTCGA GCCCACCAGC GCAGGCGACG AAAAACTCTC GCTGGGCACC   1320
TCGGGCATCG CCTACGTGCA GGTCCAGATC ACCGGCAAGG CCTCGCATGC CGGCGCCGCG   1380
CCCGAGCTGG GCGTGAACGC GCTGGTCGAG GCTTCCGACC TCGTGCTGCG CACGATGAAC   1440
ATCGACGACA AGGCGAAGAA CCTGCGCTTC CAGTGGACCA TCGCCAAGGC CGGCCAGGTC   1500
TCGAACATCA TCCCCGCCAG CGCCACGCTG AACGCCGACG TGCGCTACGC GCGCAACGAG   1560
```

```
GACTTCGACG CCGCCATGAA GACGCTGGAA GAGCGCGCGC AGCAGAAGAA GCTGCCCGAG      1620

GCCGACGTGA AGGTGATCGT CACGCGCGGC CGCCCGGCCT TCAATGCCGG CGAAGGCGGC      1680

AAGAAGCTGG TCGACAAGGC GGTGGCCTAC TACAAGGAAG CCGGCGGCAC GCTGGGCGTG      1740

GAAGAGCGCA CCGGCGGCGG CACCGACGCG GCCTACGCCG CGCTCTCAGG CAAGCCAGTG      1800

ATCGAGAGCC TGGGCCTGCC GGGCTTCGGC TACCACAGCG ACAAGGCCGA GTACGTGGAC      1860

ATCAGCGCGA TTCCGCGCCG CCTGTACATG GCTGCGCGCC TGATCATGGA TCTGGGCGCC      1920

GGCAAG      1926
```

(2) INFORMATION FOR SEQ ID NO: 26:

(i) SEQUENCE CHARACTERISTICS:
        (A) LENGTH: 642 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

```
Met Lys Leu Trp Leu Asn Trp Ile Phe Leu Val Thr Leu Leu Asn Gly
1               5                   10                  15

Ile Gln Cys Glu Val Gln Leu Gln Gln Ser Gly Ala Glu Leu Val Arg
            20                  25                  30

Ser Gly Ala Ser Val Lys Leu Ser Cys Thr Ala Ser Gly Phe Asn Ile
        35                  40                  45

Lys Asp Asn Tyr Met His Trp Val Lys Gln Arg Pro Glu Gln Gly Leu
    50                  55                  60

Glu Trp Ile Ala Trp Ile Asp Pro Glu Asn Gly Asp Thr Glu Tyr Ala
65                  70                  75                  80

Pro Lys Phe Arg Gly Lys Ala Thr Leu Thr Ala Asp Ser Ser Ser Asn
                85                  90                  95

Thr Ala Tyr Leu His Leu Ser Ser Leu Thr Ser Glu Asp Thr Ala Val
            100                 105                 110

Tyr Tyr Cys His Val Leu Ile Tyr Ala Gly Tyr Leu Ala Met Asp Tyr
        115                 120                 125

Trp Gly Gln Gly Thr Ser Val Ala Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Gly Gly Gly
225                 230                 235                 240

Gly Ser Gly Gly Gly Gly Ser Gly Gly Gly Gly Ser Gln Lys Arg Asp
                245                 250                 255

Asn Val Leu Phe Gln Ala Ala Thr Asp Glu Gln Pro Ala Val Ile Lys
            260                 265                 270
```

```
Thr Leu Glu Lys Leu Val Asn Ile Glu Thr Gly Thr Gly Asp Ala Glu
            275                 280                 285

Gly Ile Ala Ala Ala Gly Asn Phe Leu Glu Ala Glu Leu Lys Asn Leu
        290                 295                 300

Gly Phe Thr Val Thr Arg Ser Lys Ser Ala Gly Leu Val Val Gly Asp
305                 310                 315                 320

Asn Ile Val Gly Lys Ile Lys Gly Arg Gly Lys Asn Leu Leu Leu
                325                 330                 335

Met Ser His Met Asp Thr Val Tyr Leu Lys Gly Ile Leu Ala Lys Ala
                340                 345                 350

Pro Phe Arg Val Glu Gly Asp Lys Ala Tyr Gly Pro Gly Ile Ala Asp
        355                 360                 365

Asp Lys Gly Gly Asn Ala Val Ile Leu His Thr Leu Lys Leu Leu Lys
    370                 375                 380

Glu Tyr Gly Val Arg Asp Tyr Gly Thr Ile Thr Val Leu Phe Asn Thr
385                 390                 395                 400

Asp Glu Glu Lys Gly Ser Phe Gly Ser Arg Asp Leu Ile Gln Glu Glu
                405                 410                 415

Ala Lys Leu Ala Asp Tyr Val Leu Ser Phe Glu Pro Thr Ser Ala Gly
                420                 425                 430

Asp Glu Lys Leu Ser Leu Gly Thr Ser Gly Ile Ala Tyr Val Gln Val
            435                 440                 445

Gln Ile Thr Gly Lys Ala Ser His Ala Gly Ala Ala Pro Glu Leu Gly
    450                 455                 460

Val Asn Ala Leu Val Glu Ala Ser Asp Leu Val Leu Arg Thr Met Asn
465                 470                 475                 480

Ile Asp Asp Lys Ala Lys Asn Leu Arg Phe Gln Trp Thr Ile Ala Lys
                485                 490                 495

Ala Gly Gln Val Ser Asn Ile Ile Pro Ala Ser Ala Thr Leu Asn Ala
                500                 505                 510

Asp Val Arg Tyr Ala Arg Asn Glu Asp Phe Asp Ala Ala Met Lys Thr
            515                 520                 525

Leu Glu Glu Arg Ala Gln Gln Lys Lys Leu Pro Glu Ala Asp Val Lys
    530                 535                 540

Val Ile Val Thr Arg Gly Arg Pro Ala Phe Asn Ala Gly Glu Gly Gly
545                 550                 555                 560

Lys Lys Leu Val Asp Lys Ala Val Ala Tyr Tyr Lys Glu Ala Gly Gly
                565                 570                 575

Thr Leu Gly Val Glu Glu Arg Thr Gly Gly Thr Asp Ala Ala Tyr
            580                 585                 590

Ala Ala Leu Ser Gly Lys Pro Val Ile Glu Ser Leu Gly Leu Pro Gly
        595                 600                 605

Phe Gly Tyr His Ser Asp Lys Ala Glu Tyr Val Asp Ile Ser Ala Ile
    610                 615                 620

Pro Arg Arg Leu Tyr Met Ala Ala Arg Leu Ile Met Asp Leu Gly Ala
625                 630                 635                 640

Gly Lys
```

(2) INFORMATION FOR SEQ ID NO: 27:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 27:

AAGCTTGGAA TTCAGTGTCA GGTCCAACTG CAGCAGCCT                           39

(2) INFORMATION FOR SEQ ID NO: 28:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 28:

GCTACCGCCA CCTCCGGAGC CACCACCGCC CCGTTTGATC TCGAGCTTGG TGCC          54

(2) INFORMATION FOR SEQ ID NO: 29:

(i) SEQUENCE CHARACTERISTICS:
           (A) LENGTH: 58 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 29:

TCCGGAGGTG GCGGTAGCGG TGGCGGGGGT TCCCAGAAGC GCGACAACGT GCTGTTCC      58

(2) INFORMATION FOR SEQ ID NO: 30:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 30:

CCTCGAGGAA TTCTTTCACT TGCC                                           24

(2) INFORMATION FOR SEQ ID NO: 31:

(i) SEQUENCE CHARACTERISTICS:
           (A) LENGTH: 2019 base pairs
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO: 31:

ATGAAGTTGT GGCTGAACTG GATTTTCCTT GTAACACTTT TAAATGGAAT TCAGTGTCAG    60

GTCCAACTGC AGCAGCCTGG GGCTGAACTG GTGAAGCCTG GGGCTTCAGT GCAGCTGTCC    120

TGCAAGGCTT CTGGCTACAC CTTCACCGGC TACTGGATAC ACTGGGTGAA GCAGAGGCCT    180

GGACAAGGCC TTGAGTGGAT TGGAGAGGTT AATCCTAGTA CCGGTCGTTC TGACTACAAT    240

GAGAAGTTCA AGAACAAGGC CACACTGACT GTAGACAAAT CCTCCACCAC AGCCTACATG    300

CAACTCAGCA GCCTGACATC TGAGGACTCT GCGGTCTATT ACTGTGCAAG AGAGAGGGCC    360

TATGGTTACG ACGATGCTAT GGACTACTGG GGCCAAGGGA CCACGGTCAC CGTCTCCTCA    420

GGTGGCGGTG GCTCGGGCGG TGGTGGGTCG GGTGGCGGCG GATCTGACAT TGAGCTCTCA    480

```
CAGTCTCCAT CCTCCCTGGC TGTGTCAGCA GGAGAGAAGG TCACCATGAG CTGCAAATCC      540

AGTCAGAGTC TCCTCAACAG TAGAACCCGA AGAACTACT  TGGCTTGGTA CCAGCAGAGA      600

CCAGGGCAGT CTCCTAAACT GCTGATCTAT TGGGCATCCA CTAGGACATC TGGGGTCCCT      660

GATCGCTTCA CAGGCAGTGG ATCTGGGACA GATTTCACTC TCACCATCAG CAGTGTGCAG      720

GCTGAAGACC TGGCAATTTA TTACTGCAAG CAATCTTATA CTCTTCGGAC GTTCGGTGGA      780

GGCACCAAGC TCGAGATCAA ACGGGCGGT  GGTGGCTCCG GAGGTGGCGG TAGCGGTGGC      840

GGGGGTTCCC AGAAGCGCGA CAACGTGCTG TTCCAGGCAG CTACCGACGA GCAGCCGGCC      900

GTGATCAAGA CGCTGGAGAA GCTGGTCAAC ATCGAGACCG GCACCGGTGA CGCCGAGGGC      960

ATCGCCGCTG CGGGCAACTT CCTCGAGGCC GAGCTCAAGA ACCTCGGCTT CACGGTCACG     1020

CGAAGCAAGT CGGCCGGCCT GGTGGTGGGC GACAACATCG TGGGCAAGAT CAAGGGCCGC     1080

GGCGGCAAGA ACCTGCTGCT GATGTCGCAC ATGGACACCG TCTACCTCAA GGGCATTCTC     1140

GCGAAGGCCC CGTTCCGCGT CGAAGGCGAC AAGGCCTACG GCCCGGGCAT CGCCGACGAC     1200

AAGGGCGGCA ACGCGGTCAT CCTGCACACG CTCAAGCTGC TGAAGGAATA CGGCGTGCGC     1260

GACTACGGCA CCATCACCGT GCTGTTCAAC ACCGACGAGG AAAAGGGTTC CTTCGGCTCG     1320

CGCGACCTGA TCCAGGAAGA AGCCAAGCTG GCCGACTACG TGCTCTCCTT CGAGCCCACC     1380

AGCGCAGGCG ACGAAAAACT CTCGCTGGGC ACCTCGGGCA TCGCCTACGT GCAGGTCCAG     1440

ATCACCGGCA AGGCCTCGCA TGCCGGCGCC GCGCCCGAGC TGGGCGTGAA CGCGCTGGTC     1500

GAGGCTTCCG ACCTCGTGCT GCGCACGATG AACATCGACA CAAGGCGAA  GAACCTGCGC     1560

TTCCAGTGGA CCATCGCCAA GGCCGGCCAG GTCTCGAACA TCATCCCCGC CAGCGCCACG     1620

CTGAACGCCG ACGTGCGCTA CGCGCGCAAC GAGGACTTCG ACGCCGCCAT GAAGACGCTG     1680

GAAGAGCGCG CGCAGCAGAA GAAGCTGCCC GAGGCCGACG TGAAGGTGAT CGTCACGCGC     1740

GGCCGCCCGG CCTTCAATGC CGGCGAAGGC GGCAAGAAGC TGGTCGACAA GGCGGTGGCC     1800

TACTACAAGG AAGCCGGCGG CACGCTGGGC GTGGAAGAGC GCACCGGCGG CGGCACCGAC     1860

GCGGCCTACG CCGCGCTCTC AGGCAAGCCA GTGATCGAGA GCCTGGGCCT GCCGGGCTTC     1920

GGCTACCACA GCGACAAGGC CGAGTACGTG GACATCAGCG CGATTCCGCG CCGCCTGTAC     1980

ATGGCTGCGC GCCTGATCAT GGATCTGGGC GCCGGCAAG                           2019
```

(2) INFORMATION FOR SEQ ID NO: 32:

(i) SEQUENCE CHARACTERISTICS:
        (A) LENGTH: 673 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 32:

```
Met Lys Leu Trp Leu Asn Trp Ile Phe Leu Val Thr Leu Leu Asn Gly
1               5                   10                  15

Ile Gln Cys Gln Val Gln Leu Gln Gln Pro Gly Ala Glu Leu Val Lys
                20                  25                  30

Pro Gly Ala Ser Val Gln Leu Ser Cys Lys Ala Ser Gly Tyr Thr Phe
            35                  40                  45

Thr Gly Tyr Trp Ile His Trp Val Lys Gln Arg Pro Gly Gln Gly Leu
        50                  55                  60

Glu Trp Ile Gly Glu Val Asn Pro Ser Thr Gly Arg Ser Asp Tyr Asn
65                  70                  75                  80
```

-continued

```
Glu Lys Phe Lys Asn Lys Ala Thr Leu Thr Val Asp Lys Ser Ser Thr
                85                  90                  95
Thr Ala Tyr Met Gln Leu Ser Ser Leu Thr Ser Glu Asp Ser Ala Val
            100                 105                 110
Tyr Tyr Cys Ala Arg Glu Arg Ala Tyr Gly Tyr Asp Asp Ala Met Asp
        115                 120                 125
Tyr Trp Gly Gln Gly Thr Thr Val Thr Val Ser Ser Gly Gly Gly Gly
130                 135                 140
Ser Gly Gly Gly Gly Ser Gly Gly Gly Gly Ser Asp Ile Glu Leu Ser
145                 150                 155                 160
Gln Ser Pro Ser Ser Leu Ala Val Ser Ala Gly Glu Lys Val Thr Met
                165                 170                 175
Ser Cys Lys Ser Ser Gln Ser Leu Leu Asn Ser Arg Thr Arg Lys Asn
            180                 185                 190
Tyr Leu Ala Trp Tyr Gln Gln Arg Pro Gly Gln Ser Pro Lys Leu Leu
        195                 200                 205
Ile Tyr Trp Ala Ser Thr Arg Thr Ser Gly Val Pro Asp Arg Phe Thr
    210                 215                 220
Gly Ser Gly Ser Gly Thr Asp Phe Thr Leu Thr Ile Ser Ser Val Gln
225                 230                 235                 240
Ala Glu Asp Leu Ala Ile Tyr Tyr Cys Lys Gln Ser Tyr Thr Leu Arg
                245                 250                 255
Thr Phe Gly Gly Gly Thr Lys Leu Glu Ile Lys Arg Gly Gly Gly Gly
            260                 265                 270
Ser Gly Gly Gly Gly Ser Gly Gly Gly Gly Ser Gln Lys Arg Asp Asn
        275                 280                 285
Val Leu Phe Gln Ala Ala Thr Asp Glu Gln Pro Ala Val Ile Lys Thr
290                 295                 300
Leu Glu Lys Leu Val Asn Ile Glu Thr Gly Thr Gly Asp Ala Glu Gly
305                 310                 315                 320
Ile Ala Ala Ala Gly Asn Phe Leu Glu Ala Glu Leu Lys Asn Leu Gly
                325                 330                 335
Phe Thr Val Thr Arg Ser Lys Ser Ala Gly Leu Val Val Gly Asp Asn
            340                 345                 350
Ile Val Gly Lys Ile Lys Gly Arg Gly Gly Lys Asn Leu Leu Leu Met
        355                 360                 365
Ser His Met Asp Thr Val Tyr Leu Lys Gly Ile Leu Ala Lys Ala Pro
370                 375                 380
Phe Arg Val Glu Gly Asp Lys Ala Tyr Gly Pro Gly Ile Ala Asp Asp
385                 390                 395                 400
Lys Gly Gly Asn Ala Val Ile Leu His Thr Leu Lys Leu Leu Lys Glu
                405                 410                 415
Tyr Gly Val Arg Asp Tyr Gly Thr Ile Thr Val Leu Phe Asn Thr Asp
            420                 425                 430
Glu Glu Lys Gly Ser Phe Gly Ser Arg Asp Leu Ile Gln Glu Glu Ala
        435                 440                 445
Lys Leu Ala Asp Tyr Val Leu Ser Phe Glu Pro Thr Ser Ala Gly Asp
    450                 455                 460
Glu Lys Leu Ser Leu Gly Thr Ser Gly Ile Ala Tyr Val Gln Val Gln
465                 470                 475                 480
Ile Thr Gly Lys Ala Ser His Ala Gly Ala Ala Pro Glu Leu Gly Val
                485                 490                 495
```

Asn Ala Leu Val Glu Ala Ser Asp Leu Val Leu Arg Thr Met Asn Ile
            500                 505                 510

Asp Asp Lys Ala Lys Asn Leu Arg Phe Gln Trp Thr Ile Ala Lys Ala
            515                 520                 525

Gly Gln Val Ser Asn Ile Ile Pro Ala Ser Ala Thr Leu Asn Ala Asp
            530                 535                 540

Val Arg Tyr Ala Arg Asn Glu Asp Phe Asp Ala Ala Met Lys Thr Leu
545                 550                 555                 560

Glu Glu Arg Ala Gln Gln Lys Lys Leu Pro Glu Ala Asp Val Lys Val
                565                 570                 575

Ile Val Thr Arg Gly Arg Pro Ala Phe Asn Ala Gly Glu Gly Gly Lys
            580                 585                 590

Lys Leu Val Asp Lys Ala Val Ala Tyr Tyr Lys Glu Ala Gly Gly Thr
            595                 600                 605

Leu Gly Val Glu Glu Arg Thr Gly Gly Thr Asp Ala Ala Tyr Ala
            610                 615                 620

Ala Leu Ser Gly Lys Pro Val Ile Glu Ser Leu Gly Leu Pro Gly Phe
625                 630                 635                 640

Gly Tyr His Ser Asp Lys Ala Glu Tyr Val Asp Ile Ser Ala Ile Pro
                645                 650                 655

Arg Arg Leu Tyr Met Ala Ala Arg Leu Ile Met Asp Leu Gly Ala Gly
            660                 665                 670

Lys (2) INFORMATION FOR SEQ ID NO: 33:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 33:

GGGCGCCGGC AAGTGATAAA ATTCCTCGAG GAGCTCC                    37

(2) INFORMATION FOR SEQ ID NO: 34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 34:

CGCCACCTCT GACTTGAGC                                        19

(2) INFORMATION FOR SEQ ID NO: 35:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 35:

GGAGCTCCTC GAGGAATTTT ATCACTTGCC GGCGCCC                    37

(2) INFORMATION FOR SEQ ID NO: 36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 36:

```
GCTGAACGCC GACGTGCGC                                                19
```

(2) INFORMATION FOR SEQ ID NO: 37:

(i) SEQUENCE CHARACTERISTICS:
        (A) LENGTH: 2025 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 37:

```
ATGAAGTTGT GGCTGAACTG GATTTTCCTT GTAACACTTT TAAATGGAAT TCAGTGTCAG      60
GTCCAACTGC AGCAGCCTGG GGCTGAACTG GTGAAGCCTG GGGCTTCAGT GCAGCTGTCC     120
TGCAAGGCTT CTGGCTACAC CTTCACCGGC TACTGGATAC ACTGGGTGAA GCAGAGGCCT     180
GGACAAGGCC TTGAGTGGAT TGGAGAGGTT AATCCTAGTA CCGGTCGTTC TGACTACAAT     240
GAGAAGTTCA AGAACAAGGC CACACTGACT GTAGACAAAT CCTCCACCAC AGCCTACATG     300
CAACTCAGCA GCCTGACATC TGAGGACTCT GCGGTCTATT ACTGTGCAAG AGAGAGGGCC     360
TATGGTTACG ACGATGCTAT GGACTACTGG GGCCAAGGGA CCACGGTCAC CGTCTCCTCA     420
GGTGGCGGTG GCTCGGGCGG TGGTGGGTCG GGTGGCGGCG GATCTGACAT TGAGCTCTCA     480
CAGTCTCCAT CCTCCCTGGC TGTGTCAGCA GGAGAGAAGG TCACCATGAG CTGCAAATCC     540
AGTCAGAGTC TCCTCAACAG TAGAACCCGA AGAACTACT TGGCTTGGTA CCAGCAGAGA      600
CCAGGGCAGT CTCCTAAACT GCTGATCTAT TGGGCATCCA CTAGGACATC TGGGGTCCCT     660
GATCGCTTCA CAGGCAGTGG ATCTGGGACA GATTTCACTC TCACCATCAG CAGTGTGCAG     720
GCTGAAGACC TGGCAATTTA TTACTGCAAG CAATCTTATA CTCTTCGGAC GTTCGGTGGA     780
GGCACCAAGC TCGAGATCAA ACGGGGCGGT GGTGGCTCCG GAGGTGGCGG TAGCGGTGGC     840
GGGGGTTCCC AGAAGCGCGA CAACGTGCTG TTCCAGGCAG CTACCGACGA GCAGCCGGCC     900
GTGATCAAGA CGCTGGAGAA GCTGGTCAAC ATCGAGACCG GCACCGGTGA CGCCGAGGGC     960
ATCGCCGCTG CGGGCAACTT CCTCGAGGCC GAGCTCAAGA ACCTCGGCTT CACGGTCACG    1020
CGAAGCAAGT CGGCCGGCCT GGTGGTGGGC GACAACATCG TGGGCAAGAT CAAGGGCCGC    1080
GGCGGCAAGA ACCTGCTGCT GATGTCGCAC ATGGACACCG TCTACCTCAA GGGCATTCTC    1140
GCGAAGGCCC CGTTCCGCGT CGAAGGCGAC AAGGCCTACG GCCCGGGCAT CGCCGACGAC    1200
AAGGGCGGCA ACGCGGTCAT CCTGCACACG CTCAAGCTGC TGAAGGAATA CGGCGTGCGC    1260
GACTACGGCA CCATCACCGT GCTGTTCAAC ACCGACGAGG AAAAGGGTTC CTTCGGCTCG    1320
CGCGACCTGA TCCAGGAAGA AGCCAAGCTG GCCGACTACG TGCTCTCCTT CGAGCCCACC    1380
AGCGCAGGCG ACGAAAAACT CTCGCTGGGC ACCTCGGGCA TCGCCTACGT GCAGGTCCAG    1440
ATCACCGGCA AGGCCTCGCA TGCCGGCGCC GCGCCCGAGC TGGGCGTGAA CGCGCTGGTC    1500
GAGGCTTCCG ACCTCGTGCT GCGCACGATG AACATCGACG ACAAGGCGAA GAACCTGCGC    1560
```

```
TTCCAGTGGA CCATCGCCAA GGCCGGCCAG GTCTCGAACA TCATCCCCGC CAGCGCCACG      1620

CTGAACGCCG ACGTGCGCTA CGCGCGCAAC GAGGACTTCG ACGCCGCCAT GAAGACGCTG      1680

GAAGAGCGCG CGCAGCAGAA GAAGCTGCCC GAGGCCGACG TGAAGGTGAT CGTCACGCGC      1740

GGCCGCCCGG CCTTCAATGC CGGCGAAGGC GGCAAGAAGC TGGTCGACAA GGCGGTGGCC      1800

TACTACAAGG AAGCCGGCGG CACGCTGGGC GTGGAAGAGC GCACCGGCGG CGGCACCGAC      1860

GCGGCCTACG CCGCGCTCTC AGGCAAGCCA GTGATCGAGA GCCTGGGCCT GCCGGGCTTC      1920

GGCTACCACA CGACAAGGC CGAGTACGTG GACATCAGCG CGATTCCGCG CCGCCTGTAC      1980

ATGGCTGCGC GCCTGATCAT GGATCTGGGC GCCGGCAAGT GATAA                    2025
```

(2) INFORMATION FOR SEQ ID NO: 38:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 38:

```
Met Lys Tyr Leu Leu Pro Thr Ala Ala Gly Leu Leu Leu Ala
1               5                  10                  15

Ala Gln Pro Ala Met Ala Gln Val Gln Leu Gln Gln Pro Gly Ala Glu
            20                  25                  30

Leu Val Lys Pro Gly Ala Ser Val Gln Leu Ser Cys Lys Ala Ser Gly
            35                  40                  45

Tyr Thr Phe Thr Gly Tyr Trp Ile His Trp Val Lys Gln Arg Pro Gly
        50                  55                  60

Gln Gly Leu Glu Trp Ile Gly Glu Val Asn Pro Ser Thr Gly Arg Ser
65                  70                  75                  80

Asp Tyr Asn Glu Lys Phe Lys Asn Lys Ala Thr Leu Thr Val Asp Lys
                85                  90                  95

Ser Ser Thr Thr Ala Tyr Met Gln Leu Ser Ser Leu Thr Ser Glu Asp
            100                 105                 110

Ser Ala Val Tyr Tyr Cys Ala Arg Glu Arg Ala Tyr Gly Tyr Asp Asp
        115                 120                 125

Ala Met Asp Tyr Trp Gly Gln Gly Thr Thr Val Thr Val Ser Ser Gly
    130                 135                 140

Gly Gly Gly Ser Gly Gly Gly Gly Ser Gly Gly Gly Ser Asp Ile
145                 150                 155                 160

Glu Leu Ser Gln Ser Pro Ser Ser Leu Ala Val Ser Ala Gly Glu Lys
                165                 170                 175

Val Thr Met Ser Cys Lys Ser Ser Gln Ser Leu Leu Asn Ser Arg Thr
            180                 185                 190

Arg Lys Asn Tyr Leu Ala Trp Tyr Gln Gln Arg Pro Gly Gln Ser Pro
        195                 200                 205

Lys Leu Leu Ile Tyr Trp Ala Ser Thr Arg Thr Ser Gly Val Pro Asp
    210                 215                 220

Arg Phe Thr Gly Ser Gly Ser Gly Thr Asp Phe Thr Leu Thr Ile Ser
225                 230                 235                 240

Ser Val Gln Ala Glu Asp Leu Ala Ile Tyr Tyr Cys Lys Gln Ser Tyr
                245                 250                 255

Thr Leu Arg Thr Phe Gly Gly Gly Thr Lys Leu Glu Ile Lys Arg Glu
            260                 265                 270
```

```
Gln Lys Leu Ile Ser Glu Glu Asp Leu Asn His His His His His His
    275                 280                 285
```

(2) INFORMATION FOR SEQ ID NO: 39:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 39:

```
GCCCAACCAG CCATGGCCGA GGTGCAGCTG CAGCAG                              36
```

(2) INFORMATION FOR SEQ ID NO: 40:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 40:

```
CGACCCACCA CCGCCCGAGC CACCGCCACC CGAGCTCACG GCGACTGAGG TTCC          54
```

(2) INFORMATION FOR SEQ ID NO: 41:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 41:

```
TCGGGCGGTG GTGGGTCGGG TGGCGGCGGA TCTCAGATTG TGCTCACCCA GTCT          54
```

(2) INFORMATION FOR SEQ ID NO: 42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 42:

```
CCGTTTGATC TCGAGCTTGG TCCC                                           24
```

(2) INFORMATION FOR SEQ ID NO: 43:

(i) SEQUENCE CHARACTERISTICS:
        (A) LENGTH: 843 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 43:

```
ATGAAATACC TATTGCCTAC GGCAGCCGCT GGATTGTTAT TACTCGCTGC CCAACCAGCC    60

ATGGCCGAGG TGCAGCTGCA GCAGTCTGGG GCAGAGCTTG TGAGGTCAGG GGCCTCAGTC   120
```

```
AAGTTGTCCT GCACAGCTTC TGGCTTCAAC ATTAAAGACA ACTATATGCA CTGGGTGAAG    180

CAGAGGCCTG AACAGGGCCT GGAGTGGATT GCATGGATTG ATCCTGAGAA TGGTGATACT    240

GAATATGCCC CGAAGTTCCG GGGCAAGGCC ACTTTGACTG CAGACTCATC CTCCAACACA    300

GCCTACCTGC ACCTCAGCAG CCTGACATCT GAGGACACTG CCGTCTATTA CTGTCATGTC    360

CTGATCTATG CTGGTTATTT GGCTATGGAC TACTGGGGTC AAGGAACCTC AGTCGCCGTG    420

AGCTCGGGTG GCGGTGGCTC GGGCGGTGGT GGGTCGGGTG GCGGCGGATC TCAGATTGTG    480

CTCACCCAGT CTCCAGCAAT CATGTCTGCA TCTCCAGGGG AGAAGGTCAC CATAACCTGC    540

AGTGCCAGCT CAAGTGTAAC TTACATGCAC TGGTTCCAGC AGAAGCCAGG CACTTCTCCC    600

AAACTCTGGA TTTATAGCAC ATCCAACCTG GCTTCTGGAG TCCCTGCTCG CTTCAGTGGC    660

AGTGGATCTG GGACCTCTTA CTCTCTCACA ATCAGCCGAA TGGAGGCTGA AGATGCTGCC    720

ACTTATTACT GCCAGCAAAG GAGTACTTAC CCGCTCACGT TCGGTGCTGG GACCAAGCTC    780

GAGATCAAAC GGGAACAAAA ACTCATCTCA GAAGAAGATC TGAATCACCA CCATCACCAC    840

CAT                                                                  843

(2) INFORMATION FOR SEQ ID NO: 44:

(i) SEQUENCE CHARACTERISTICS:
        (A) LENGTH: 281 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 44:

Met Lys Tyr Leu Leu Pro Thr Ala Ala Ala Gly Leu Leu Leu Ala
1               5                   10                  15

Ala Gln Pro Ala Met Ala Glu Val Gln Leu Gln Gln Ser Gly Ala Glu
                20                  25                  30

Leu Val Arg Ser Gly Ala Ser Val Lys Leu Ser Cys Thr Ala Ser Gly
            35                  40                  45

Phe Asn Ile Lys Asp Asn Tyr Met His Trp Val Lys Gln Arg Pro Glu
        50                  55                  60

Gln Gly Leu Glu Trp Ile Ala Trp Ile Asp Pro Glu Asn Gly Asp Thr
65                  70                  75                  80

Glu Tyr Ala Pro Lys Phe Arg Gly Lys Ala Thr Leu Thr Ala Asp Ser
                85                  90                  95

Ser Ser Asn Thr Ala Tyr Leu His Leu Ser Ser Leu Thr Ser Glu Asp
            100                 105                 110

Thr Ala Val Tyr Tyr Cys His Val Leu Ile Tyr Ala Gly Tyr Leu Ala
        115                 120                 125

Met Asp Tyr Trp Gly Gln Gly Thr Ser Val Ala Val Ser Ser Gly Gly
    130                 135                 140

Gly Gly Ser Gly Gly Gly Gly Ser Gly Gly Gly Gly Ser Gln Ile Val
145                 150                 155                 160

Leu Thr Gln Ser Pro Ala Ile Met Ser Ala Ser Pro Gly Glu Lys Val
                165                 170                 175

Thr Ile Thr Cys Ser Ala Ser Ser Val Thr Tyr Met His Trp Phe
            180                 185                 190

Gln Gln Lys Pro Gly Thr Ser Pro Lys Leu Trp Ile Tyr Ser Thr Ser
        195                 200                 205
```

```
Asn Leu Ala Ser Gly Val Pro Ala Arg Phe Ser Gly Ser Gly Ser Gly
    210                 215                 220

Thr Ser Tyr Ser Leu Thr Ile Ser Arg Met Glu Ala Glu Asp Ala Ala
225                 230                 235                 240

Thr Tyr Tyr Cys Gln Gln Arg Ser Thr Tyr Pro Leu Thr Phe Gly Ala
                245                 250                 255

Gly Thr Lys Leu Glu Ile Lys Arg Glu Gln Lys Leu Ile Ser Glu Glu
            260                 265                 270

Asp Leu Asn His His His His His His
            275                 280
```

(2) INFORMATION FOR SEQ ID NO: 45:

(i) SEQUENCE CHARACTERISTICS:
    (A) LENGTH: 72 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO: 45:

```
TCGAGATCAA ACGGGAACAA AAACTCATCT CAGAAGAAGA TCTGAATCAC CACCATCACC     60

ACCATTAATG AG                                                         72
```

(2) INFORMATION FOR SEQ ID NO: 46:

(i) SEQUENCE CHARACTERISTICS:
    (A) LENGTH: 72 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO: 46:

```
AATTCTCATT AATGGTGGTG ATGGTGGTGA TTCAGATCTT CTTCTGAGAT GAGTTTTTGT     60

TCCCGTTTGA TC                                                         72
```

(2) INFORMATION FOR SEQ ID NO: 47:

(i) SEQUENCE CHARACTERISTICS:
    (A) LENGTH: 864 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO: 47:

```
ATGAAATACC TATTGCCTAC GGCAGCCGCT GGATTGTTAT TACTCGCTGC CCAACCAGCC     60

ATGGCCCAGG TCCAACTGCA GCAGCCTGGG GCTGAACTGG TGAAGCCTGG GGCTTCAGTG    120

CAGCTGTCCT GCAAGGCTTC TGGCTACACC TTCACCGGCT ACTGGATACA CTGGGTGAAG    180

CAGAGGCCTG GACAAGGCCT TGAGTGGATT GGAGAGGTTA ATCCTAGTAC CGGTCGTTCT    240

GACTACAATG AGAAGTTCAA GAACAAGGCC ACACTGACTG TAGACAAATC CTCCACCACA    300

GCCTACATGC AACTCAGCAG CCTGACATCT GAGGACTCTG CGGTCTATTA CTGTGCAAGA    360

GAGAGGGCCA TGGTTACGA CGATGCTATG GACTACTGGG GCCAAGGGAC CACGGTCACC    420

GTCTCCTCAG GTGGCGGTGG CTCGGGCGGT GGTGGGTCGG GTGGCGGCGG ATCTGACATT    480

GAGCTCTCAC AGTCTCCATC CTCCCTGGCT GTGTCAGCAG GAGAGAAGGT CACCATGAGC    540
```

-continued

| | |
|---|---|
| TGCAAATCCA GTCAGAGTCT CCTCAACAGT AGAACCCGAA AGAACTACTT GGCTTGGTAC | 600 |
| CAGCAGAGAC CAGGGCAGTC TCCTAAACTG CTGATCTATT GGGCATCCAC TAGGACATCT | 660 |
| GGGGTCCCTG ATCGCTTCAC AGGCAGTGGA TCTGGGACAG ATTTCACTCT CACCATCAGC | 720 |
| AGTGTGCAGG CTGAAGACCT GGCAATTTAT TACTGCAAGC AATCTTATAC TCTTCGGACG | 780 |
| TTCGGTGGAG GCACCAAGCT CGAGATCAAA CGGGAACAAA AACTCATCTC AGAAGAAGAT | 840 |
| CTGAATCACC ACCATCACCA CCAT | 864 |

(2) INFORMATION FOR SEQ ID NO: 48:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 48:

| | |
|---|---|
| AAGCTTGGAA TTCAGTGTGA GGTGCAGCTG CAGC | 34 |

(2) INFORMATION FOR SEQ ID NO: 49:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 49:

| | |
|---|---|
| CGCCACCTCC GGAGCCACCA CCGCCCCGTT TGATCTCGAG CTTGG | 45 |

(2) INFORMATION FOR SEQ ID NO: 50:

(i) SEQUENCE CHARACTERISTICS:
        (A) LENGTH: 1998 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 50:

| | |
|---|---|
| ATGAAGTTGT GGCTGAACTG GATTTTCCTT GTAACACTTT TAAATGGAAT TCAGTGTGAG | 60 |
| GTGCAGCTGC AGCAGTCTGG GGCAGAGCTT GTGAGGTCAG GGGCCTCAGT CAAGTTGTCC | 120 |
| TGCACAGCTT CTGGCTTCAA CATTAAAGAC AACTATATGC ACTGGGTGAA GCAGAGGCCT | 180 |
| GAACAGGGCC TGGAGTGGAT TGCATGGATT GATCCTGAGA ATGGTGATAC TGAATATGCC | 240 |
| CCGAAGTTCC GGGGCAAGGC CACTTTGACT GCAGACTCAT CCTCCAACAC AGCCTACCTG | 300 |
| CACCTCAGCA GCCTGACATC TGAGGACACT GCCGTCTATT ACTGTCATGT CCTGATCTAT | 360 |
| GCTGGTTATT TGGCTATGGA CTACTGGGGT CAAGGAACCT CAGTCGCCGT GAGCTCGGGT | 420 |
| GGCGGTGGCT CGGGCGGTGG TGGGTCGGGT GGCGGCGGAT CTCAGATTGT GCTCACCCAG | 480 |
| TCTCCAGCAA TCATGTCTGC ATCTCCAGGG GAGAAGGTCA CCATAACCTG CAGTGCCAGC | 540 |
| TCAAGTGTAA CTTACATGCA CTGGTTCCAG CAGAAGCCAG GCACTTCTCC CAAACTCTGG | 600 |
| ATTTATAGCA CATCCAACCT GGCTTCTGGA GTCCCTGCTC GCTTCAGTGG CAGTGGATCT | 660 |
| GGGACCTCTT ACTCTCTCAC AATCAGCCGA ATGGAGGCTG AAGATGCTGC CACTTATTAC | 720 |

-continued

```
TGCCAGCAAA GGAGTACTTA CCCGCTCACG TTCGGTGCTG GGACCAAGCT CGAGATCAAA    780

CGGGGCGGTG GTGGCTCCGG AGGTGGCGGT AGCGGTGGCG GGGGTTCCCA GAAGCGCGAC    840

AACGTGCTGT TCCAGGCAGC TACCGACGAG CAGCCGGCCG TGATCAAGAC GCTGGAGAAG    900

CTGGTCAACA TCGAGACCGG CACCGGTGAC GCCGAGGGCA TCGCCGCTGC GGGCAACTTC    960

CTCGAGGCCG AGCTCAAGAA CCTCGGCTTC ACGGTCACGC GAAGCAAGTC GGCCGGCCTG   1020

GTGGTGGGCG ACAACATCGT GGGCAAGATC AAGGGCCGCG GCGGCAAGAA CCTGCTGCTG   1080

ATGTCGCACA TGGACACCGT CTACCTCAAG GGCATTCTCG CGAAGGCCCC GTTCCGCGTC   1140

GAAGGCGACA AGGCCTACGG CCCGGGCATC GCCGACGACA AGGGCGGCAA CGCGGTCATC   1200

CTGCACACGC TCAAGCTGCT GAAGGAATAC GGCGTGCGCG ACTACGGCAC CATCACCGTG   1260

CTGTTCAACA CCGACGAGGA AAAGGGTTCC TTCGGCTCGC GCGACCTGAT CCAGGAAGAA   1320

GCCAAGCTGG CCGACTACGT GCTCTCCTTC GAGCCCACCA CGCAGGCGA CGAAAAACTC   1380

TCGCTGGGCA CCTCGGGCAT CGCCTACGTG CAGGTCCAGA TCACCGGCAA GGCCTCGCAT   1440

GCCGGCGCCG CGCCCGAGCT GGGCGTGAAC GCGCTGGTCG AGGCTTCCGA CCTCGTGCTG   1500

CGCACGATGA ACATCGACGA CAAGGCGAAG AACCTGCGCT TCCAGTGGAC CATCGCCAAG   1560

GCCGGCCAGG TCTCGAACAT CATCCCCGCC AGCGCCACGC TGAACGCCGA CGTGCGCTAC   1620

GCGCGCAACG AGGACTTCGA CGCCGCCATG AAGACGCTGG AAGAGCGCGC GCAGCAGAAG   1680

AAGCTGCCCG AGGCCGACGT GAAGGTGATC GTCACGCGCG GCCGCCCGGC CTTCAATGCC   1740

GGCGAAGGCG GCAAGAAGCT GGTCGACAAG GCGGTGGCCT ACTACAAGGA AGCCGGCGGC   1800

ACGCTGGGCG TGGAAGAGCG CACCGGCGGC GGCACCGACG CGGCCTACGC CGCGCTCTCA   1860

GGCAAGCCAG TGATCGAGAG CCTGGGCCTG CCGGGCTTCG GCTACCACAG CGACAAGGCC   1920

GAGTACGTGG ACATCAGCGC GATTCCGCGC CGCCTGTACA TGGCTGCGCG CCTGATCATG   1980

GATCTGGGCG CCGGCAAG                                                1998
```

(2) INFORMATION FOR SEQ ID NO: 51:

(i) SEQUENCE CHARACTERISTICS:
        (A) LENGTH: 666 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 51:

```
Met Lys Leu Trp Leu Asn Trp Ile Phe Leu Val Thr Leu Leu Asn Gly
  1               5                  10                  15

Ile Gln Cys Glu Val Gln Leu Gln Gln Ser Gly Ala Glu Leu Val Arg
             20                  25                  30

Ser Gly Ala Ser Val Lys Leu Ser Cys Thr Ala Ser Gly Phe Asn Ile
         35                  40                  45

Lys Asp Asn Tyr Met His Trp Val Lys Gln Arg Pro Glu Gln Gly Leu
     50                  55                  60

Glu Trp Ile Ala Trp Ile Asp Pro Glu Asn Gly Asp Thr Glu Tyr Ala
 65                  70                  75                  80

Pro Lys Phe Arg Gly Lys Ala Thr Leu Thr Ala Asp Ser Ser Ser Asn
                 85                  90                  95

Thr Ala Tyr Leu His Leu Ser Ser Leu Thr Ser Glu Asp Thr Ala Val
            100                 105                 110
```

-continued

```
Tyr Tyr Cys His Val Leu Ile Tyr Ala Gly Tyr Leu Ala Met Asp Tyr
        115                 120                 125

Trp Gly Gln Gly Thr Ser Val Ala Val Ser Ser Gly Gly Gly Gly Ser
130                 135                 140

Gly Gly Gly Gly Ser Gly Gly Gly Ser Gln Ile Val Leu Thr Gln
145                 150                 155                 160

Ser Pro Ala Ile Met Ser Ala Ser Pro Gly Glu Lys Val Thr Ile Thr
                165                 170                 175

Cys Ser Ala Ser Ser Ser Val Thr Tyr Met His Trp Phe Gln Gln Lys
                180                 185                 190

Pro Gly Thr Ser Pro Lys Leu Trp Ile Tyr Ser Thr Ser Asn Leu Ala
                195                 200                 205

Ser Gly Val Pro Ala Arg Phe Ser Gly Ser Gly Ser Gly Thr Ser Tyr
210                 215                 220

Ser Leu Thr Ile Ser Arg Met Glu Ala Glu Asp Ala Ala Thr Tyr Tyr
225                 230                 235                 240

Cys Gln Gln Arg Ser Thr Tyr Pro Leu Thr Phe Gly Ala Gly Thr Lys
                245                 250                 255

Leu Glu Ile Lys Arg Gly Gly Gly Ser Gly Gly Gly Gly Ser Gly
                260                 265                 270

Gly Gly Ser Gln Lys Arg Asp Asn Val Leu Phe Gln Ala Ala Thr
        275                 280                 285

Asp Glu Gln Pro Ala Val Ile Lys Thr Leu Glu Lys Leu Val Asn Ile
290                 295                 300

Glu Thr Gly Thr Gly Asp Ala Glu Gly Ile Ala Ala Gly Asn Phe
305                 310                 315                 320

Leu Glu Ala Glu Leu Lys Asn Leu Gly Phe Thr Val Thr Arg Ser Lys
                325                 330                 335

Ser Ala Gly Leu Val Val Gly Asp Asn Ile Val Gly Lys Ile Lys Gly
                340                 345                 350

Arg Gly Gly Lys Asn Leu Leu Leu Met Ser His Met Asp Thr Val Tyr
                355                 360                 365

Leu Lys Gly Ile Leu Ala Lys Ala Pro Phe Arg Val Glu Gly Asp Lys
370                 375                 380

Ala Tyr Gly Pro Gly Ile Ala Asp Asp Lys Gly Gly Asn Ala Val Ile
385                 390                 395                 400

Leu His Thr Leu Lys Leu Leu Lys Glu Tyr Gly Val Arg Asp Tyr Gly
                405                 410                 415

Thr Ile Thr Val Leu Phe Asn Thr Asp Glu Glu Lys Gly Ser Phe Gly
                420                 425                 430

Ser Arg Asp Leu Ile Gln Glu Glu Ala Lys Leu Ala Asp Tyr Val Leu
                435                 440                 445

Ser Phe Glu Pro Thr Ser Ala Gly Asp Glu Lys Leu Ser Leu Gly Thr
450                 455                 460

Ser Gly Ile Ala Tyr Val Gln Val Gln Ile Thr Gly Lys Ala Ser His
465                 470                 475                 480

Ala Gly Ala Ala Pro Glu Leu Gly Val Asn Ala Leu Val Glu Ala Ser
                485                 490                 495

Asp Leu Val Leu Arg Thr Met Asn Ile Asp Asp Lys Ala Lys Asn Leu
                500                 505                 510

Arg Phe Gln Trp Thr Ile Ala Lys Ala Gly Gln Val Ser Asn Ile Ile
                515                 520                 525
```

```
Pro Ala Ser Ala Thr Leu Asn Ala Asp Val Arg Tyr Ala Arg Asn Glu
            530                 535                 540

Asp Phe Asp Ala Ala Met Lys Thr Leu Glu Glu Arg Ala Gln Gln Lys
545                 550                 555                 560

Lys Leu Pro Glu Ala Asp Val Lys Val Ile Val Thr Arg Gly Arg Pro
                565                 570                 575

Ala Phe Asn Ala Gly Glu Gly Gly Lys Lys Leu Val Asp Lys Ala Val
            580                 585                 590

Ala Tyr Tyr Lys Glu Ala Gly Gly Thr Leu Gly Val Glu Glu Arg Thr
        595                 600                 605

Gly Gly Gly Thr Asp Ala Ala Tyr Ala Ala Leu Ser Gly Lys Pro Val
            610                 615                 620

Ile Glu Ser Leu Gly Leu Pro Gly Phe Gly Tyr His Ser Asp Lys Ala
625                 630                 635                 640

Glu Tyr Val Asp Ile Ser Ala Ile Pro Arg Arg Leu Tyr Met Ala Ala
                645                 650                 655

Arg Leu Ile Met Asp Leu Gly Ala Gly Lys
                660                 665
```

(2) INFORMATION FOR SEQ ID NO: 52:

(i) SEQUENCE CHARACTERISTICS:
        (A) LENGTH: 3217 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 52:

```
GAATTCGCCG CCACTATGGA TTTTCAAGTG CAGATTTTCA GCTTCCTGCT AATCAGTGCT    60

TCAGTCATAA TGTCCAGAGG ACAAACTGTT CTCTCCCAGT CTCCAGCAAT CCTGTCTGCA   120

TCTCCAGGGG AGAAGGTCAC AATGACTTGC AGGGCCAGCT CAAGTGTAAC TTACATTCAC   180

TGGTACCAGC AGAAGCCAGG TTCCTCCCCC AAATCCTGGA TTTATGCCAC ATCCAACCTG   240

GCTTCTGGAG TCCCTGCTCG CTTCAGTGGC AGTGGGTCTG GGACCTCTTA CTCTCTCACA   300

ATCAGCAGAG TGGAGGCTGA AGATGCTGCC ACTTATTACT GCCAACATTG GAGTAGTAAA   360

CCACCGACGT TCGGTGGAGG CACCAAGCTC GAGATCAAAC GGACTGTGGC TGCACCATCT   420

GTCTTCATCT TCCCGCCATC TGATGAGCAG TTGAAATCTG GAACTGCCTC TGTTGTGTGC   480

CTGCTGAATA ACTTCTATCC CAGAGAGGCC AAAGTACAGT GGAAGGTGGA TAACGCCCTC   540

CAATCGGGTA ACTCCCAGGA GAGTGTCACA GAGCAGGACA GCAAGGACAG CACCTACAGC   600

CTCAGCAGCA CCCTGACGCT GAGCAAAGCA GACTACGAGA AACACAAAGT CTACGCCTGC   660

GAAGTCACCC ATCAGGGCCT GAGTTCGCCC GTCACAAAGA GCTTCAACAG GGGAGAGTGT   720

TAATAGGAGC TCGGATCCAG ATCTGAGCTC CTGTAGACGT CGACATTAAT TCCGGTTATT   780

TTCCACCATA TTGCCGTCTT TTGGCAATGT GAGGGCCCGG AAACCTGGCC CTGTCTTCTT   840

GACGAGCATT CCTAGGGGTC TTTCCCCTCT CGCCAAAGGA ATGCAAGGTC TGTTGAATGT   900

CGTGAAGGAA GCAGTTCCTC TGGAAGCTTC TTGAAGACAA CAACGTCTG TAGCGACCCT   960

TTGCAGGCAG CGGAACCCCC CACCTGGCGA CAGGTGCCTC TGCGGCCAAA AGCCACGTGT  1020

ATAAGATACA CCTGCAAAGG CGGCACAACC CCAGTGCCAC GTTGTGAGTT GGATAGTTGT  1080

GGAAAGAGTC AAATGGCTCT CCTCAAGCGT ATTCAACAAG GGGCTGAAGG ATGCCCAGAA  1140

GGTACCCCAT TGTATGGGAT CTGATCTGGG GCCTCGGTGC ACATGCTTTA CATGTGTTTA  1200
```

-continued

```
GTCGAGGTTA AAAAACGTCT AGGCCCCCCG AACCACGGGG ACGTGGTTTT CCTTTGAAAA    1260

ACACGATGAT AATACCATGG AGTTGTGGCT GAACTGGATT TTCCTTGTAA CACTTTTAAA    1320

TGGTATCCAG TGTGAGGTGA AGCTGGTGGA GTCTGGAGGA GGCTTGGTAC AGCCTGGGGG    1380

TTCTCTGAGA CTCTCCTGTG CAACTTCTGG GTTCACCTTC ACTGATTACT ACATGAACTG    1440

GGTCCGCCAG CCTCCAGGAA AGGCACTTGA GTGGTTGGGT TTTATTGGAA ACAAAGCTAA    1500

TGGTTACACA ACAGAGTACA GTGCATCTGT GAAGGGTCGG TTCACCATCT CCAGAGATAA    1560

ATCCCAAAGC ATCCTCTATC TTCAAATGAA CACCCTGAGA GCTGAGGACA GTGCCACTTA    1620

TTACTGTACA AGAGATAGGG GGCTACGGTT CTACTTTGAC TACTGGGGCC AAGGCACCAC    1680

TCTCACAGTG AGCTCGGCTA GCACCAAGGG ACCATCGGTC TTCCCCCTGG CCCCCTGCTC    1740

CAGGAGCACC TCCGAGAGCA CAGCCGCCCT GGGCTGCCTG GTCAAGGACT ACTTCCCCGA    1800

ACCGGTGACG GTGTCGTGGA ACTCAGGCGC TCTGACCAGC GGCGTGCACA CCTTCCCGGC    1860

TGTCCTACAG TCCTCAGGAC TCTACTCCCT CAGCAGCGTC GTGACGGTGC CCTCCAGCAA    1920

CTTCGGCACC CAGACCTACA CCTGCAACGT AGATCACAAG CCCAGCAACA CCAAGGTGGA    1980

CAAGACAGTT GGCGGTGGTG GCTCTGGTGG TGGCGGTAGC GGTGGCGGGG GTTCCCAGAA    2040

GCGCGACAAC GTGCTGTTCC AGGCAGCTAC CGACGAGCAG CCGGCCGTGA TCAAGACGCT    2100

GGAGAAGCTG GTCAACATCG AGACCGGCAC CGGTGACGCC GAGGGCATCG CCGCTGCGGG    2160

CAACTTCCTC GAGGCCGAGC TCAAGAACCT CGGCTTCACG GTCACGCGAA GCAAGTCGGC    2220

CGGCCTGGTG GTGGGCGACA ACATCGTGGG CAAGATCAAG GGCCGCGGCG GCAAGAACCT    2280

GCTGCTGATG TCGCACATGG ACACCGTCTA CCTCAAGGGC ATTCTCGCGA AGGCCCCGTT    2340

CCGCGTCGAA GGCGACAAGG CCTACGGCCC GGGCATCGCC GACGACAAGG GCGGCAACGC    2400

GGTCATCCTG CACACGCTCA AGCTGCTGAA GGAATACGGC GTGCGCGACT ACGGCACCAT    2460

CACCGTGCTG TTCAACACCG ACGAGGAAAA GGGTTCCTTC GGCTCGCGCG ACCTGATCCA    2520

GGAAGAAGCC AAGCTGGCCG ACTACGTGCT CTCCTTCGAG CCCACCAGCG CAGGCGACGA    2580

AAAACTCTCG CTGGGCACCT CGGGCATCGC CTACGTGCAG GTCCAGATCA CCGGCAAGGC    2640

CTCGCATGCC GGCGCCGCGC CCGAGCTGGG CGTGAACGCG CTGGTCGAGG CTTCCGACCT    2700

CGTGCTGCGC ACGATGAACA TCGACGACAA GGCGAAGAAC CTGCGCTTCC AGTGGACCAT    2760

CGCCAAGGCC GGCCAGGTCT CGAACATCAT CCCCGCCAGC GCCACGCTGA ACGCCGACGT    2820

GCGCTACGCG CGCAACGAGG ACTTCGACGC CGCCATGAAG ACGCTGGAAG AGCGCGCGCA    2880

GCAGAAGAAG CTGCCCGAGG CCGACGTGAA GGTGATCGTC ACGCGCGGCC GCCCGGCCTT    2940

CAATGCCGGC GAAGGCGGCA AGAAGCTGGT CGACAAGGCG GTGGCCTACT ACAAGGAAGC    3000

CGGCGGCACG CTGGGCGTGG AAGAGCGCAC CGGCGGCGGC ACCGACGCGG CCTACGCCGC    3060

GCTCTCAGGC AAGCCAGTGA TCGAGAGCCT GGGCCTGCCG GCTTCGGCT ACCACAGCGA    3120

CAAGGCCGAG TACGTGGACA TCAGCGCGAT TCCGCGCCGC CTGTACATGG CTGCGCGCCT    3180

GATCATGGAT CTGGGCGCCG GCAAGTGATA ATCTAGA                            3217
```

(2) INFORMATION FOR SEQ ID NO: 53:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 53:

TGGATCTGAA GCTTAAACTA ACTCCATGGT GACCC                                35

(2) INFORMATION FOR SEQ ID NO: 54:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 54:

GCCACGGATC CCGCCACCTC CGGAGCCACC ACCGCCACAA TCCCTGGGCA CAATTTTCTT      60

G                                                                    61

(2) INFORMATION FOR SEQ ID NO: 55:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 55:

GCCCAGGAAG CTTGGCGGTG GTGGCTCCGG AGGTGGCGGT AGCGGTGGCG GGGGTTCCCA      60

GAAGCGCGAC AACGTGCTGT TCCAGGCAGC TACC                                 94

(2) INFORMATION FOR SEQ ID NO: 56:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 56:

ATGTGCGAAT TCAGCAGCAG GTTCTTGCCG CCGCGGCCCT TGATCTTGCC C              51

(2) INFORMATION FOR SEQ ID NO: 57:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:16..720

(xi) SEQUENCE DESCRIPTION: SEQ ID NO: 57:

```
GAATTCGCCG CCACC ATG GAT TTT CAA GTG CAG ATT TTC AGC TTC CTG CTA      51
                Met Asp Phe Gln Val Gln Ile Phe Ser Phe Leu Leu
                 1               5                  10

ATC AGT GCT TCA GTC ATA ATG TCC AGA GGA CAA ACT GTT CTC TCC CAG       99
Ile Ser Ala Ser Val Ile Met Ser Arg Gly Gln Thr Val Leu Ser Gln
     15                  20                  25
```

```
TCT CCA GCA ATC CTG TCT GCA TCT CCA GGG GAG AAG GTC ACA ATG ACT      147
Ser Pro Ala Ile Leu Ser Ala Ser Pro Gly Glu Lys Val Thr Met Thr
         30                  35                  40

TGC AGG GCC AGC TCA AGT GTA ACT TAC ATT CAC TGG TAC CAG CAG AAG      195
Cys Arg Ala Ser Ser Ser Val Thr Tyr Ile His Trp Tyr Gln Gln Lys
 45                  50                  55                  60

CCA GGT TCC TCC CCC AAA TCC TGG ATT TAT GCC ACA TCC AAC CTG GCT      243
Pro Gly Ser Ser Pro Lys Ser Trp Ile Tyr Ala Thr Ser Asn Leu Ala
                 65                  70                  75

TCT GGA GTC CCT GCT CGC TTC AGT GGC AGT GGG TCT GGG ACC TCT TAC      291
Ser Gly Val Pro Ala Arg Phe Ser Gly Ser Gly Ser Gly Thr Ser Tyr
             80                  85                  90

TCT CTC ACA ATC AGC AGA GTG GAG GCT GAA GAT GCT GCC ACT TAT TAC      339
Ser Leu Thr Ile Ser Arg Val Glu Ala Glu Asp Ala Ala Thr Tyr Tyr
         95                 100                 105

TGC CAA CAT TGG AGT AGT AAA CCA CCG ACG TTC GGT GGA GGC ACC AAG      387
Cys Gln His Trp Ser Ser Lys Pro Pro Thr Phe Gly Gly Gly Thr Lys
        110                 115                 120

CTG GAA ATC AAA CGG GCT GAT GCT GCA CCA ACT GTA TCC ATC TTC CCA      435
Leu Glu Ile Lys Arg Ala Asp Ala Ala Pro Thr Val Ser Ile Phe Pro
125                 130                 135                 140

CCA TCC AGT GAG CAG TTA ACA TCT GGA GGT GCC TCA GTC GTG TGC TTC      483
Pro Ser Ser Glu Gln Leu Thr Ser Gly Gly Ala Ser Val Val Cys Phe
                145                 150                 155

TTG AAC AAC TTC TAC CCC AAA GAC ATC AAT GTC AAG TGG AAG ATT GAT      531
Leu Asn Asn Phe Tyr Pro Lys Asp Ile Asn Val Lys Trp Lys Ile Asp
            160                 165                 170

GGC AGT GAA CGA CAA AAT GGC GTC CTG AAC AGT TGG ACT GAT CAG GAC      579
Gly Ser Glu Arg Gln Asn Gly Val Leu Asn Ser Trp Thr Asp Gln Asp
        175                 180                 185

AGC AAA GAC AGC ACC TAC AGC ATG AGC AGC ACC CTC ACG TTG ACC AAG      627
Ser Lys Asp Ser Thr Tyr Ser Met Ser Ser Thr Leu Thr Leu Thr Lys
190                 195                 200

GAC GAG TAT GAA CGA CAT AAC AGC TAT ACC TGT GAG GCC ACT CAC AAG      675
Asp Glu Tyr Glu Arg His Asn Ser Tyr Thr Cys Glu Ala Thr His Lys
205                 210                 215                 220

ACA TCA ACT TCA CCC ATT GTC AAG AGC TTC AAC AGG AAT GAG TGT          720
Thr Ser Thr Ser Pro Ile Val Lys Ser Phe Asn Arg Asn Glu Cys
                225                 230                 235

TAATAAGAAT TC                                                        732
```

(2) INFORMATION FOR SEQ ID NO: 58:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO: 58:

```
Met Asp Phe Gln Val Gln Ile Phe Ser Phe Leu Leu Ile Ser Ala Ser
 1               5                  10                  15

Val Ile Met Ser Arg Gly Gln Thr Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Thr Tyr Ile His Trp Tyr Gln Gln Lys Pro Gly Ser Ser
    50                  55                  60
```

-continued

```
Pro Lys Ser Trp Ile Tyr Ala Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln His Trp
            100                 105                 110

Ser Ser Lys Pro Pro Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
210                 215                 220

Pro Ile Val Lys Ser Phe Asn Arg Asn Glu Cys
225                 230                 235
```

(2) INFORMATION FOR SEQ ID NO: 59:

(i) SEQUENCE CHARACTERISTICS:
        (A) LENGTH: 1974 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION:16..1956

(xi) SEQUENCE DESCRIPTION: SEQ ID NO: 59:

```
AAGCTTGCCG CCACC ATG AAG TTG TGG CTG AAC TGG ATT TTC CTT GTA ACA      51
                 Met Lys Leu Trp Leu Asn Trp Ile Phe Leu Val Thr
                  1               5                  10

CTT TTA AAT GGT ATC CAG TGT GAG GTG AAG CTG GTG GAG TCT GGA GGA       99
Leu Leu Asn Gly Ile Gln Cys Glu Val Lys Leu Val Glu Ser Gly Gly
         15                  20                  25

GGC TTG GTA CAG CCT GGG GGT TCT CTG AGA CTC TCC TGT GCA ACT TCT      147
Gly Leu Val Gln Pro Gly Gly Ser Leu Arg Leu Ser Cys Ala Thr Ser
 30                  35                  40

GGG TTC ACC TTC ACT GAT TAC TAC ATG AAC TGG GTC CGC CAG CCT CCA      195
Gly Phe Thr Phe Thr Asp Tyr Tyr Met Asn Trp Val Arg Gln Pro Pro
 45                  50                  55                  60

GGA AAG GCA CTT GAG TGG TTG GGT TTT ATT GGA AAC AAA GCT AAT GGT      243
Gly Lys Ala Leu Glu Trp Leu Gly Phe Ile Gly Asn Lys Ala Asn Gly
                 65                  70                  75

TAC ACA ACA GAG TAC AGT GCA TCT GTG AAG GGT CGG TTC ACC ATC TCC      291
Tyr Thr Thr Glu Tyr Ser Ala Ser Val Lys Gly Arg Phe Thr Ile Ser
             80                  85                  90

AGA GAT AAA TCC CAA AGC ATC CTC TAT CTT CAA ATG AAC ACC CTG AGA      339
Arg Asp Lys Ser Gln Ser Ile Leu Tyr Leu Gln Met Asn Thr Leu Arg
         95                 100                 105
```

-continued

```
GCT GAG GAC AGT GCC ACT TAT TAC TGT ACA AGA GAT AGG GGG CTA CGG      387
Ala Glu Asp Ser Ala Thr Tyr Tyr Cys Thr Arg Asp Arg Gly Leu Arg
        110                 115                 120

TTC TAC TTT GAC TAC TGG GGC CAA GGC ACC ACT CTC ACA GTC TCC TCA      435
Phe Tyr Phe Asp Tyr Trp Gly Gln Gly Thr Thr Leu Thr Val Ser Ser
125                 130                 135                 140

GCC AAA ACG ACA CCC CCA TCT GTC TAT CCA CTG GCC CCT GGA TCT GCT      483
Ala Lys Thr Thr Pro Pro Ser Val Tyr Pro Leu Ala Pro Gly Ser Ala
                145                 150                 155

GCC CAA ACT AAC TCC ATG GTG ACC CTG GGA TGC CTG GTC AAG GGC TAT      531
Ala Gln Thr Asn Ser Met Val Thr Leu Gly Cys Leu Val Lys Gly Tyr
        160                 165                 170

TTC CCT GAG CCA GTG ACA GTG ACC TGG AAC TCT GGA TCT CTG TCC AGC      579
Phe Pro Glu Pro Val Thr Val Thr Trp Asn Ser Gly Ser Leu Ser Ser
        175                 180                 185

GGT GTG CAC ACC TTC CCA GCT GTC CTG CAG TCT GAC CTC TAC ACT CTG      627
Gly Val His Thr Phe Pro Ala Val Leu Gln Ser Asp Leu Tyr Thr Leu
        190                 195                 200

AGC AGC TCA GTG ACT GTC CCC TCC AGC ACC TGG CCC AGC GAG ACC GTC      675
Ser Ser Ser Val Thr Val Pro Ser Ser Thr Trp Pro Ser Glu Thr Val
205                 210                 215                 220

ACC TGC AAC GTT GCC CAC CCG GCC AGC AGC ACC AAG GTG GAC AAG AAA      723
Thr Cys Asn Val Ala His Pro Ala Ser Ser Thr Lys Val Asp Lys Lys
                225                 230                 235

ATT GTG CCC AGG GAT TGT GGC GGT GGT GGC TCC GGA GGT GGC GGT AGC      771
Ile Val Pro Arg Asp Cys Gly Gly Gly Gly Ser Gly Gly Gly Gly Ser
            240                 245                 250

GGT GGC GGG GGT TCC CAG AAG CGC GAC AAC GTG CTG TTC CAG GCA GCT      819
Gly Gly Gly Gly Ser Gln Lys Arg Asp Asn Val Leu Phe Gln Ala Ala
        255                 260                 265

ACC GAC GAG CAG CCG GCC GTG ATC AAG ACG CTG GAG AAG CTG GTC AAC      867
Thr Asp Glu Gln Pro Ala Val Ile Lys Thr Leu Glu Lys Leu Val Asn
270                 275                 280

ATC GAG ACC GGC ACC GGT GAC GCC GAG GGC ATC GCC GCT GCG GGC AAC      915
Ile Glu Thr Gly Thr Gly Asp Ala Glu Gly Ile Ala Ala Ala Gly Asn
285                 290                 295                 300

TTC CTC GAG GCC GAG CTC AAG AAC CTC GGC TTC ACG GTC ACG CGA AGC      963
Phe Leu Glu Ala Glu Leu Lys Asn Leu Gly Phe Thr Val Thr Arg Ser
                305                 310                 315

AAG TCG GCC GGC CTG GTG GTG GGC GAC AAC ATC GTG GGC AAG ATC AAG     1011
Lys Ser Ala Gly Leu Val Val Gly Asp Asn Ile Val Gly Lys Ile Lys
            320                 325                 330

GGC CGC GGC GGC AAG AAC CTG CTG CTG ATG TCG CAC ATG GAC ACC GTC     1059
Gly Arg Gly Gly Lys Asn Leu Leu Leu Met Ser His Met Asp Thr Val
        335                 340                 345

TAC CTC AAG GGC ATT CTC GCG AAG GCC CCG TTC CGC GTC GAA GGC GAC     1107
Tyr Leu Lys Gly Ile Leu Ala Lys Ala Pro Phe Arg Val Glu Gly Asp
350                 355                 360

AAG GCC TAC GGC CCG GGC ATC GCC GAC GAC AAG GGC GGC AAC GCG GTC     1155
Lys Ala Tyr Gly Pro Gly Ile Ala Asp Asp Lys Gly Gly Asn Ala Val
365                 370                 375                 380

ATC CTG CAC ACG CTC AAG CTG CTG AAG GAA TAC GGC GTG CGC GAC TAC     1203
Ile Leu His Thr Leu Lys Leu Leu Lys Glu Tyr Gly Val Arg Asp Tyr
                385                 390                 395

GGC ACC ATC ACC GTG CTG TTC AAC ACC GAC GAG GAA AAG GGT TCC TTC     1251
Gly Thr Ile Thr Val Leu Phe Asn Thr Asp Glu Glu Lys Gly Ser Phe
            400                 405                 410

GGC TCG CGC GAC CTG ATC CAG GAA GAA GCC AAG CTG GCC GAC TAC GTG     1299
Gly Ser Arg Asp Leu Ile Gln Glu Glu Ala Lys Leu Ala Asp Tyr Val
        415                 420                 425
```

```
CTC TCC TTC GAG CCC ACC AGC GCA GGC GAC GAA AAA CTC TCG CTG GGC        1347
Leu Ser Phe Glu Pro Thr Ser Ala Gly Asp Glu Lys Leu Ser Leu Gly
        430                 435                 440

ACC TCG GGC ATC GCC TAC GTG CAG GTC AAC ATC ACC GGC AAG GCC TCG        1395
Thr Ser Gly Ile Ala Tyr Val Gln Val Asn Ile Thr Gly Lys Ala Ser
445                 450                 455                 460

CAT GCC GGC GCC GCG CCC GAG CTG GGC GTG AAC GCG CTG GTC GAG GCT        1443
His Ala Gly Ala Ala Pro Glu Leu Gly Val Asn Ala Leu Val Glu Ala
                465                 470                 475

TCC GAC CTC GTG CTG CGC ACG ATG AAC ATC GAC GAC AAG GCG AAG AAC        1491
Ser Asp Leu Val Leu Arg Thr Met Asn Ile Asp Asp Lys Ala Lys Asn
        480                 485                 490

CTG CGC TTC AAC TGG ACC ATC GCC AAG GCC GGC AAC GTC TCG AAC ATC        1539
Leu Arg Phe Asn Trp Thr Ile Ala Lys Ala Gly Asn Val Ser Asn Ile
        495                 500                 505

ATC CCC GCC AGC GCC ACG CTG AAC GCC GAC GTG CGC TAC GCG CGC AAC        1587
Ile Pro Ala Ser Ala Thr Leu Asn Ala Asp Val Arg Tyr Ala Arg Asn
510                 515                 520

GAG GAC TTC GAC GCC GCC ATG AAG ACG CTG GAA GAG CGC GCG CAG CAG        1635
Glu Asp Phe Asp Ala Ala Met Lys Thr Leu Glu Glu Arg Ala Gln Gln
525                 530                 535                 540

AAG AAG CTG CCC GAG GCC GAC GTG AAG GTG ATC GTC ACG CGC GGC CGC        1683
Lys Lys Leu Pro Glu Ala Asp Val Lys Val Ile Val Thr Arg Gly Arg
                545                 550                 555

CCG GCC TTC AAT GCC GGC GAA GGC GGC AAG AAG CTG GTC GAC AAG GCG        1731
Pro Ala Phe Asn Ala Gly Glu Gly Gly Lys Lys Leu Val Asp Lys Ala
                560                 565                 570

GTG GCC TAC TAC AAG GAA GCC GGC GGC ACG CTG GGC GTG GAA GAG CGC        1779
Val Ala Tyr Tyr Lys Glu Ala Gly Gly Thr Leu Gly Val Glu Glu Arg
                575                 580                 585

ACC GGC GGC GGC ACC GAC GCG GCC TAC GCC GCG CTC TCA GGC AAG CCA        1827
Thr Gly Gly Gly Thr Asp Ala Ala Tyr Ala Ala Leu Ser Gly Lys Pro
590                 595                 600

GTG ATC GAG AGC CTG GGC CTG CCG GGC TTC GGC TAC CAC AGC GAC AAG        1875
Val Ile Glu Ser Leu Gly Leu Pro Gly Phe Gly Tyr His Ser Asp Lys
605                 610                 615                 620

GCC GAG TAC GTG GAC ATC AGC GCG ATT CCG CGC CGC CTG TAC ATG GCT        1923
Ala Glu Tyr Val Asp Ile Ser Ala Ile Pro Arg Arg Leu Tyr Met Ala
                625                 630                 635

GCG CGC CTG ATC ATG GAT CTG GGC GCC GGC AAG TGATAAGAAT TCCTCGAG        1974
Ala Arg Leu Ile Met Asp Leu Gly Ala Gly Lys
                640                 645
```

(2) INFORMATION FOR SEQ ID NO: 60:

(i) SEQUENCE CHARACTERISTICS:
        (A) LENGTH: 647 amino acids
        (B) TYPE: amino acid
        (D) TOPOLOGY: linear (ii) MOLECULE TYPE: protein (xi) SEQUENCE DESCRIPTION: SEQ ID NO: 60:

```
Met Lys Leu Trp Leu Asn Trp Ile Phe Leu Val Thr Leu Leu Asn Gly
  1               5                  10                  15

Ile Gln Cys Glu Val Lys Leu Val Glu Ser Gly Gly Gly Leu Val Gln
                 20                  25                  30

Pro Gly Gly Ser Leu Arg Leu Ser Cys Ala Thr Ser Gly Phe Thr Phe
             35                  40                  45

Thr Asp Tyr Tyr Met Asn Trp Val Arg Gln Pro Pro Gly Lys Ala Leu
         50                  55                  60
```

-continued

```
Glu Trp Leu Gly Phe Ile Gly Asn Lys Ala Asn Gly Tyr Thr Thr Glu
 65                  70                  75                  80

Tyr Ser Ala Ser Val Lys Gly Arg Phe Thr Ile Ser Arg Asp Lys Ser
                 85                  90                  95

Gln Ser Ile Leu Tyr Leu Gln Met Asn Thr Leu Arg Ala Glu Asp Ser
            100                 105                 110

Ala Thr Tyr Tyr Cys Thr Arg Asp Arg Gly Leu Arg Phe Tyr Phe Asp
        115                 120                 125

Tyr Trp Gly Gln Gly Thr Thr Leu Thr Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Gly Gly Gly Ser Gly Gly Gly Gly Ser Gly Gly Gly Gly
                245                 250                 255

Ser Gln Lys Arg Asp Asn Val Leu Phe Gln Ala Ala Thr Asp Glu Gln
            260                 265                 270

Pro Ala Val Ile Lys Thr Leu Glu Lys Leu Val Asn Ile Glu Thr Gly
        275                 280                 285

Thr Gly Asp Ala Glu Gly Ile Ala Ala Gly Asn Phe Leu Glu Ala
290                 295                 300

Glu Leu Lys Asn Leu Gly Phe Thr Val Thr Arg Ser Lys Ser Ala Gly
305                 310                 315                 320

Leu Val Val Gly Asp Asn Ile Val Gly Lys Ile Lys Gly Arg Gly Gly
                325                 330                 335

Lys Asn Leu Leu Leu Met Ser His Met Asp Thr Val Tyr Leu Lys Gly
            340                 345                 350

Ile Leu Ala Lys Ala Pro Phe Arg Val Glu Gly Asp Lys Ala Tyr Gly
        355                 360                 365

Pro Gly Ile Ala Asp Asp Lys Gly Gly Asn Ala Val Ile Leu His Thr
370                 375                 380

Leu Lys Leu Leu Lys Glu Tyr Gly Val Arg Asp Tyr Gly Thr Ile Thr
385                 390                 395                 400

Val Leu Phe Asn Thr Asp Glu Glu Lys Gly Ser Phe Gly Ser Arg Asp
                405                 410                 415

Leu Ile Gln Glu Glu Ala Lys Leu Ala Asp Tyr Val Leu Ser Phe Glu
            420                 425                 430

Pro Thr Ser Ala Gly Asp Glu Lys Leu Ser Leu Gly Thr Ser Gly Ile
        435                 440                 445

Ala Tyr Val Gln Val Asn Ile Thr Gly Lys Ala Ser His Ala Gly Ala
    450                 455                 460

Ala Pro Glu Leu Gly Val Asn Ala Leu Val Glu Ala Ser Asp Leu Val
465                 470                 475                 480
```

```
                                    -continued

Leu Arg Thr Met Asn Ile Asp Asp Lys Ala Lys Asn Leu Arg Phe Asn
                485                 490                 495

Trp Thr Ile Ala Lys Ala Gly Asn Val Ser Asn Ile Ile Pro Ala Ser
            500                 505                 510

Ala Thr Leu Asn Ala Asp Val Arg Tyr Ala Arg Asn Glu Asp Phe Asp
            515                 520                 525

Ala Ala Met Lys Thr Leu Glu Glu Arg Ala Gln Gln Lys Lys Leu Pro
        530                 535                 540

Glu Ala Asp Val Lys Val Ile Val Thr Arg Gly Arg Pro Ala Phe Asn
545                 550                 555                 560

Ala Gly Glu Gly Gly Lys Lys Leu Val Asp Lys Ala Val Ala Tyr Tyr
                565                 570                 575

Lys Glu Ala Gly Gly Thr Leu Gly Val Glu Glu Arg Thr Gly Gly Gly
            580                 585                 590

Thr Asp Ala Ala Tyr Ala Ala Leu Ser Gly Lys Pro Val Ile Glu Ser
            595                 600                 605

Leu Gly Leu Pro Gly Phe Gly Tyr His Ser Asp Lys Ala Glu Tyr Val
        610                 615                 620

Asp Ile Ser Ala Ile Pro Arg Arg Leu Tyr Met Ala Ala Arg Leu Ile
625                 630                 635                 640

Met Asp Leu Gly Ala Gly Lys
                645
```

GENE CONSTRUCT ENCODING A HETEROLOGOUS PRODRUG-ACTIVATING ENZYME AND A CELL TARGETING MOIETY

This application is a national stage application filed under 35 U.S.C. 371 of International Patent Appln. No. PCT/GB98/01294, filed May 5, 1998.

This invention relates particularly to gene directed enzyme prodrug therapy (GDEPT) using in situ antibody generation to provide enhanced selectivity, particularly for use in cancer therapy.

Known gene therapy based prodrug therapeutic approaches include virus-directed enzyme prodrug therapy (VDEPT) and gene-directed enzyme prodrug therapy (GDEPT), the latter term encompassing both VDEPT and non-viral delivery systems. VDEPT involves targeting tumour cells with a viral vector carrying a gene which codes for an enzyme capable of activating a prodrug. The viral vector enters the tumour cell and enzyme is expressed from the enzyme gene inside the cell. In GDEPT, alternative approaches such as microinjection, liposomal delivery and receptor mediated DNA uptake as well as viruses may be used to deliver the gene encoding the enzyme.

In both VDEPT and GDEPT the enzyme gene can be transcriptionally regulated by DNA sequences capable of being selectively activated in mammalian cells e.g. tumour cells (EP 415 731 (Wellcome); Huber et al, Proc. Natl. Acad. Sci. USA. 88, 8039–8043, 1991). While giving some degree of selectivity, gene expression may also occur in non-target cells and this is clearly undesirable when the approach is being used to activate prodrugs into potent cytotoxic agents. In addition these regulatory sequences will generally lead to reduced expression of the enzyme compared with using viral promoters and this will lead to a reduced ability to convert prodrug in the target tissue.

Expression and localisation of the prodrug activating enzyme inside the cell has disadvantages. Prodrug design is severely limited by the fact that the prodrug has to be able to cross the cell membrane and enter the cell but not be toxic until it is converted to the drug inside the cell by the activating enzyme. Most prodrugs utilise hydrophilic groups to prevent cell entry and thus reduce cytotoxicity. Prodrug turnover by activating enzyme produces a less hydrophilic drug which can enter cells to produce anti-cancer effects. This approach can not be used when the activating enzyme is expressed inside the cell. Another disadvantage is that target cells which lack intracellular activating enzyme will be difficult to attack because they are unable to generate active drug. To achieve this desirable "bystander activity" (or "neighbouring cell kill"), the active drug will have to be capable of diffusion out of the cell containing activating enzyme to reach target cells which lack enzyme expression. Many active drugs when produced inside a cell will be unable to escape from the cell to achieve this bystander effect.

Modifications of GDEPT have been put forward to overcome some of the problems described above. Firstly vectors have been described which are said to express the activating enzyme on the surface of the target cell (WO 96/03515) by attaching a signal peptide and transmembrane domain to the activating enzyme. The approach, if viable, would overcome the problems of having the activating enzyme located inside the cell but would still have to rely on transcriptionally regulated sequences capable of being selectively expressed in target cells to restrict cell expression. As described above there are disadvantages of using such sequences. Secondly vectors have been described which result in secretion of the enzyme from the target cell (WO 96/16179). In this approach the enzyme would be able to diffuse away from its site of generation since it is extracellular and not attached to the cell surface. Enzyme which has diffused away from the target site would be capable of activating prodrug at non-target sites leading to unwanted toxicity. To achieve some selectivity it is suggested that enzyme precursors could be used which are cleaved by pathology associated proteases to form active enzyme. Some selectivity is likely to be achieved by this approach but its unlikely that activation will only occur at target sites. In addition, once activated, the enzyme will still be free to diffuse away from the target site and thus suffer from the same drawback described above.

For GDEPT approaches, three levels of selectivity can be observed. Firstly, there is selectivity at the cell infection stage such that only specific cell types are targeted. For example cell selectivity can be provided by the gene delivery system per se. An example of this type of selectivity is set out in International Patent Application WO 95/26412 (UAB Research Foundation) which describes the use of modified adenovirus fiber proteins incorporating cell specific ligands. Other examples of cell specific targeting include ex vivo gene transfer to specific cell populations such as lymphocytes and direct injection of DNA into muscle tissue.

The second level of selectivity is control of gene expression after cell infection such as for example by the use of cell or tissue specific promoters. If the gene has been delivered to a cell type in a selective manner then it is important that a promoter is chosen that is compatible with activity in the cell type.

The third level of selectivity can be considered as the selectivity of the expressed gene construct. Selectivity at this level has received scant attention to date. In International patent application WO 96/16179 (Wellcome Foundation) it is suggested that enzyme precursors could be used which are cleaved by pathology associated proteases to form active enzyme. Some selectivity is likely to be achieved by this approach but it is unlikely that activation will only occur at target sites. In addition, once activated, the enzyme will still be free to diffuse away from the target site and thus suffer from the same drawback of activating prodrug at non-target sites leading to unwanted toxicity.

There exists a need for more selective GDEPT systems to reduce undesirable effects in normal tissues arising from erroneous prodrug activation.

The present invention is based on the discovery that antibody-heterologous enzyme gene constructs can be expressed intracellularly and used in GDEPT systems (or other systems such as AMIRACS—see below) for cell targeting arising from antibody specificity to deliver cell surface available enzyme in a selective manner. This approach may be used optionally in combination with any other suitable specificity enhancing technique(s) such as targeted cell infection and/or tissue specific expression.

According to one aspect of the present invention there is provided a gene construct encoding a cell targeting antibody and a heterologous enzyme for use as a medicament in a mammalian host wherein the gene construct is capable of expressing the antibody and enzyme as a conjugate within a target cell in the mammalian host and wherein the conjugate can leave the cell thereafter for selective localisation at a cell surface antigen recognised by the antibody.

According to another aspect of the present invention there is provided a gene construct encoding a cell targeting moiety and a heterologous prodrug activating enzyme for use as a medicament in a mammalian host wherein the gene construct is capable of expressing the cell targeting moiety and heterologous prodrug activating enzyme as a conjugate within a cell in the mammalian host and wherein the conjugate is directed to leave the cell thereafter for selective localisation at a cell surface antigen recognised by the cell targeting moiety.

The "cell targeting moiety" is defined as any polypeptide or fragment thereof which selectively binds to a particular cell type in a host through recognition of a cell surface antigen. Preferably the cell targeting moiety is an antibody. Cell targeting moieties other than antibodies include ligands as described for use in Ligand Directed Enzyme Prodrug Therapy as described in International patent application WO 97/26918, Cancer Research Campaign Technology Limited, such as for example epidermal growth factor, heregulin, c-erbB2 and vascular endothelial growth factor with the latter being preferred.

A "cell targeting antibody" is defined as an antibody or fragment thereof which selectively binds to a particular cell type in a host through recognition of a cell surface antigen. Preferred cell targeting antibodies are specific for solid tumours, more preferably colorectal tumours, more preferably an anti-CEA antibody, more preferably antibody A5B7 or 806.077 antibody with 806.077 antibody being especially preferred. Hybridoma 806.077 antibody was deposited at the European Collection of Animal Cell Cultures (ECACC), PHLS Centre for Applied Microbiology & Research, Porton Down, Salisbury, Wiltshire SP4 0JG, United Kingdom on Feb. 29, 1996 under accession no. 96022936 in accordance with the Budapest Treaty.

Antibody A5B7 binds to human carcinoembryonic antigen (CEA) and is particularly suitable for targeting colorectal carcinoma. A5B7 is available from DAKO Ltd., 16 Manor Courtyard, Hughenden Avenue, High Wycombe, Bucks HP13 5RE, England, United Kingdom. In general the antibody (or antibody fragment)—enzyme conjugate should be at least divalent, that is to say capable of binding to at least 2 tumour associated antigens (which may be the same or different). Antibody molecules may be humanised by known methods such as for example by "CDR grafting" as disclosed in EP239400 or by grafting complete variable regions from for example a murine antibody onto human constant regions ("chimaeric antibodies") as disclosed in U.S. Pat. No. 4,816,567. Humanised antibodies may be useful for reducing immunogenicity of an antibody (or antibody fragment). A humanised version of antibody A5B7 has been disclosed in International Patent Application WO 92/01059 (Celltech).

The hybridoma which produces monoclonal antibody A5B7 was deposited with the European Collection of Animal Cell Cultures, Division of Biologics, PHLS Centre for Applied Microbiology and Research, Porton Down, Salisbury, Wiltshire SP4 0JG, United Kingdom. The date of deposit was Jul. 14, 1993 and the accession number is No. 93071411. Antibody A5B7 may be obtained from the deposited hybridoma using standard techniques known in the art such as documented in Fenge C, Fraune E & Schuegerl K in "Production of Biologicals from Animal Cells in Culture" (Spier R E, Griffiths J R & Meignier B, eds) Butterworth-Heinemann, 1991, 262–265 and Anderson B L & Gruenberg M L in "Commercial Production of Monoclonal Antibodies" (Seaver S, ed), Marcel Dekker, 1987, 175–195. The cells may require re-cloning from time to time by limiting dilution in order to maintain good levels of antibody production.

A "heterologous enzyme" is defined as an enzyme for turning over a substrate that has been administered to the host and the enzyme is not naturally present in the relevant compartment of the host. The enzyme may be foreign to the mammalian host (e.g. a bacterial enzyme like CPG2) or it may not naturally occur within the relevant host compartment (e.g. the use of lysozyme as an ADEPT enzyme (for an explanation of ADEPT see below) is possible because lysozyme does not occur naturally in the circulation, see U.S. Pat. No. 5,433,955, Akzo Nev.). The relevant host compartment is that part of the mammalian host in which the substrate is distributed. Preferred enzymes are enzymes suitable for ADEPT or AMIRACS (Antimetabolite with Inactivation of Rescue Agents at Cancer Sites; see Bagshawe (1994) in Cell Biophysics 24/25, 83–91) but ADEPT enzymes are preferred. Antibody directed enzyme prodrug therapy (ADEPT) is a known cancer therapeutic approach. ADEPT uses a tumour selective antibody conjugated to an enzyme. The conjugate is administered to the patient (usually intravenously), allowed to localise at the tumour site(s) and clear from the blood and other normal tissues. A prodrug is then administered to the patient which is converted by the enzyme (localised at the tumour site) into a cytotoxic drug which kills the tumour cells.

In International Patent Application WO 96/20011, published Jul. 4, 1996, we proposed a "reversed polarity" ADEPT system based on mutant human enzymes having the advantage of low immnunogenicity compared with for example bacterial enzymes. A particular host enzyme was human pancreatic CPB (see for example, Example 15 [D253K]human CPB & 16 [D253R]human CPB therein) and prodrugs therefor (see Examples 18 & 19 therein). The host enzyme is mutated to give a change in mode of interaction between enzyme and prodrug in terms of recognition of substrate compared with the native host enzyme. In our subsequent International Patent Application No PCT/GB96/01975 (published Mar. 6, 1997 as WO 97/07796) further work on mutant CPB enzyme/prodrug combinations for ADEPT are described. Preferred enzymes suitable for ADEPT are any one of CPG2 or a reversed polarity CPB enzyme, for example any one of [D253K]HCPB, [G251T, D253K]HCPB or [A248S,G251T,D253K]HCPB. A preferred form of CPG2 is one in which the polypeptide glycosylation sites have been mutated so as to prevent or reduce glycosylation on expression in mammalian cells (see WO 96/03515, Cancer Research Campaign Technology); this gives improved enzyme activity. Further considerations arise for enzymes such as CPB which require a pro domain to facilitate correct folding; here the pro domain can either be expressed as a separately (in trans) or expressed as part of the fusion protein and subsequently removed.

Large scale purification of CPG2 from Pseudomonas RS-16 was described in Sherwood et al (1985), Eur, J. Biochem., 148, 447–453. CPG2 may be obtained from Centre for Applied Microbiology and Research, Porton Down, Salisbury, Wiltshire SP4 0JG, United Kingdom. CPG2 may also be obtained by recombinant techniques. The nucleotide coding sequence for CPG2 has been published by Minton, N. P. et al., Gene, 31 (1984), 31–38. Expression of the coding sequence has been reported in *E.coli* (Chambers, S. P. et al., Appl. Microbiol, Biotechnol. (1988), 29, 572–578) and in *Saccharomyces cerevisiae* (Clarke, L. E. et al., J. Gen Microbiol, (1985) 131, 897–904). Total gene synthesis has been described by M. Edwards in Am. Biotech. Lab (1987), 5, 38–44. Expression of heterologous proteins in *E.coli* has been reviewed by F. A. O. Marston in DNA Cloning Vol. III, Practical Approach Series, IRL Press (Editor D M Glover), 1987, 59–88. Expression of proteins in yeast has been reviewed in Methods in Enzymology Volume 194, Academic Press 1991, Edited by C. Guthrie and G R Fink.

Whilst cancer therapeutic approaches are preferred the invention may also be applied to other therapeutic areas as long as a target antigen can be selected and a suitable enzyme/prodrug combination prepared. For example, inflammatory diseases such as rheumatiod arthritis may be treated by for example using an antibody selective for synovial cells fused to an enzyme capable of converting an anti-inflammatory drug in the form of a prodrug into an anti-inflammatory drug. Use of antibodies to target rheumatoid arthritis disease has been described in Blakey et al, 1988, Scand. J. Rheumatology, Suppl. 76, 279–287.

A "conjugate" between antibody and enzyme can be a fusion protein (covalent linkage) or the conjugate can be formed by non-covalent binding between antibody and enzyme formed in situ. Preferably the conjugate is in the form of a fusion protein, more preferably the antibody component of the fusion is at least divalent (for improved binding avidity compared with monovalent antibody). Antibody constructs lacking an Fc portion are preferred, especially Fab or F(ab')$_2$ fragments. For CPG2 fusions (or fusions with any non-monomeric enzyme) special considerations apply because CPG2 is a dimeric enzyme and the antibody is preferably divalent thus there exists the potential for undesirable competing dimerisation between two molecular species. Therefore a preferred CPG2 fusion is one in which the fusion protein is formed through linking a C-terminus of an antibody Fab heavy chain (ie lacking a hinge region) to an N-terminus of a CPG2 molecule; two of these Fab-CPG2 molecules then dimerise through the CPG2 dimerisation domain to form a (Fab-CPG2)$_2$ conjugate. For antibody constructs with monomeric enzymes, F(ab')$_2$ fragments are preferred, especially F(ab')$_2$ fragments having a human IgG3 hinge region. Fusions between antibody and enzyme may optionally be effected through a short peptide linker such as for example (G$_4$S)$_3$. Preferred fusion constructs are those in which the enzyme is fused to the C terminus of the antibody, through the heavy or light chain thereof with fusion through the antibody heavy chain being preferred. Accordingly a preferred gene construct is a gene construct for use as a medicament as described herein in which the antibody-enzyme CPG2 conjugate is a fusion protein in which the enzyme is fused to the C terminus of the antibody through the heavy or light chain thereof whereby dimerisation of the encoded conjugate when expressed can take place through a dimerisation domain on CPG2. A more preferred gene construct is a gene construct for use as a medicament wherein the fusion protein is formed through linking a C-terminus of an antibody Fab heavy chain to an N-terminus of a CPG2 molecule to form a Fab-CPG2 whereby two Fab-CPG2 molecules when expressed dimerise through CPG2 to form a (Fab-CPG2)$_2$ conjugate. In another embodiment of the invention a preferred gene construct for use as a medicament is one wherein the carboxypeptidase is selected from [D253K]HCPB, [G251T, D253K]HCPB or [A248S,G251T,D253K]HCPB.

It is contemplated that should it be possible to obtain a natural multimeric enzyme in monomeric form whilst substantially retaining enzymic activity then the monomeric form of the enzyme could be used to form a conjugate of the invention. Similarly, it is contemplated that should it be possible to obtain a natural monomeric enzyme in multimeric form whilst substantially retaining enzymic activity then the multimeric form of the enzyme could be used to form a conjugate of the invention.

The conjugate is directed to leave the cell after expression therein through use of a secretory leader sequence which is cleaved as the conjugate passes through the cell membrane. Preferably the secretory leader is the secretory leader that occurs naturally with the antibody.

According to another aspect of the present invention there is provided use of a gene construct encoding a cell targeting antibody and a heterologous enzyme for use for manufacture of a medicament for cancer therapy in a mammalian host wherein the gene construct is capable of expressing the antibody and enzyme as a conjugate within a target cell in the mammalian host and wherein the conjugate can leave the cell thereafter for selective localisation at a cell surface antigen recognised by the antibody.

Any suitable delivery system may be applied to deliver the gene construct of the present invention including viral and non-viral systems. Viral systems include retroviral vectors, adenoviral vectors, adeno-associated virus, vaccinia, herpes simplex virus, HIV, the minute virus of mice, hepatitis B virus and influenza virus. Non-viral systems include uncomplexed DNA, DNA-liposome complexes, DNA-protein complexes and DNA-coated gold particles.

Retroviral vectors lack immunogenic proteins and there is no preexisting host immunity but are limited to infecting dividing cells. Retroviruses have been used in clinical trials (Rosenberg et al., N. Engl. J. Med., 1990, 323: 570–578). Retroviruses are composed of an RNA genome that is packaged in an envelope derived from host cell membrane and viral proteins. For gene expression, it must first reverse transcribe its positive-strand RNA genome into double-stranded DNA, which is then integrated into the host cell DNA using reverse transcriptase and integrase protein contained in the retrovirus particle. The integrated provirus is able to use host cell machinery for gene expression.

Murine leukemia virus is widely used (Miller et al., Methods Enzymol., 1993, 217: 581–599). Retroviral vectors are constructed by removal of the gag, pol and env genes to make room for the relevant payload and to eliminate the replicative functions of the virus. Virally encoded mRNAs are eliminated and this removes any potential immune response to the transduced cells. Genes encoding antibiotic resistance often are included as a means of selection. Promoter and enhancer functions also may be included for example to provide for tissue-specific expression after administration in vivo. Promoter and enhancer functions contained in the long terminal repeat may also be used.

These viruses can be produced only in viral packaging cell lines. The packaging cell line may be constructed by stably inserting the deleted viral genes (gag, pol. and env) into the cell such that they reside on different chromosomes to prevent recombination. The packaging cell line is used to construct a producer cell line that will generate replication-defective retrovirus containing the relevant payload gene by inserting the recombinant proviral DNA. Plasmid DNA containing the long terminal repeat sequences flanking a small portion of the gag gene that contains the encapsidation sequence and the genes of interest is transfected into the packaging cell line using standard techniques for DNA transfer and uptake (electroporation, calcium precipitation, etc.). Variants of this approach have been employed to decrease the likelihood of production of replication-competent virus (Jolly, D., Cancer Gene Therapy, 1994, 1, 51–64). The host cell range of the virus is determined by the envelope gene (env) and substitution of env genes with different cell specificities can be employed. Incorporation of appropriate ligands into the envelope protein may also be used for targeting.

Administration may be achieved by any suitable technique e.g. ex vivo transduction of patients' cells, by the direct injection of virus into tissue, and by the administration of the retroviral producer cells.

The ex vivo approach has a disadvantage in that it requires the isolation and maintenance in tissue culture of the patient's cells, but it has the advantage that the extent of gene transfer can be quantified readily and a specific population of cells can be targeted. In addition, a high ratio of viral particles to target cells can be achieved and thus improve the transduction efficiency (Anderson et al., Hum. Gene Ther., 1990, 1: 331–341; Rosenberg et al., N. Engl. J. Med., 1990, 323: 570–578; Culver et al., Hum. Gene Ther., 1991, 2: 107–109 Nienhuis et al., Cancer, 1991, 67: 2700–2704, Anderson et al., Hum. Gene Ther., 1990, 1: 331–341, Grossman et al., Nat. Genet., 1994, 6:335–341, Lotze el al., Hum. Gene Ther., 1992, 3: 167–177; Lotze, M. T., Cell Transplant., 1993, 2: 33–47; Lotze et al., Hum. Gene Ther., 1994, 5: 41–55 and U.S. Pat. No. 5,399,346 (Anderson). In some cases direct introduction of virus in vivo is necessary. Retroviruses have been used to treat brain tumours wherein the ability of a retrovirus to infect only dividing cells (tumour cells) may be particularly advantageous.

To increase efficiency Oldfield et al., in Hum. Gene Ther., 1993, 4: 39–69 proposed the administration of a retrovirus producer cell line directly into patients' brain tumours. The murine producer cell would survive within the brain tumour for a period of days, and would secrete retrovirus capable of transducing the surrounding brain tumour. Virus carrying the herpes virus thymidine kinase gene renders cells susceptible to killing by ganciclovir, which is metabolized to a cytotoxic compound by thymidine kinase. Patent references on retroviruses are: EP 334301, WO 91/02805 & WO 92/05266 (Viagene) and; U.S. Pat. No. 4,650,764 (University of Wisconsin).

Human adenoviral infections have been described (see Horwitz, M. S., In Virology, $2^{nd}$ ed. Raven Press, New York, 1990, pp. 1723–1740). Most adults have prior exposure to adenovirus and have antiadenovirus antibodies. These viruses possess a double-stranded DNA genome, and replicate independent of host cell division.

Adenoviral vectors possess advantageous properties. They are capable of transducing a broad spectrum of human tissues and high levels of gene expression can be obtained in dividing and nondividing cells. Several routes of administration can be used including intravenous, intrabiliary, intraperitoneal, intravesicular, intracranial and intrathecal injection, and direct injection of the target organ. Thus targeting based on anatomical boundaries is feasible.

The adenoviral genome encodes about 15 proteins and infection involves a fiber protein to bind a cell surface receptor. The penton base of the capsid engages integrin receptor domains ($\alpha_5\beta_3$, or $\alpha_3\beta_5$) on the cell surface resulting in internalization of the virus. Viral DNA enters the nucleus and begins transcription without cell division. Expression and replication is under control by the E1A and E1B genes (see Horwitz, M. S., In Virology, $2^{nd}$ ed., 1990, pp. 1723–1740). Removal of E1 genes renders the virus replication-incompetent. Expression of adenoviral proteins leads to both an immune response which may limit effectiveness particularly on repeat administration. However, recent approaches in which other adenoviral genes such as the E2a gene (which controls expression of the fibre knob and a number of other viral proteins) are also removed from the viral genome may abolish or greatly reduce the expression of many of these viral proteins in target cells.

Adenoviral serotypes 2 and 5 have been extensively used for vector construction. Bett et al., Proc. Nat. Acad. Sci. U.S.A., 1994, 91: 8802–8806 have used an adenoviral type 5 vector system with deletions of the E1 and E3 adenoviral genes. The 293 human embryonic kidney cell line has been engineered to express E1 proteins and can thus transcomplement the E1-deficient viral genome. The virus can be isolated from 293 cell media and purified by limited dilution plaque assays (Graham, F. L. and Prevek, L. In Methods in Molecular Biology: Gene Transfer and Expression Protocols, Humana Press 1991, pp. 109–128). Recombinant virus can be grown in 293 cell line cultures and isolated by lysing infected cells and purification by caesium chloride density centrifugation. One problem of the 293 cells for manufacture of recombinant adenovirus is that due to additional flanking regions of the E1 genes is that they may give rise to replication competent adenovirus (RCA) during the viral particle production. Although this material is only wild type adenovirus and not replication competent recombinant virus it can have significant effects on the eventual yield of the desired adenoviral material and lead to increased manufacturing costs, quality control issues for the production runs and acceptance of batches for clinical use. Alternative cell lines such as the PER.C6 which have more defined E1 gene integration than 293 cells (i.e. contain not flanking viral sequence) have been developed which do not allow the recombination events which produce RCA and thus have the potential to overcome above viral production issues.

Adenoviral vectors have the disadvantage of relatively short duration of transgene expression due to immune system clearance and dilutional loss during target cell division but improvements in vector design are anticipated. Patent references on adenoviruses are: WO 96/03517 (Boehringer); WO 96/13596 (Rhone Poulenc Rorer); WO 95/29993 (University of Michigan) and; WO 96/34969 (Canji). Recent advances in adenoviral vectors for cancer gene therapy including the development of strategies to reduce immunogenicity, chimeric adenoviral/retroviral vectors and conditional (or restricted) replicative recombinant adenoviral systems are reviewed in Bilbao et al., Exp. Opin. Ther. Patents, 1997, 7 (12):1427–1446.

Adeno-associated virus (AAV) (Kotin, R. M., Hum. Gene Ther., 1994, 5: 793–801) are single-stranded DNA, nonautonomous parvoviruses able to integrate into the genome of nondividing cells of a very broad host range. AAV has not been shown to be associated with human disease and does not elicit an immune response.

AAV has two distinct life cycle phases. Wild-type virus will infect a host cell, integrate and remain latent. In the presence of adenovirus, the lytic phase of the virus is induced, which is dependent on the expression of early adenoviral genes, and leads to active virus replication. The AAV genome is composed of two open reading frames (called rep and cap) flanked by inverted terminal repeat (ITR) sequences. The rep region encodes four proteins which mediate AAV replication, viral DNA transcription, and endonuclease functions used in host genome integration. The rep genes are the only AAV sequences required for viral replication. The cap sequence encodes structural proteins that form the viral capsid. The ITRs contain the viral origins of replication, provide encapsidation signals, and participate in viral DNA integration. Recombinant, replication-defective viruses that have been developed for gene therapy lack rep and cap sequences. Replication-defective AAV can be produced by cotransfecting the separated elements necessary for AAV replication into a permissive 293 cell line. Patent references on AAV include: WO 94/13788 (University of Pittsburgh) and U.S. Pat. No. 4,797,368 (US Department of Health).

Gene therapy vectors from pox viruses have been described (Moss, B. and Flexner, C., Annu. Rev. Immunol., 1987, 5: 305–324; Moss, B., In Virology, 1990, pp. 2079–2111). Vaccinia are large, enveloped DNA viruses that replicate in the cytoplasm of infected cells. Nondividing and dividing cells from many different tissues are infected, and gene expression from a nonintegrated genome is observed. Recombinant virus can be produced by inserting the transgene into a vaccinia-derived plasmid and transfecting this DNA into vaccinia-infected cells where homologous recombination leads to the virus production. A significant disadvantage is that it elicits a host immune response to the 150 to 200 virally encoded proteins making repeated administration problematic.

The herpes simplex virus is a large, double-stranded DNA virus that replicates in the nucleus of infected cells suitable for gene delivery (see Kennedy, P. G. E. and Steiner, I., Q. J. Med., 1993, 86: 697–702). Advantages include a broad host cell range, infection of dividing and nondividing cells, and large sequences of foreign DNA can be inserted into the viral genome by homologous recombination. Disadvantages are the difficulty in rendering viral preparations free of replication-competent virus and a potent immune response. Deletion of the viral thymidine kinase gene renders the virus replication-defective in cells with low levels of thymidine kinase. Cells undergoing active cell division (e.g., tumour cells) possess sufficient thymidine kinase activity to allow replication. Cantab Pharmaceuticals have a published patent application on herpes viruses (WO 92/05263).

A variety of other viruses, including HIV, the minute virus of mice, hepatitis B virus, and influenza virus, have been considered as possible vectors for gene transfer (see Jolly, D., Cancer Gene Therapy, 1994, 1: 51–64).

The use of attenuated Salmonella Typhimurium bacteria which specifically target and replicate in hypoxic environments (such as are found in the necrotic centres of tumours) as gene delivery vehicles for prodrug enzyme based therapy (Tumour Amplified Prodrug Enzyme Therapy known as TAPET™) has also been proposed and is under development by Vion Pharmaceuticals. This system offers a further gene delivery alternative to the viral and non-viral delivery approaches discussed below.

Nonviral DNA delivery strategies are also applicable. These DNA delivery systems include uncomplexed plasmid DNA, DNA-liposome complexes, DNA-protein complexes, and DNA-coated gold particles.

Purified nucleic acid can be injected directly into tissues and results in transient gene expression for example in muscle tissue, particularly effective in regenerating muscle (Wolff et al., Science, 1990, 247: 1465–1468). Davis et al., in Hum. Gene Ther., 1993, 4: 733–740 has published on direct injection of DNA into mature muscle. Skeletal and cardiac muscle is generally preferred. Patent references are: WO 90/11092, U.S. Pat. No. 5,589,466 (Vical) and WO 97/05185 (biodegradable DNA impregnated hydrogels for injection, Focal).

Plasmid DNA on gold particles can be "fired" into cells (e.g. epidermis or melanoma) using a gene-gun. DNA is coprecipitated onto the gold particle and then fired using an electric spark or pressurized gas as propellant (Fynan et al., Proc. Natl. Acad. Sci. U.S.A., 1993, 90: 11478–11482). Electroporation has also been used to enable transfer of DNA into solid tumours using electroporation probes employing multi-needle arrays and pulsed, rotating electric fields (Nishi et al., in Cancer Res., 1996, 56:1050–1055). High efficiency gene transfer to subcutaneous tumours has been claimed with significant cell transfection enhancement and better distribution characteristics over intra-tumoural injection procedures.

Liposomes work by surrounding hydrophilic molecules with hydrophobic molecules to facilitate cell entry. Liposomes are unilamellar or multilamellar spheres made from lipids. Lipid composition and manufacturing processes affect liposome structure. Other molecules can be incorporated into the lipid membranes. Liposomes can be anionic or cationic. Nicolau et al., Proc. Natl. Acad. Sci. U.S.A., 1983, 80: 1068–1072 has published on insulin expression from anionic liposomes injected into rats. Anionic liposomes mainly target the reticuloendothelial cells of the liver, unless otherwise targeted. Molecules can be incorporated into the surface of liposomes to alter their behavior, for example cell-selective delivery (Wu, G. Y. and Wu, C. H., J. Biol. Chem., 1987, 262: 4429–4432).

Felgner et al., Proc. Nat. Acad. Sci. U.S.A., 1987, 84: 7413–7417 has published on cationic liposomes, demonstrated their binding of nucleic acids by electrostatic interactions and shown cell entry. Intravenous injection of cationic liposomes leads to transgene expression in most organs on injection into the afferent blood supply to the organ. Cationic liposomes can be administered by aerosol to target lung epithelium (Brigham et al., Am. J. Med. Sci., 1989, 298: 278–281). Patent references on liposomes are: WO 90/11092, WO 91/17424, WO 91/16024, WO 93/14788 (Vical) and; WO 90/01543 (Intracel).

In-Vivo studies with cationic liposome transgene delivery have been published by: Nabel et al., Rev. Hum. Gene Ther., 1994, 5: 79–92; Hyde et al., Nature, 1993, 362: 250–255 and; Conary et al., J. Clin. Invest., 1994, 93: 1834–1840).

Microparticles are being studied as systems for delivery of DNA to phagocytic cells such approaches have been pursued by Pangaea Pharmaceuticals in their ENDOSHERE™ DNA microencapsulation delivery system which has been used to effect more efficient transduction of phagocytic cells such as macrophages which ingest the microspheres. The microspheres encapsulate plasmid DNA encoding potentially immunogenic peptides which when expressed lead to peptide display via MHC molecules on the cell surface which can stimulate immune response against such peptides and protein sequences which contain the same epitopes. This approach is presently aimed towards a potential role in anti-tumour and pathogen vaccine development but may have other possible gene therapy applications.

In the same way as synthetic polymers have been used to package DNA natural viral coat proteins which are capable of homogeneous self-assembly into Virus-like particles (VLPs) have been used to package DNA. The major structural coat protein VP1 of human polyoma virus can be expressed as a recombinant protein and is able to package plasmid DNA during self-assembly into a VLP. The resulting particles can be subsequently used to transduce various cell lines, while preliminary studies show little immunogenic response to such VP1 based VLPs. Such systems may offer an attractive intermediate between synthetic polymer non-viral vectors and the alternative viral delivery systems since they may offer combined advantages e.g. simplicity of production and high level transduction efficiency.

To improve the specificity of gene delivery and expression the therapeutic gene the inclusion of targeting elements into the delivery vehicles and the use of regulatory expression elements have been investigated both singlulary and in combination in many of the previously described delivery systems.

Improvements in DNA vectors have also been made and are likely applicable to all of the non-viral delivery systems. These include the use of supercoiled minicircles reported by RPR Gencell (which do not have bacterial origins of replication nor antibiotic resistance genes and thus are potentially safer as they exhibit a high level of biological containment), episomal expression vectors as developed by Copernicus Gene Systems Inc (replicating episomal expression systems where the plasmid amplifies within the nucleus but outside the chromosome and thus avoids genome integration events) and T7 systems as developed by Progenitor (a strictly a cytoplasmic expression vector in which the vector itself expresses phage T7 RNA polymerase and the therapeutic gene is driven from a second T7 promoter, using the polymerase generated by the first promoter). Other, more general improvements to DNA vector technology include use of cis-acting elements to effect high levels of expression (Vical), sequences derived from alphoid repeat DNA to supply once-per-cell-cycle replication and nuclear targeting sequences (from EBNA-1 gene (Calos at Stanford, with Megabios); SV40 early promoter/enhancer or peptide sequences attached to the DNA).

Targeting systems based on cell receptor recognition by ligand linked to DNA have been described by Michael, S. I. and Curiel, D. T., Gene Therapy, 1994, 1: 223–232. Using the ligand recognized by such a receptor the DNA becomes selectively bound and internalized into the target cell (Wu, G. Y. and Wu, C. H., J. Biol. Chem., 1987, 262: 4429–4432). Poly-L-lysine (PLL), a polycation, has been used to couple a variety of protein ligands to DNA by chemical cross-linking methods. DNA is electrostatically bound to PLL-ligand molecules. Targetting systems have been published by Zenke et al., Proc. Nat. Acad. Sci. U.S.A., 1990, 87: 3655–3659 using transferrin receptor; Wu, G. Y. and Wu, C. H., J. Biol. Chem., 1987. 262: 4429–4432 using the asialoorosomucoid receptor, and Batra et al., Gene Therapy, 1994, 1: 255–260, using cell surface carbohydrates. Agents such as chloroquine or co-localised adenovirus can be used to reduce DNA degradation in the lysosomes (see Fisher, K. J. and Wilson, J. M., Biochem. J., 1994, 299, 49–58). Cristiano et al., Proc. Natl. Acad. Sci. U.S.A., 1993, 90: 11548–11552 has constructed adenovirus-DNA-ligand complexes. Patent references on receptor mediated endocytosis are: WO 92/05250 (asialoglycoproteins, University of Connecticut) and U.S. Pat. No. 5,354,844 (transferrin receptor, Boehringer).

DNA and ligand can be coated over the surface of the adenovirus to create a coated adenovirus (Fisher, K. J. and Wilson, J. M., Biochem. J., 1994, 299, 49–58). However the presence of two receptor pathways for DNA entry (ligand receptor and adenovirus receptor) reduces the specificity of this delivery system but the adenovirus receptor pathway can be eliminated by using an antibody against adenovirus fiber protein as the means for linkage to DNA (Michael, S. I. and Curiel, D. T., Gene Therapy, 1994, 1: 223–232). Use of purified endosomalytic proteins rather than intact adenovirus particles is another option (Seth, P., J. Virol., 1994, 68: 1204–1206).

The expression of a gene construct of the invention at its target site is preferably under the control of a transcriptional regulatory sequence (TRS). A TRS is a promoter optionally combined with an enhancer and/or an control element such as a genetic switch described below.

One example of a TRS is a "genetic switch" that may be employed to control expression of a gene construct of the invention once it has been delivered to a target cell. Control of gene expression in higher eucaryotic cells by procaryotic regulatory elements (which are preferred for the present invention) has been reviewed by Gossen et al in TIBS, Dec. 18, 1993, 471–475. Suitable systems include the *E. coli* lac operon and the especially preferred *E. coli* tetracycline resistance operon. References on the tetracycline system include Gossen et al (1995) Science 268, 1766; Damke et al (1995) Methods in Enzymology 257, Academic Press; Yin et al (1996) Anal. Biochem. 235, 195 and; U.S. Pat. Nos. 5,464,758, 5,589,362, WO 96/01313 and WO 94/29442 (Bujard). An ecdysone based switch (International Patent Appln No.PCT/GB96/01195, Publication No. WO 96/37609, Zeneca) is another option. Other options are listed below. Connaught Laboratories (WO-93/20218) describe a synthetic inducible eukaryotic promoter comprising at least two different classes of inducible elements. Rhone-Poulenc Rorer (WO 96/30512) describe a tetracycline-related application for a conditional gene expression system. Ariad (WO 94/18317) describes a protein dimerisation based system for which in vivo activity has been shown. Bert O'Malley of the Baylor College of Medicine (WO 93/23431, U.S. Pat. No. 5,364,791, WO 97/10337) describes a molecular switch based on the use of a modified steroid receptor. The Whitehead Institute have an NF-KB inducible gene expression system (WO 88/05083). Batelle Memorial have described a stress inducible promoter (European patent EP 263908).

Examples of TRSs which are independent of cell type include the following: cytomegalovirus promoter/enhancer, SV40 promoter/enhancer and retroviral long terminal repeat promoter/enhancer. Examples of TRSs which are dependent on cell type (to give an additional degree of targeting) include the following promoters: carcinoembryonic antigen (CEA) for targeting colorectal, lung and breast; alpha-foetoprotein (AFP) for targeting transformed hepatocytes; tyrosine hydroxylase, choline acetyl transferase or neurone specific enolase for targeting neuroblastomas; insulin for targeting pancreas and; glial fibro acidic protein for targeting glioblastomas. Some oncogenes may also be used which are selectively expressed in some tumours e.g. HER-2/neu or c-erbB2 in breast and N-myc in neuroblastoma.

SUMMARY OF INVENTION

Accordingly, a preferred gene construct for use as a medicament is a construct comprising a transcriptional regulatory sequence which comprises a promoter and a control element which is a genetic switch to control expression of the gene construct. A preferred genetic switch control element is regulated by presence of tetracycline or ecdysone. A preferred promoter is dependent on cell type and is selected from the following promoters: carcinoembryonic antigen (CEA); alpha-foetoprotein (AFP); tyrosine hydroxylase; choline acetyl transferase; neurone specific enolase; insulin; glial fibro acidic protein; HER-2/neu; c-erbB2; and N-myc. Preferably the gene construct for use as a medicament described herein is packaged within an adenovirus for delivery to the mammalian host. A general review of targeted gene therapy is given in Douglas et al., Tumor Targeting, 1995, 1: 67–84.

The antibody encoded by the gene construct of the invention may be any form of antibody construct such as for example $F(ab')_2$; F(ab'), Fab, Fv, single chain Fv & V-min. Any suitable antibody construct is contemplated, for example a recently described antibody fragment is "L-F(ab)$_2$" as described by Zapata (1995) in Protein Engineering, 8, 1057–1062. Disulphide bonded Fvs are also contemplated. For constructs based on CPG2 enzyme, Fab fragment constructs dimerised through enzyme dimerisation are preferred. Non-human antibodies may be humanised for use in humans to reduce host immune responses. A humanized antibody, related fragment or antibody binding structure is a polypeptide composed largely of a structural framework of human derived immunoglobulin sequences supporting non human derived amino acid sequences in and around the antigen binding site (complementarity determining regions or CDRs). Appropriate methodology has been described for example in detail in WO 91/09967, EP 0328404 and Queen et al. Proc Natl Acad Sci 86 10029, Mountain and Adair (1989) Biotechnology and Genetic Engineering Reviews 10, 1 (1992) although alternative methods of humanisation are also contemplated such as antibody veneering of surface residues (EP 519596, Merck/NIH, Padlan et al).

According to another aspect of the present invention there is provided a matched two component system designed for use in a mammalian host in which the components comprise:

(i) a first component that comprises a gene construct encoding a cell targeting antibody and a heterologous prodrug activating enzyme wherein the gene construct is capable of expressing the antibody and enzyme as a conjugate within a target cell in the mammalian host and wherein the conjugate can leave the cell thereafter for selective localisation at a cell surface antigen recognised by the antibody and;

(ii) a second component that comprises a prodrug which can be converted into an active drug by the enzyme.

Antibody directed enzyme prodrug therapy (ADEPT) is a known cancer therapeutic approach. ADEPT uses a tumour selective antibody conjugated to an enzyme. The conjugate is administered to the patient (usually intravenously), allowed to localise at the tumour site(s) and clear from the blood and other normal tissues. A prodrug is then administered to the patient which is converted by the enzyme (localised at the tumour site) into a cytotoxic drug which kills the tumour cells.

The present invention can be applied to any ADEPT system. Suitable examples of ADEPT systems include those based on any of the following enzymes: carboxypeptidase G2; carboxypeptidase A; aminopeptidase; alkaline phosphatase; glycosidases; β-glucuronidase; penicillin amidase; β-lactamase; cytosine deaminase; nitroreductase; or mutant host enzymes including carboxypeptidase A, carboxypeptidase B, and ribonuclease. Suitable references on ADEPT systems include Melton R G (1996) in J. National Cancer Institute 88, 1; Niculescu-Duvaz I (1995) in Current Medicinal Chemistry 2, 687; Knox R J (1995) in Clin. Immunother. 3, 136; WO 88/07378 (CRCT); Blakey et al., Cancer Res. 56, 3287–92, 1996; U.S. Pat. No. 5,587,161 (CRCT and Zeneca); WO 97/07769 (Zeneca); and WO 95/13095 (Wellcome). The heterologous enzyme may be in the form of a catalytic antibody; see for example EP 745673 (Zeneca). A review articles on ADEPT systems include Hay & Denny (1996), Drugs of the Future, 21(9), 917–931 and Blakey (1997), Exp. Opin. Ther. Patents, 7(9), 965–977.

A preferred matched two component system is one in which: the first component comprises a gene encoding the heterologous enzyme CPG2; and the second component prodrug is selected from N-(4-[N,N-bis(2-iodoethyl)amino]-phenoxycarbonyl)-L-glutamic acid, N-(4-[N,N-bis(2-chloroethyl)amino]-phenoxycarbonyl)-L-glutamic-gamma-(3,5-dicarboxy)anilide or N-(4-[N,N-bis(2-chloroethyl)amino]-phenoxycarbonyl)-L-glutamic acid or a pharmaceutically acceptable salt thereof. Preferred prodrugs for use with CPG2 are described in the following US patents from Zeneca Limited and Cancer Research Campaign Technology Limited: U.S. Pat. Nos. 5,714,148, 5,405,990, 5,587,161 & 5,660,829.

In another aspect of the invention there is provided a method for the delivery of a cytotoxic drug to a site which comprises administering to a host a first component that comprises a gene construct as defined herein; followed by administration to the host of a second component that comprises a prodrug which can be converted into a cytotoxic drug by the heterologous enzyme encoded by the first component. A preferred method for delivery of a cytotoxic drug to a site is one in which the first component comprises a gene encoding the heterologous enzyme CPG2; and the second component prodrug is selected from N-(4-[N,N-bis(2-iodoethyl)amino]phenoxycarbonyl)-L-glutamic acid, N-(4-[N,N-bis(2-chloroethyl)amino]-phenoxycarbonyl)-L-glutamic-gamma-(3,5-dicarboxy)anilide or N-(4-[N,N-bis(2-chloroethyl)amino]-phenoxycarbonyl)-L-glutamic acid or a pharmaceutically acceptable salt thereof.

Abbreviations used herein include:

| | |
|---|---|
| AAV | Adeno-associated virus |
| ADEPT | antibody directed enzyme prodrug therapy |
| AFP | alpha-foetoprotein |
| AMIRACS | Antimetabolite with Inactivation of Rescue Agents at Cancer Sites |
| APS | ammonium persulfate |
| b.p. | base pair |
| BPB | bromophenol blue |
| CDRs | complementarity determining regions |
| CEA | Carcinoma Embryonic Antigen |
| CL | constant domain of antibody light chain |
| CPB | carboxypeptidase B |
| CPG2 | carboxypeptidase G2 |
| CPG2 R6 | carboxypeptidase G2 mutated to prevent glycosylation on expression in eucaryotic cells, see Example 1d |
| DAB | substrate 3,3'-diaminobenzidine tetrahydrochloride |
| DEPC | diethylpyrocarbonate |
| DMEM | Dulbecco's modified Eagle's medium |
| ECACC | European Collection of Animal Cell Cultures |
| EIA | enzyme immunoassay |
| ELISA | enzyme linked immunosorbent assay |
| FAS | folinic acid supplemented |
| FCS | foetal calf serum |
| Fd | heavy chain of Fab, Fab' or F(ab')$_2$ optionally containing a hinge |
| GDEPT | gene directed enzyme prodrug therapy |
| HAMA | Human Anti Mouse Antibody |
| HCPB | human carboxypeptidase B, preferably pancreatic |
| hinge (of an IgG) | a short proline rich peptide which contains the cysteines that bridge the 2 heavy chains |
| HRPO or HRP | horse radish peroxidase |
| IRES | internal ribosome entry site |
| MTX | methotrexate |
| NCA | non-specific cross reacting antigen |
| NCIMB | National Collections of Industrial and Marine Bacteria |
| OPD | ortho-phenylenediamine |
| PBS | phosphate buffered saline |
| PCR | polymerase chain reaction |
| PGP | N-(4-[N,N-bis(2-chloroethyl)amino]-phenoxycarbonyl)-L-glutamic acid |
| preproCPB | proCPB with an N-terminal leader sequence |
| proCPB | CPB with its N-terminal pro domain |
| scFv | single chain Fv |
| SDS-PAGE | sodium dodecyl sulphate - polyacrylamide gel electrophoresis |
| SSC | salt sodium citrate |
| TBS | Tris-buffered Saline |
| Temed | N,N,N',N'-tetramethylethylenediamine |
| TFA | trifluoroacetic acid |
| TRS | transcriptional regulatory sequence |
| VDEPT | virus-directed enzyme prodrug therapy |
| VH | variable region of the heavy antibody chain |
| VK | variable region of the light antibody chain |

In this specification conservative amino acid analogues of specific amino acid sequences are contemplated which retain the relevant biological properties of the component of the invention but differ in sequence by one or more conservative amino acid substitutions, deletions or additions. However the specifically listed amino acid sequences are preferred. Typical conservative amino acid substitutions are tabulated below.

| Original | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp; Phe; Thr; Ser | Phe |
| Val (V) | Ile; Leu; Met; Phe; Ala; Norleucine | Leu |

Amino acid nomenclature is set out below.

| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any Amino Acid | Xaa | X |

In this specification nucleic acid variations (deletions, substitutions and additions) of specific nucleic acid sequences are contemplated which retain which the ability to hybridise under stringent conditions to the specific sequence in question. Stringent conditions are defined as 6×SSC, 0.1% SDS at 60° for 5 minutes. However specifically listed nucleic acid sequences are preferred. It is contemplated that chemical analogues of natural nucleic acid structures such as "peptide nucleic acid" (PNA) may be an acceptable equivalent, particularly for purposes that do not require translation into protein (Wittung (1994) Nature 368, 561).

The invention will now be illustrated by reference to the following non-limiting Examples. Temperatures are in degrees Celsius.

BRIEF DESCRIPTION OF DRAWINGS

FIG. 1 shows a representation of the fusion gene construct comprising A5B7 antibody heavy chain Fd fragment linked at its C-terminus via a flexible $(G_4S)_3$ peptide linker to the N-terminus of CPG2 polypeptide. SS represents the signal sequence. L represents a linker sequence. CPG2/R6 represents CPG2 with its glycosylation sites nullified through mutation as explained in the text.

FIG. 2a shows a representation of $(Fab-CPG2)_2$ fusion protein with dimerisation taking place through non-covalent bonding between two CPG2 molecules.

FIG. 2b shows a representation of a $F(ab')_2$ antibody fragment.

Figure 3:
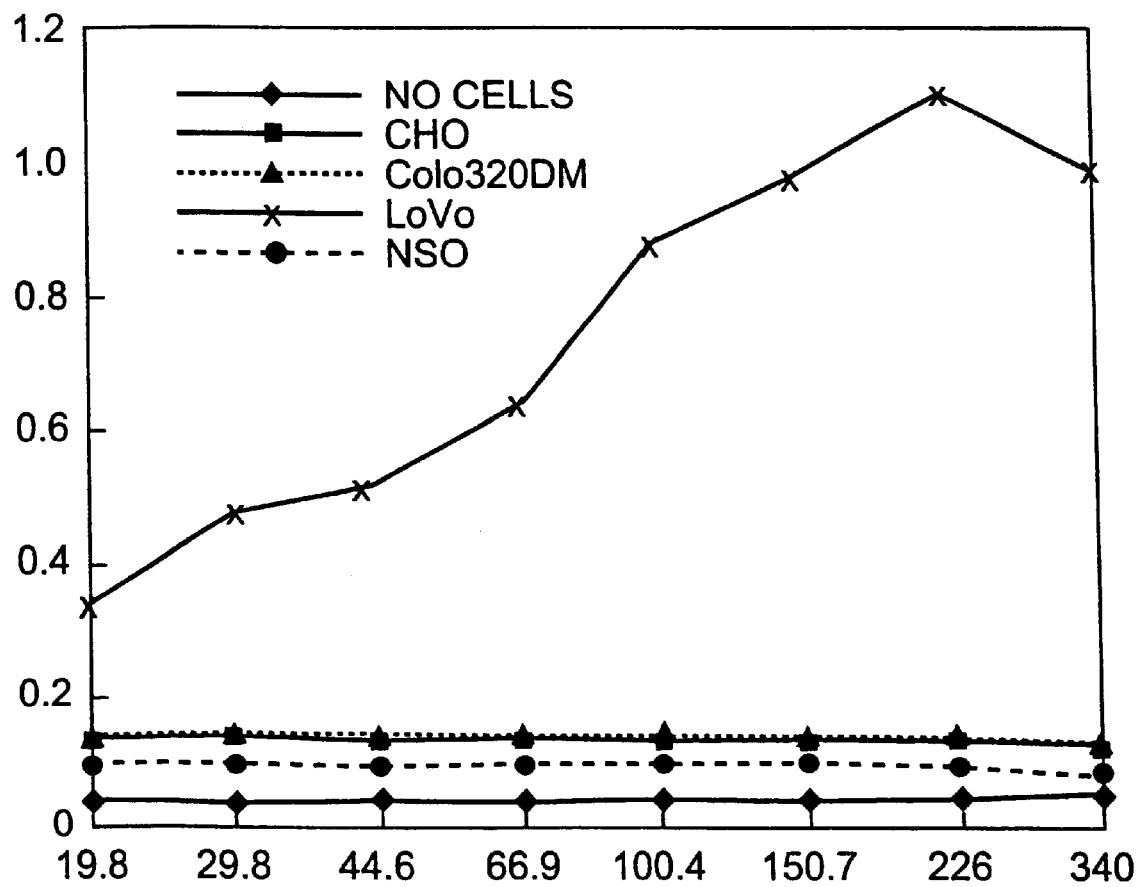
FIG. 3 shows a cell based ELISA assay of secreted fusion protein material. Only the CEA positive line has increased levels of binding with increasing amounts of added fusion protein whereas the CEA negative cell line has only constant background binding levels throughout. The vertical axis represents optical density readings measured at 490 nm and the horizontal axis the amount of added fusion protein measured in ng of protein. The graph shows data obtained from an experiment where a number of cell lines and a negative control (no cells) were incubated with increasing amounts of fusion protein using the cell assay described in Example 6. The results show that only the LoVo (CEA positive) cell line showed an increasing OD490 reading corresponding to increasing amounts of addes fusion protein. All other cell lines (CEA negative) and the control (no cells) showed only a background OD490 nm reading which did not increase with the addition of fusion protein. These results provide evidence that the fusion protein material binds specifically to a CEA positive cell line in a dose dependant manner and do not bind to CEA negative lines.

In the Examples below, unless otherwise stated, the following methodology and materials have been applied.

DNA is recovered and purified by use of GENECLEAN™ II kit (Stratech Scientific Ltd. or Bio 101 Inc.). The kit contains: 1) 6M sodium iodide; 2) a concentrated solution of sodium chloride, Tris and EDTA for making a sodium chloride/ethanol/water wash; 3) Glassmilk—a 1.5 ml vial containing 1.25 ml of a suspension of a specially formulated silica matrix in water. This is a technique for DNA purification based on the method of Vogelstein and Gillespie published in Proceedings of the National Academy of Sciences USA (1979) Vol 76, p 615. Briefly, the kit procedure is as follows. To 1 volume of gel slice is added 3 volumes of sodium iodide solution from the kit. The agarose is melted by heating the mix at 55° for 10 min then Glassmilk (5–10 ml) is added, mixed well and left to stand for 10 min at ambient temperature. The glassmilk is spun down and washed 3 times with NEW WASH™ (0.5 ml) from the kit. The wash buffer is removed from the Glassmilk and DNA is eluted by incubating the Glassmilk with water (5–10 ml) at 55° for 5–10 min. The aqueous supernatant containing the eluted DNA is recovered by centrifugation. The elution step can be repeated and supernatants pooled.

Competent *E. coli* DH5α cells were obtained from Life Technologies Ltd (MAX™ efficiency DH5α competent cells).

Mini-preparations of double stranded plasmid DNA were made using the RPM™ DNA preparation kit from Bio 101 Inc. (cat. No 2070–400) or a similar product—the kit contains alkaline lysis solution to liberate plasmid DNA from bacterial cells and glassmilk in a spinfilter to adsorb liberated DNA which is then eluted with sterile water or 10 mM Tris-HCl, 1 mM EDTA, pH 7.5.

The standard PCR reaction contains 100 ng of plasmid DNA (except where stated), 5 μl dNTPs (2.5 mM), 5 μl 10×Enzyme buffer (500 mM KCl, 100 mM Tris pH 8.3), 15 mM $MgCl_2$ and 0.1% gelatin), 1 μl of a 25 pM/μl stock solution of each primer, 0.5 μl thermostable DNA polymerase and water to obtain a volume of 50 μl. Standard PCR conditions were: 15 cycles of PCR at 94° for 90 s; 55° for 60 s; 72° for 120 s, ending the last cycle with a further 72° for 10 min incubation.

AMPLITAQ™, available from Perkin-Elmer Cetus, is used as the source of thermostable DNA polymerase.

General molecular biology procedures can be followed from any of the methods described in "Molecular Cloning—A Laboratory Manual" Second Edition, Sambrook, Fritsch and Maniatis (Cold Spring Harbor Laboratory, 1989).

Serum free medium is OPTIMEM™ I Reduced Serum Medium, GibcoBRL Cat. No. 31985. This is a modification of Eagle's Minimum Essential Medium buffered with Hepes and sodium bicarbonate, supplemented with hypoxanthine, thymidine, sodium pyruvate, L-glutamine, trace elements and growth factors.

LIPOFECTIN™ Reagent (GibcoBRL Cat. No. 18292-011) is a 1:1 (w/w) liposome formulation of the cationic lipid N-[1-(2,3-dioleyloxy)propyl]-n,n,n-trimethylammonium chloride (DOTMA) and dioleoyl phosphatidylethanolamine (DOPE) in membrane filtered water. It binds spontaneously with DNA to form a lipid-DNA complex—see Felgner et al. in Proc. Natl. Acad. Sci. USA (1987) 84, 7431.

G418 (sulphate) is GENETICIN™, GibcoBRL Cat. No 11811, an aminoglycoside antibiotic related to gentamicin used as a selecting agent in molecular genetic experiments;

For the CEA ELISA each well of a 96 well immunoplate (NUNC MAXISORB™) was coated with 50 ng CEA in 50 mM carbonate/bicarbonate coating buffer pH9.6 (buffer capsules—Sigma C3041) and incubated at 4° overnight. The plate was washed three times with PBS-TWEEN™ (PBS+ 0.05% TWEEN™ 20) and then blocked 150 μl per well of 1% BSA in PBS-TWEEN™ for 1 hour at room temperature. The plate was washed three times with PBS-TWEEN™, 100 μl of test sample added per well and incubated at room temperature for 2 hours. The plate was washed three times with PBS-TWEEN™, 100 μl per well of a 1/500 dilution of HRPO-labelled goat anti-human kappa antibody (Sigma A 7164) was added in 1% BSA in PBS-TWEEN™ and incubated at room temperature on a rocking platform for at least 1 hour. The plate was washed three times with PBS-TWEEN™ and then once more with PBS. To detect binding, add 100 μl per well of developing solution (one capsule of phosphate-citrate buffer—Sigma P4922—dissolved in 100 ml $H_2O$ to which is added one 30 mg tablet o-phenylenediamine dihydrochloride—Sigma P8412) and incubated for up to 15 minutes. The reaction was stopped by adding 75 μl 2M $H_2SO_4$, and absorbance read at 490 nm.

The CEA ELISA using an anti CPG2 reporter antibody was essentially as above but instead of HRPO-labelled goat anti-human kappa antibody an 1/1000 dil. of a rabbit anti-CPG2 polyclonal sera was added, in 1% BSA in PBS-TWEEN™ and incubated at room temperature on a rocking platform for at 2 hours. The plate was washed three times with PBS-TWEEN™. A 1/2000 dilution of a goat anti-rabbit HRPO labelled antibody (Sigma A-6154) was then added and incubated at room temperature on a rocking platform for 1 hour, the plate was washed three times with PBS-TWEEN™ and once with PBS. To detect binding add 100 μl per well developing solution (one capsule of phosphate-citrate buffer—Sigma P4922—dissolved in 100 ml $H_2O$ to which is added one 30 mg tablet o-phenylenediamine dihydrochloride—Sigma P8412) and incubated for up to 15 minutes. The reaction was stopped by adding 75 μl 2M $H_2SO_4$, and absorbance read at 490 nm.

Western blot analysis of transfection supernatants was performed as follows. 10% mini gels for analysis of fusion protein transfections were prepared using a suitable mini gel system (HOEFER MIGHTY SMALL™). 10% running gel is: 20 ml acrylamide, 6 ml 10×running gel buffer; 34 ml $H_2O$; 300 ml 20% SDS; 600 μl APS; 30 μl Temed. Running gel buffer 10× is 3.75 M Tris pH 8.6. 6% stacking gel is: 9 ml acrylamide; 4.5 ml 10×stacking gel buffer; 31.5 ml H$_2$O; 225 μl 20% SDS 450 μl 10% APS; 24 μl Temed). Stacking gel buffer 10× is 1.25 M Tris pH 6.8. Electrophoresis buffer 5× for SDS/PAGE is 249 mM Tris, 799 mM glycine, 0.6% w/v SDS (pH not adjusted).

Preparation of samples 2×Laemmli buffer is 0.125 M Tris; 4% SDS; 30% glycerol; 4 M urea; 0.002% BPB optionally containing 5% β-mercaptoethanol. Supernatants: 25 μl sample+25 μl 2×Laemmli buffer; 40 μl loaded. Standards F(ab')$_2$ and CPG2: 2 μl of 10 ng/ml of standard; 8 μl of H$_2$O; 10 μl 2×Laemmli buffer (−mercaptoethanol); 20 μl loaded. Molecular weight markers (Amersham RAINBOW™): 8 μl sample; 8 μl 2×Laemmli buffer (+mercaptoethanol): 16 μl loaded. Running conditions: 30 milliamps until dye front at bottom of gel(approx. 1 hour). Blotting: using a semi dry blotter (LKB) onto nitrocellulose membrane. Milliamps= 0.7×cm$^2$, for 45 minutes. Blocking: 5% dried skimmed milk in PBS-TWEEN™ for 40 minutes.

Detection of F(ab')$_2$ :goat anti human kappa light chain HRPO labelled antibody, 1/2500 in 0.5% dried skimmed milk in PBS-TWEEN™ incubated overnight.

Detection of CPG2: mouse anti-CPG2 monoclonal (1/2000 in 0.5% dried skimmed milk in PBS-TWEEN™ incubated overnight; goat anti mouse kappa light chain HRPO labelled antibody—Sigma 674301—(1/10000 in 0.5% dried skimmed milk in PBS-TWEEN™) incubated for at least 2 hours.

Development of Blot: Chemiluminescence detection of HRPO based on luminol substrate in the presence of enhancer was used (Pierce SUPERSIGNAL™ Substrate). Substrate working solution was prepared as follows: recommended volume: 0.125 ml/cm$^2$ of blot surface. Mix equal volumes of luminol/enhancer solution and stable peroxide solution, incubate blot with working solution for 5–10 minutes, remove solution and place blot in a membrane protector and expose against autoradiographic film (usually between 30 seconds and 5 minutes).

Microorganism deposits: Plasmid pNG3-Vkss-HuCk was deposited at The National Collections of Industrial and Marine Bacteria (NCIMB), 23 St Machar Drive, Aberdeen AB2 1RY, Scotland, United Kingdom on Apr. 11, 1996 under deposit reference number NCIMB 40798 in accordance with the Budapest Treaty. Plasmid pNG4-VHss-HuIgG2CH1' was deposited at The National Collections of Industrial and Marine Bacteria (NCIMB), 23 St Machar Drive, Aberdeen AB2 1RY, Scotland, United Kingdom on Apr. 11, 1996 under deposit reference number NCIMB 40797 in accordance with the Budapest Treaty. Plasmid pNG3-Vkss-HuCk-NEO was deposited at The National Collections of Industrial and Marine Bacteria (NCIMB), 23 St Machar Drive, Aberdeen AB2 1RY, Scotland, United Kingdom on Apr. 11, 1996 under deposit reference number NCIMB 40799 in accordance with the Budapest Treaty. Plasmid pICI266 was deposited under accession number NCIMB 40589 on Oct. 11, 1993 under the Budapest Treaty at the National Collections of Industrial and Marine Bacteria Limited (NCIMB), 23 St. Machar Drive, Aberdeen, AB2 1RY, Scotland, U.K.

Typsinisation: Trypsin EDTA (Gibco BRL 45300-019) and Hanks balanced salt solution (HBSS; Gibco BRL 14170-088) were pre-warmed in a 37° waterbath. Existing media was removed from cultures and replaced with a volume of HBSS (which is half the previous media volume) and the layer of cells washed by carefully rocking the plate or flask so as to remove any residual serum containing media. The HBSS was removed and a volume of Trypsin solution (which is one quarter of the original media volume) added, with gently rocking the flask to ensure the cell layer was completely covered and left for 5 min. Trypsin was inactivated by addition of of the appropriate normal culture media (2×the volume of the trypsin solution). The cell suspension was then either cell counted or further diluted for continued culture depending on the procedure to be performed.

Heat Inactivation of Foetal Calf Serum (FCS): FCS (Viralex A15-651 accredited batch—Non European) was stored at −20°. For use, the serum was completely thawed at 4° overnight. The next day, the serum was incubated for 15 min in a 37° waterbath and then transferred to a 56° waterbath for 15 min. The serum was removed and allowed to cool to room temperature before it was split in to 50 ml aliquots and stored at −20° C.

Normal DMEM Media (using Gibco BRL components): To 500 ml DMEM (41966-086) add 12.5ml Hepes (15630-056); 5 ml NEAA (11140-035); 5 ml pen/strep (10378-016); and 50 ml heat inactivated FCS.

FAS Media (using Gibco BRL components unless stated otherwise): 490 ml DMEM (41966-086); 12.5 ml Hepes (15630-056); 5 ml non-essential amino acids (11140-035); 5 ml pen/strep (10378-016); 5 ml vitamins (11120-037); 5ml basal amino acids (51051-019); Folinic Acid (Sigma F8259) to a final media concentration of 10 μg/ml ; 50 ml heat inactivated FCS; 5 ml dNTP mix; and G418 50 mg/ml stock solution (to produce the appropriate selection concentration).

dNTP mix: 35 mg G (Sigma G6264), 35 mg C (Sigma C4654), 35 mg A (Sigma A4036), 35 mg U (SigmaU3003), 125 mg T (Sigma T1895) were dissolved in 100 ml water, filter sterilised, and stored at −20°.

G418 Selection: for LoVo cells (ATCC CCL 229) selection was performed at 1.25 mg/ml, for HCT116 (ATCC CCL 247) cells and for Colo320DM (ATCC CCL 220) cells selection was performed at 1.5 mg/ml unless stated otherwise.

BLUESCRIPT™ vectors were obtained from Stratagene Cloning Systems.

Tet-On gene expression vectors were obtained from Clontech (Palo Alto, Calif.) cat. no. K1621-1.

Unless stated otherwise or apparent from the context used, antibody-CPG2 fusion constructs referred to in the Examples use mutated CPG2 to prevent glycosylation.

EXAMPLE 1

Construction of an (A5B7 Fab-CPG2)$_2$ Fusion Protein

The construction of a (A5B7 Fab-CPG2)2 enzyme fusion was planned with the aim of obtaining a bivalent human carcinoembryonic antigen (CEA) binding molecule which also exhibits CPG2 enzyme activity. To this end the initial construct was designed to contain an A5B7 antibody heavy chain Fd fragment linked at its C-terminus via a flexible (G$_4$S)$_3$ peptide linker to the N-terminus of the CPG2 polypeptide (FIG. 1).

The antibody ASB7 binds to human carcinoembryonic antigen (CEA) and is particularly suitable for targeting colorectal carcinoma or other CEA antigen bearing cells (the importance of CEA as a cancer associated antigen is reviewed by Shively, J. E. and Beatty, J. D. in "CRC Critical Reviews in Oncology/Hematology", vol 2, p355–399, 1994). The CPG2 enzyme is naturally dimeric in nature, consisting of two associated identical polypeptide subunits. Each subunit of this molecular dimer consists of a larger catalytic domain and a second smaller domain that forms the dimer interface.

In general, antibody (or antibody fragment)-enzyme conjugate or fusion proteins should be at least divalent, that is to say capable of binding at least 2 tumour associated antigens (which may be the same or different). In the case of the (A5B7 Fab-CPG2)$_2$ fusion protein, dimerisation of the enzyme component takes place after expression, as with the native enzyme, thus forming an enzymatic molecule which contains two Fab antibody fragments (and is thus bivalent with respect to antibody binding sites) and two molecules of CPG2 (FIG. 2a).

a) Cloning of the A5B7 Antibody Genes

Methods for the preparation, purification and characterisation of recombinant murine A5B7 F(ab')$_2$ antibody have been published (International Patent Application, Zeneca Limited, WO 96/2001 1, see Reference Example 5 therein). In Reference Example 5, section f thereof, the A5B7 antibody genes were cloned into vectors of the GS-SYSTEM™ (Celltech), see International Patent Applications WO 87/04462, WO 89/01036, WO 86/05807 and WO 89/10404, with the A5B7 Fd cloned into pEE6 and the light chain into pEE12. These vectors were the source of the A5B7 antibody genes for the construction of the ASB7 Fab-CPG2 fusion protein.

b) Chimaeric A5B7 Vector Constructs

The A5B7 murine antibody variable regions were amplified by PCR from the pEE6 and pEE12 plasmid vectors using appropriate PCR primers which included the necessary restriction sites for direct in frame cloning of the heavy and light chain variable regions into the vectors pNG4-VHss-HulgG2CH1' (NCIMB deposit no. 40797) and pNG3-Vkss-HuCk-NEO (NCIMB deposit no. 40799) respectively. The resulting vectors were designated pNG4/A5B7VH-IgG2CH1' (A5B7 chimaeric heavy chain Fd') and pNG3/A5B7VK-HuCK-NEO (A5B7 chimaeric light chain).

c) Cloning of the CPG2 Gene

The CPG2 coding gene may be obtained from Centre for Applied Microbiology and Research, Porton Down, Salisbury, Wiltshire SP4 0JG, United Kingdom. CPG2 may also be obtained by recombinant techniques. The nucleotide coding sequence for CPG2 has been published by Minton, N. P. et al., Gene, (1984) 31, 31–38. Expression of the coding sequence has been reported in E.coli (Chambers, S. P. et al., Appl. Microbiol, Biotechnol. (1988), 29, 572–578) and in Saccharomyces cerevisiae (Clarke, L. E. et al., J. Gen Microbiol, (1985) 131, 897–904). In addition the CPG2 gene may be produced as a synthetic DNA construct by a variety of methods and used as a source for further experiments. Total gene synthesis has been described by M. Edwards in Am. Biotech. Lab (1987), 5, 38–44, Jayaraman et al. (1991) Proc. Natl. Acad. Sci. USA 88, 4084–4088, Foguet and Lubbert (1992) Biotechniques 13, 674–675 and Pierce (1994) Biotechniques 16, 708.

In preparation for the cloning the CPG2 gene the vector pNG3-Vkss was constructed which is a simple derivative of pNG3-Vkss-HuCk-NEO (NCIMB deposit no. 40799). This vector was constructed by first removing the Neomycin gene (since it contained an EcoRI restriction enzyme site) by digestion with the restriction enzyme XbaI, after which the vector fragment was isolated and then religated to form the plasmid pNG3/Vkss-HuCk. This intermediate vector was digested with the enzymes SacII and EcoRI, which excised the HuCk gene fragment. The digest was then loaded on a 1% agarose gel and the excised fragment separated from the remaining vector after which the vector DNA was cut from the gel and purified. Two oligonucleotides CME 00261 and CME 00262 (SEQ ID NO: 1 and 2) were designed and synthesised. These two oligonucleotides were hybridised by adding 200 pmoles of each oligonucleotide into a total of 30 µl of H$_2$O, heating to 95° and allowing the solution to cool slowly to 30°. 100 pmoles of the annealed DNA product was then ligated directly into the previously prepared vector and the ligation mix transformed into E.coli. In the clones obtained, the introduction of the DNA "cassette" produced a new polylinker sequence in preparation for the subsequent CPG2 gene cloning to produce the vector pNG3-Vkss.

The CPG2 structural gene encoding amino acid residues Q26-K415 inclusive was amplified by PCR using appropriate DNA oligonucleotide primers and standard PCR reaction conditions. The reaction product was analyses using a 1% agarose gel, a band of the expected size (approximately 12000 b.p.) was excised, purified and eluted in 20 µl H$_2$O. This material was then digested using the restriction enzyme SacII, after which the reaction was loaded on a 1% agarose gel and a band of the expected size (approximately 250 b.p.) was excised and subsequently purified. This fragment was ligated into the plasmid vector pNG3VKss, which had been previously digested with the restriction enzyme SacII, dephosphorylated, run on a 1% agarose gel, the linearised vector band excised, purified, and the ligation mix transformed into E.coli. The resultant clones were analysed for the presence and orientation of the CPG2 SacII fragment by DNA restriction analysis using the enzymes BglII and FseI. Clones which appeared to have a fragment of the correct size and orientation were confirmed by DNA sequencing. This intermediate plasmid was called pNG3-Vkss-SacIICPG2frag. This plasmid was digested with the restriction enzymes by AgeI and EcoRI, dephosphorylated and the vector fragment isolated. The original CPG2 gene PCR product was also digested with AgeI and EcoRI, an approximately 1000 bp. fragment isolated, ligated and transformed into E.coli. The resulting clones were analysed for a full length CPG2 gene (approximately 1200 bp.) by digestion with the restriction enzymes HindIII and EcoRI; clones with the correct size insert were sequenced to confirm identity. Finally, this plasmid (pNG3/Vkss-CPG2) was digested with XbaI, dephosphorylated, a vector fragment isolated and the XbaI Neomycin gene fragment (approximately 1000 bp. which had also been isolated in the earlier stages) religated into the plasmid and transformed into E.coli. Resulting clones were checked for the presence and orientation of the Neomycin gene by individual digests with the enzymes XbaI and EcoRI. This vector was called pNG3-Vkss-CPG2-NEO.

d) Construction of the CPG2 R6 Variant

The plasmid pNG3-Vkss/CPG2-NEO was used as a template for the PCR mutagenesis of the CPG2 gene in order to mutate 3 potential glycosylation sites which had been identified within the natural bacterial enzyme sequence. The putative amino acid glycosylation sites (N-X-T/S) were observed at positions 222 (N-I-T), 264 (N-W-T), and 272 (N-V-S) using the positional numbering published by Minton, N. P. et al., in Gene, (1984) 31, 31–38. The asparagine residue (N) of the 3 glycosylation sites was mutated to glutamine (Q) thus negating the glycosylation sites to avoid any glycosylation events affecting CPG2 expression or enzyme activity.

A PCR mutagenesis technique in which all 3 sites were mutated in a single reaction series was used to create the CPG2 R6 gene variant. The vector pNG3/Vkss/CPG2-NEO was used as the template for three initial PCR reactions. Reaction R1 used synthetic oligonucleotide sequence primers CME 00395 and CME 00397 (SEQ ID NOS: 3 and 4), reaction R2 used synthetic oligonucleotide sequence primers CME 00395 and CME 00399 (SEQ ID NOS: 3 and 5) and reaction R3 used synthetic oligonucleotide sequence primers CME 00396 and CME 00400 (SEQ ID NOS: 6 and 7). The products of PCR reactions R1 and R2 contained the mutated 222 and 264+272 glycosylation sites respectively, with the R3 product being a copy of the C-terminal segment of the CPG2 gene. The R2 and R3 products (R2 approximately 750 bp; R3 approximately 360 bp), after agarose gel separation and purification, were joined in a further PCR reaction. Mixtures of varying amounts of the products R2 and R3 were made and PCR reactions performed using the synthetic oligonucleotides CME 00395 and CME 00396 (SEQ ID NOS: 3 and 6). The resulting product R4 (approximately 1200 bps) was again PCR amplified using the oligonucleotides CME 00398 and CME 00396 (SEQ ID NOS: 8 and 6). The resulting product R5 (approximately 600 bp.) was joined to product R1 (approximately 620 b.p.) in a final PCR reaction performed using the oligonucleotides CME 00395 and CME 00396 (SEQ ID NOS: 3 and 6). The resulting PCR product R6 (approximately 1200 bp), which now contained all three mutated glycosylation sites, could be cloned (after digestion with the restriction enzymes AgeI and BsrGI and isolation of the resultant fragment) into the vector pNG3/Vkss-CPG2-Neo.(which had been previously cut with the restriction enzymes AgeI and Bsr GI and subsequently isolated). This created the desired DNA (SEQ ID NO: 9) encoding CPG2/R6 protein sequence (SEQ ID NO: 10) within the expression vector pNG3/Vkss-CPG2 R6-NEO.

e) Construction of the A5B7 Heavy Chain Fd-CPG2 Fusion Protein Gene

The heavy chain antibody fragment and the CPG2 enzyme genes were both obtained by PCR amplification of plasmid templates. The plasmid pNG4/A5B7VH-IgG2CH1' was amplified with primers CME 00966 (SEQ ID NO: 11) and CME 00969 (SEQ ID NO: 12) to obtain the A5B7 Fd component (approximately 300 b.p.) and the plasmid pNG3/Vkss/CPG2 R6-NEO was amplified with primers CME 00967 (SEQ ID NO: 13) and CME 00968 (SEQ ID NO: 14) to obtain the enzyme component (approximately 1350 b.p.). In each case the PCR reaction product was loaded and separated on a 1% agarose gel, a band of the correct product size excised, subsequently purified and eluted in 20 μl $H_2O$.

A further PCR reaction was performed to join (or splice) the two purified PCR reaction products together. Standard PCR reaction conditions were used with varying amounts (between 0.5 to 2 μl) of each PCR product but utilising 25 cycles (instead of the usual 15 cycles). The reaction product was analysed using a 1% agarose gel and a band of the expected size (approximately 1650 b.p.) was excised, purified and eluted in 20 μl $H_2O$. This material was then digested using restriction enzymes NheI and BamHI, after which a band of the expected size (approximately 1600 b.p.) was recovered and purified. The vector pNG4/A5B7VH-IgG2CH1' was prepared to receive the above PCR product by digestion with restriction enzymes NheI and BamHI, after which the DNA was dephosphorylated and the larger vector band was separated from the smaller NheI/Bam HI fragment. The vector band was recovered, purified and subsequently the similarly restricted PCR product was ligated in to the prepared vector and the ligation mix transformed into *E. coli*. DNA was prepared from the clones obtained and subsequently sequenced to confirm the fusion gene sequence. A number of the clones were found to be correct and one of these clones (designated R2.8) was re-named pNG4/A5B7VH-IgG2CH1/CPG2 R6 (SEQ ID NO: 15 and SEQ ID NO: 16).

f) Co-transfection, Transient Expression

The plasmids pNG4/A5B7VH-IgG2CH1/CPG2 R6 (encoding the antibody chimaeric Fd-CPG2 fusion protein) and pNG3/A5B7VK-HuCK-NEO (encoding the antibody chimaeric light chain; SEQ ID NO: 17 and SEQ ID NO: 18) were co-transfected into COS-7 cells using a LIPOFECTIN™ based procedure as described below. COS7 cells are seeded into a 6 well plate at $2 \times 10^5$ cells/2 ml/well, from a subconfluent culture and incubated overnight at 37°, 5% $CO_2$. A LIPOFECTIN™/serum free medium mix is made up as follows: 12 ml LIPOFECTIN™ plus 200 ml serum free medium and incubated at room temperature for 30 minutes. A DNA/serum free medium mix is made up as follows: 4 mg DNA (2 mg of each construct) plus 200 ml serum free medium. 200 ml of the LIPOFECTIN™/serum free medium mix is then added to the DNA mix and incubated for 15 minutes room temperature. 600 ml of serum free medium was then added to each sample. The cells were washed once with 2 ml serum free medium and then the 1 ml LIPOFECTIN™/DNA mix is added to the cells and incubated for 5 hours, 37°, 5% $CO_2$. The LIPOFECTIN™/DNA mix was removed from the cells and normal growth media added after which the cells were incubated for 72 hours, 37°, 5% $CO_2$. The cell supernatants were harvested.

g) Analysis of Antibody-Enzyme Fusion Protein

The supernatant material was analysed for the presence of antibody fusion protein using a CEA-binding ELISA using an anti human kappa light chain reporter antibody (for presence of antibody), a CEA-binding ELISA using an anti-CPG2 reporter antibody (for presence of CEA bound CPG2 fusion protein), a HPLC based CPG2 enzyme activity assay (to measure specific CPG2 activity) and SDS/PAGE followed by Western blotting (using either anti human kappa light chain reporter or anti CPG2 reporter antibodies) to detect expressed material.

The HPLC based enzyme activity assay clearly showed CPG2 enzyme activity to be present in the cell supernatant and both the anti-CEA ELISA assays exhibited binding of protein at levels commensurate with a bivalent A5B7 antibody molecule. The fact that the anti-CEA ELISA detected with an anti-CPG2 reporter antibody also exhibited clear CEA binding indicated that not only antibody but also antibody-CPG2 fusion protein was binding CEA.

Western blot analysis with both reporter antibody assays clearly displayed a fusion protein subunit of the expected approximately 90 kDa size with no degradation or smaller products (such as Fab or enzyme) observable.

Since CPG2 is known only to exhibit enzyme activity when it is in a dimeric state and since only antibody enzyme fusion protein is present, this indicates that the 90 kDa fusion protein (seen under SDS/PAGE conditions) dimerises via the natural CPG2 dimerisation mechanism to form a 180 kDa dimeric antibody-enzyme fusion protein molecule (FIG. 2a) in "native" buffer conditions. Furthermore, this molecule exhibits both CPG2 enzymatic activity and CEA antigen binding properties which do not appear to be significantly different in the fusion protein compared with enzyme or antibody alone.

h) Use of Expressed Fusion Protein and CPG2 Prodrug in an In Vitro Cytotoxicity Assay An in vitro cell killing assay was performed in which the $(A5B7-CPG2\ R6)_2$ fusion protein was compared to a "conventional" A5B7 $F(ab')_2$-CPG2 conjugate formed through linking A5B7 $F(ab')_2$ to CPG2 with a chemical heterobifunctional reagent. In each case material displaying equal amounts of CPG2 enzyme activity or equal amounts of antibody-CPG2 protein were incubated with LoVo, CEA bearing, tumour cells. The cells were then washed to remove unbound protein material and subsequently resuspended in medium containing a CPG2 phenol prodrug (PGP, see Example 2 below) for a period of 1 hr, after which the cells were washed, resuspended in fresh media and left to proliferate for 4 days. Finally the cells were treated with SRB stain and their numbers determined.

The results obtained clearly showed that the (A5B7-CPG2 R6)$_2$ fusion protein (together with prodrug) caused at least equivalent cell kill and resulted in lower numbers of cells at the end of the assay period than the equivalent levels of A5B7 F(ab)$_2$-CPG2 conjugate (with the same prodrug). Cell killing (above basal control levels) can only occur if the prodrug is converted to active drug by the CPG2 enzyme (and since the cells are washed to remove unbound protein, only cell bound enzyme will remain at the stage where the prodrug is added). Thus this experiment shows that at least as much of the A5B7-CPG2 R6 fusion protein remains bound compared with conventional A5B7 F(ab)$_2$-CPG2 conjugate as a greater degree of cell killing (presumably due to higher prodrug to drug conversion) occurs.

i) Construction of a Coexpression Fusion Protein Vector for use in Transient and Stable Cell Line Expression For a simpler transfection methodology and the direct coupling of both expression cassettes to a single selection marker, a co-expression vector for fusion protein expression was constructed using the existing vectors pNG4/A5B7VH-IgG2CH1/CPG2 R6 (encoding the antibody Fd-CPG2 fusion protein) and pNG3/A5B7VK-HuCK-NEO (encoding the antibody light chain). The pNG4/A5B7VH-IgG2CH1/CPG2 R6 plasmid was first digested with the restriction enzyme ScaI, the reaction loaded on a 1% agarose gel and the linear vector band excised from the gel and purified. This vector DNA was then digested with restriction enzymes BglII and BamHI, the reaction loaded on a 1% agarose gel, the desired band (approximately 2700 bp) recovered and purified. The plasmid pNG3/A5B7VK-HuCK-NEO was digested with the restriction enzyme BamHI after which the DNA was dephosphorylated then subsequently loaded on a 1% agarose gel and the vector band excised from the gel and purified. The heavy chain expression cassette fragment was ligated in to the prepared vector and the ligation mix transformed into *E. coli*. The orientation was checked by a variety of restriction digests and clones selected which had the heavy chain cassette in the same direction as that of the light chain. These plasmids were termed pNG3-A5B7-CPG2/R6-coexp.-NEO.

j) Gene Switches for Protein Expression

It is foreseen that in vitro expression of CPG2 and CPG2 fusion proteins in mammalian cells may degrade media folates leading to slow cell growth or cell death. The high activity of the CPG2 enzyme is likely to make such a folate deficiency difficult to overcome by media supplementation. However, it is thought that in the case of CPG2 or CPG2 fusion protein expression from mammalian cells in vivo, it is unlikely that such problems will occur, since the cells would be constantly replenished with all growth requirements by the normal circulatory and cellular mechanisms.

A number of options to avoid possible in vitro folic acid depletion problems have been considered. One of these solutions involve the use of tightly controlled but inducible gene switch systems such as the "TET on" or "TET off" switches (Grossen, M. et al (1995) Science 268: 1766–1769) or the ecdysone/muristerone A switch (No, D. et al (1996) PNAS 93 :3346–3351). Such systems enable precisely controlled expression of a gene of interest and allow stable transformation of mammalian cells with genes encoding toxic or potentially deleterious expression products. A gene switch would allow recombinant stable cell lines incorporating CPG2 fusion genes to be potentially more easily established, maintained and expanded for protein expression and seeding cultures for in vivo tumour growth studies.

EXAMPLE 2
HCT116 Tumour Cells Expressing the Antibody-enzyme Fusion Protein are Selectively Killed in vitro by a Prodrug HCT 116 colorectal tumour cells (ATCC CCL 247) transfected with the antibody-CPG2 fusion protein gene of Example 1 can be selectively killed by a prodrug that is converted by the enzyme into an active drug.

To demonstrate this, control non-transfected HCT116 cells or HCT116 cells transfected with the antibody-CPG2 fusion protein gene, are incubated with either the prodrug, 4-[N,N-bis(2-chloroethyl)amino]-phenoxycarbonyl-L-glutamic acid (PGP; Blakey et al, Br. J. cancer 72, 1083, 1995) or the corresponding drug released by CPG2, 4-[N, N-bis(2-chloroethyl)amino] phenol. PGP prodrug and drug over the concentration range of $5 \times 10^{-4}$ to $5 \times 10^{-8}$ M are added to 96 well microtitre plates containing 1000–2,500 HCT116 cells/well, for 1 hr at 37°. The cells are then washed and incubated for a further three days at 37°. After washing to remove dead cells, TCA is then added and the amount of cellular protein adhering to the plates is assessed by addition of SRB dye as described by Skehan et al (J. Natl. Cancer Inst. 82, 1107, 1990). Potency of the prodrug and drug is assessed by the concentration required to inhibit cell growth by 50% (IC$_{50}$).

Treatment of non-transfected or transfected HCT116 cells with the drug results in an IC$_{50}$ of approximately 1 $\mu$M. In contrast, the PGP prodrug results in an IC$_{50}$ of approximately 200 $\mu$M on non-transfected cells and approximately 1 $\mu$M on transfected cells. These results demonstrate that the transfected cells which express the antibody-CPG2 fusion protein can convert the PGP prodrug into the more potent active drug while non-transfected HCT116 cells are unable to convert the prodrug. Consequently the transfected HCT116 cells are over 100 fold more sensitive to the PGP prodrug in terms of cell killing compared to the non-transfected HCT116 cells. (See Example 1j) for issues involving possible folic acid depletion in cells).

These studies demonstrate that transfecting tumour cells with a gene for an antibody-enzyme fusion protein can lead to selective tumour cell killing with a prodrug.

EXAMPLE 3
Anti-tumour Activity of PGP Prodrug in HCT116 Tumours Expressing the Antibody-CPG2 Fusion Protein The anti-tumour activity in vivo of the PGP prodrug in HCT116 tumours expressing the antibody-CPG2 fusion protein can be demonstrated as follows. HCT116 tumour cells transfected with the antibody-CPG2 fusion protein gene or control non-transfected HCT116 tumour cells are injected subcutaneously into athymic nude mice ($10^7$ tumour cells per mouse). When the turnours are 5–7 mm in diameter the PGP prodrug is administered i.p. to the mice (3 doses at hourly intervals over 2 h in dose ranges of 5–25 mg kg$^{-1}$). The anti-tumour effects are judged by measuring the length of the tumours in two directions and calculating the tumour volume using the formula:

$$\text{Volume} = \pi/6 \times D^2 \times d$$

where D is the larger diameter and d is the smaller diameter of the tumour.

Tumour volume is expressed relative to the tumour volume at the time the PGP prodrug is administered. The anti-tumour activity is compared to a control group receiving either transfected or non-transfected tumour cells and PBS (170 mM NaCl, 3.4 mM KCl, 12 mM $Na_2HPO_4$ and 1.8 mM $KH_2PO_4$, pH 7.2) instead of the PGP prodrug.

Administration of PGP to HCT116 tumours established from transfected HCT116 cells results in a significant anti-tumour effect as judged by the PGP treated tumours decreasing in size compared to the PBS treated tumours and it taking a significantly longer time for the PGP treated tumours to reach 4 times their initial tumour volume compared to PBS treated tumours. In contrast, administration of PGP to HCT116 tumours established from non-transfected cells resulted in no significant anti-tumour activity.

Similar studies can be used to demonstrate that the antibody-enzyme gene delivered in an appropriate vector to established HCT116 tumours produced from non-transfected HCT116 cells when used in combination with the PGP prodrug can result in significant anti-tumour activity. Thus non-transfected HCT116 cells are injected into athymic nude mice ($1 \times 10^7$ tumour cells per mouse) and once the tumours are 5–7 mm in diameter the vector containing the antibody-enzyme fusion protein gene is injected intra-tumourally. After 1–3 days to allow the antibody-enzyme fusion protein to be expressed by and bind to the HCT116 tumour cells, the PGP prodrug is administered as described above. This results in significant anti-tumour activity compared to control mice receiving PBS instead of PGP prodrug.

EXAMPLE 4
Improved Transfection of Adherent Cell Lines Using Supplemented FAS Media and/or V-79 Feeder Cells It was foreseen that in vitro expression of CPG2 and CPG2 fusion proteins in mammalian cells may degrade media folates leading to slow cell growth or cell death. FAS (folinic acid supplemented) media described herein was developed for CPG2 and CPG2 fusion protein expressing cell lines in order to better support the growth of such cell lines.

In preparation for transfection, adherent cell lines were cultured in normal DMEM edia and passaged at least three times before transfection. V-79 (hamster lung fibroblast, obtained from MRC Radiobiology Unit, Harwell, Oxford, United Kingdom) feeder cells were cultured in normal DMEM media and passaged three times before use. For the transfection, a viable count (using a haemocytometer/trypan blue staining) of the adherent cells was made and the cells plated out at $2 \times 10^5$ cells per well into a 6 well plate (Costar 3516) and left for 18–24 hours for the cells to re-adhere.

For each individual transfection, 20 $\mu$l of LIPOFECTIN™ was added to 80 $\mu$l serum free medium and left at room temperature for 30 minutes. Plasmid DNA (2 $\mu$g) of interest was added to 100 $\mu$l serum free medium and subsequently added to the LIPOFECTIN™ mix and left for a further 15 minutes. The individual 6 well plates were washed with 2 ml serum free medium per well to remove any serum and replaced with 800 $\mu$l of fresh serum free medium. The 200 $\mu$l DNA/LIPOFECTIN™/serum free medium mixes which had been previously prepared were then added to each well of cells. The plates were incubated at 37° for 5 hours, the media removed and 2 ml of fresh normal media added and incubated for a further 48 hours. The transfected cells in the 6 well plate were scraped free, the cell suspension removed and centrifuged. All the supernatant was removed and the cell pellet resuspended in 20 ml of the appropriate fresh growth media (e.g. FAS DMEM media) containing the appropriate selective agent for the transfected DNA (e.g. G418). Aliquots (200 $\mu$l) were plated per well into a 96 well plate ($1.25 \times 10^4$ cells per well).

To enhance clone expansion, fibroblast feeder cells may be added to the transfected cells. Semi-confluent V-79 feeder cells were trypsinised and a viable count performed. The cells were resuspended to $1 \times 10^6$ cells /ml in a sterile glass container, irradiated using a Caesium source by exposure to 5000 rads over 12 minutes. The cells can then be stored at 4° for 24–48 hours (irradiated cells are metabolically active but will not divide, and so can act as "feeders" for other cells without contaminating the culture). The feeder cells should be plated out at $4 \times 10^4$ cells per well in a 96 well plate to produce a confluent layer for the emerging recombinant clones. Feeder cells initially adhere to the plate but with time detach and float off into the media, leaving the any recombinant clone still attached to the well. Media changes (200 $\mu$l at time) are performed twice weekly to remove floating cells and replenish media. Colonies were allowed to develop for 10–14 days, then the supernatant screened by standard ELISA assay for fusion protein secretion.

To measure the expression rate in the case of the $(A5B7\text{-}CPG2)_2$ fusion gene constructs, recombinant cells were seeded out at $1 \times 10^6$ in 10 ml fresh normal culture media for exactly 24 hours. The supernatant was then removed, centrifuged to remove cell debris and assayed for fusion protein and enzyme activity by the ELISA and HPLC methods described above. The results for a number of recombinant $(A5B7\text{-}CPG2)_2$ fusion protein cell lines are shown below.

| Cell Line | Clone | ng/$10^6$cells/24 h |
|---|---|---|
| HCT 116 | F7 | 6550 |
|  | C12 | 3210 |
| HCT 116 | F6 | 15560 |
|  | C1 | 6151 |
|  | B3 | 4502 |
|  | A8 | 4650 |
|  | D5 | 630 |
|  | H9 | 610 |
|  | G11 | 2081 |
|  | H4 | 2380 |
|  | A4 | 1634 |
| LoVo | B9 | 8370 |
|  | C1 | 7350 |
|  | F12 | 2983 |
|  | C7 | 10770 |
|  | G10 | 4140 |
| Colo 320DM | B3 | 10540 |
|  | G4 | 4720 |
|  | B9 | 885 |
|  | B10 | 3090 |
|  | F12 | 35660 |

EXAMPLE 5
Construction of a Stable Inducible $(A5B7\text{-}CPG2)_2$ Fusion Protein Expressing Tumour Cell Line
a) Construction of an Inducible Fusion Protein Expression Vector To facilitate expression from a single inducible mammalian cell promoter, an IRES (Internal Ribosome Entry Site; see Y. Sugimoto et al., Biotechnology (1994), 12, 694–8) based version of the $(A5B7\text{-}CPG2)_2$ fusion protein was constructed. Construct pNG3 pNG3/A5B7VK-HuCK-NEO (A5B7 chimaeric light chain; described in Example 1b above) was used as a template for amplification of the light chain gene. The gene was amplified using oligonucleotides CME 3153 and CME 3231 (SEQ ID NOS 19 and 20). A PCR product of the expected size (approximately 700 b.p.) was purified. This product was then digested using the restriction enzymes EcoRI and BamHI and subsequently purified. The fragment was cloned into the Bluescript™ KS+vector (prepared to receive the fragment by digestion with the same restriction enzymes, EcoRI and BamHI) after which the DNA was dephosphorylated and the larger vector band purified. The similarly restricted PCR fragment ligated in to the prepared vector and the ligation mix was transformed into E. coli. DNA was prepared from the clones obtained and analysed by restriction digestion to check for insertion of PCR fragment. Appropriate clones were sequenced to confirm the gene sequence. A number of the clones with the correct sequence were obtained and one of these clones was given the plasmid designation ASB7 Bluescript™.

In a similar manner, the chimaeric A5B7 heavy chain was amplified by PCR from the plasmid pNG4/A5B7VH-IgG2CH1/CPG2 R6 (described in Example 1e above) using oligonucleotides CME 3151 and CME 3152 (SEQ ID NOS 21 and 22). A PCR reaction product of the expected size (approximately 1800 b.p.) was purified. This product was then digested using the restriction enzymes BamHI and Xba I after which the fragment band was purified. The fragment was also cloned into the Bluescript™ KS+vector which had been prepared to receive the above fragment by digestion with the same restriction enzymes, 10 BamHI and XbaI, after which the DNA was dephosphorylated and the larger vector band was purified. The similarly restricted PCR fragment was ligated in to the prepared vector and the ligation mix was transformed into E. coli. DNA was prepared from the clones obtained and analysed by restriction digestion to check for insertion of PCR fragment. Appropriate clones were sequenced to confirm the gene sequence. A number of the clones with the correct sequence were obtained and one of these clones was given the plasmid designation Bluescript™ Fd-CPG2 R6.

The IRES sequence was sourced from the vector pSXLC (described in Y. Sugimoto et al. Biotechnology (1994), 12, 694–8, and obtained from the authors). The IRES sequence was excised by digestion with the restriction enzymes BamHI and NcoI. A band of the expected size (approximately 500 b.p.) was purified and ligated into the Bluescript™ Fd-CPG2 R6 plasmid (which had previously been prepared by restriction with the same enzymes). The ligation mix was transformed into E. coli and DNA was prepared from the clones obtained. The DNA was analysed by restriction digestion to check for insertion of the fragment and appropriate clones were subsequently sequenced to confirm the gene sequence. A number of the clones with the correct sequence were obtained and one of these clones was given the plasmid designation Bluescript™ IRES Fd-CPG2 R6.

To facilitate later cloning steps, it was necessary to delete the Xba I site which had been carried over in the IRES fragment. This was performed by PCR mutagenesis with the oligonucleotide primers CME 3322 and CME 3306 (SEQ ID NOS: 23 and 24) and the Bluescript™ IRES Fd-CPG2 R6 as template DNA. A PCR reaction product of the expected size (approximately 500 b.p.) was purified, digested with the restriction enzymes BamHI and NcoI and ligated into the Bluescript™ IRES Fd-CPG2 R6 plasmid (which had previously been prepared by restriction with the same restriction enzymes). The ligation mix was transformed into E. coli and DNA was prepared from the clones obtained. The DNA was analysed by restriction digestion to check for insertion of the fragment and appropriate clones were subsequently sequenced to confirm the gene sequence. A number of the clones with the correct sequence were obtained and one of these clones was given the plasmid designation Bluescript™ IRES Fd-CPG2 R6-Xba del.

The A5B7 chimaeric light chain fragment was excised from the A5B7 Bluescript™ plasmid by digestion with the restriction enzymes EcoRI and BamHI. A band of the expected size (approximately 700 b.p.) was purified, ligated into the appropriately prepared Bluescript IRES Fd-CPG2 R6-Xba del plasmid and the ligation mix was transformed into E. coli. DNA was prepared from the clones obtained and analysed by restriction digestion to check for insertion of the fragment. Appropriate clones were subsequently sequenced to confirm the gene sequence. A number of the clones with the correct sequence were obtained and one of these clones was given the plasmid designation Bluescript™ A5B7 IRES Fd-CPG2 R6-Xba del. The complete IRES based A5B7 chimaeric fusion protein gene sequence is shown in SEQ ID NO: 52.

The IRES based A5B7 chimaeric fusion protein gene was then transferred to a tetracycline regulated expression vector. Vectors for the Tet On gene expression system were obtained from Clontech. The Tetracycline switchable expression vector pTRE (otherwise known as pHUD10-3, see Gossen et al. (1992), PNAS, 89, 5547–51) was prepared to accept the IRES based fusion protein cassette by digestion with the restriction enzymes EcoRI and XbaI, dephosphorylated and the larger vector band purified. The IRES gene cassette was excised from the Bluescript™ A5B7 IRES Fd-CPG2 R6-Xba del plasmid using the same restriction enzymes. The approximately 3000 b.p. fragment obtained was ligated in to the prepared vector and the ligation mix was transformed into E. coli. DNA was prepared from the clones obtained and analysed by restriction digestion to check for insertion of PCR fragment. Appropriate clones were subsequently sequenced to confirm the gene sequence. A number of the clones with the correct sequence were obtained and one of these clones was given the plasmid designation pHUD10-3/A5B7 IRES Fd-CPG2 R6.

b) Construction of a Stable Inducible Fusion Protein Expressing Cell Line

The standard lipofection transfection methodology (as described previously but without the use of feeder cells) was used to produce recombinant HCT116 tumour cell lines A co-transfection using 1 g of the pHUD10-3/A5B7 IRES Fd-CPG2 R6 plasmid and 1 µg of the pTet-On transactivator expressing plasmid (from the Clontech kit) was performed and positive clones selected using FAS media containing 750 µg G418/ml.

c) Induction Studies of Recombinant HCT116 Inducible Cell Lines

The clone cultures obtained were split in to duplicate 48 well plates, each containing $1 \times 10^6$ cells. The cells were grown for 48 h with one of the plates induced with 2 µg/ml doxycycline and the other acting as an non-induced control. Expression of the $(A5B7\text{-}CPG2)_2$ fusion protein in the cell supernatant was tested using the ELISA/Western blot assays described in Example 1g. The results indicated that induction of fusion protein from the inducible cell line by use of doxycycline could be clearly demonstrated, for example one of the clones obtained (F11), the induced cells produced 120 ng/ml of fusion protein in the supernatant whereas the non-induced cells produced only background levels of fusion protein (below 1 ng/ml).

EXAMPLE 6

Cell Based ELISA Assay of Secreted Fusion Protein Material

Cells were seeded into 96 well plates (Becton Dickinson Biocoat™ poly-D-Lysine, 35-6461) at a density of $1 \times 10^4$ cells per well in 100 µl normal culture media and left about 40 h at 37°. 100 µl of 6% formaldehyde was diluted in DMEM and left for 1 hour at 4°. Plates were centrifuged and washed 3 times in PBS containing 0.05% Tween™ by immersion soaking (first two washes for 2 minutes and the final wash for 5 minutes).

100 μl of doubling dilutions of cell culture supernatant containing fusion protein or chimeric A5B7 anti-CEA were added to each well as appropriate and the plates incubated overnight at 4°. The plates were washed as described above and, in the case of chimaeric fusion proteins. 100 μl of 1:1000 dilution of HRP labelled anti-human kappa antibody (Sigma A-7164) was added and incubated for 2 hours at room temperature (an anti-CPG2 detection methodology can be used in the case of murine scFv fusion proteins). The plates were washed as described above and HRP detected using OPD substrate (Sigma P-8412). Colour was allowed to develop for about 5 min, stopped with 75 μl per well of 2M $H_2SO_4$ and OD read at 490 nm.

In the case of the $(A5B7-CPG2)_2$ fusion protein, material was produced in the supernatant from recombinant Colo320DM tumour cells (CEA-ve). The fusion protein content was measured by use of the CEA ELISAs described above. Increasing amounts of fusion protein were added to a number of CEA negative cell lines and the CEA positive LoVo parental line. The results shown in FIG. 3 clearly show that only the CEA positive line shows increased levels of binding with increasing amounts of added fusion protein whereas the CEA negative cell lines show only constant background binding levels throughout. This clearly demonstrates that the fusion protein specifically binds and is retained on CEA positive Lovo cells.

Figure 4:
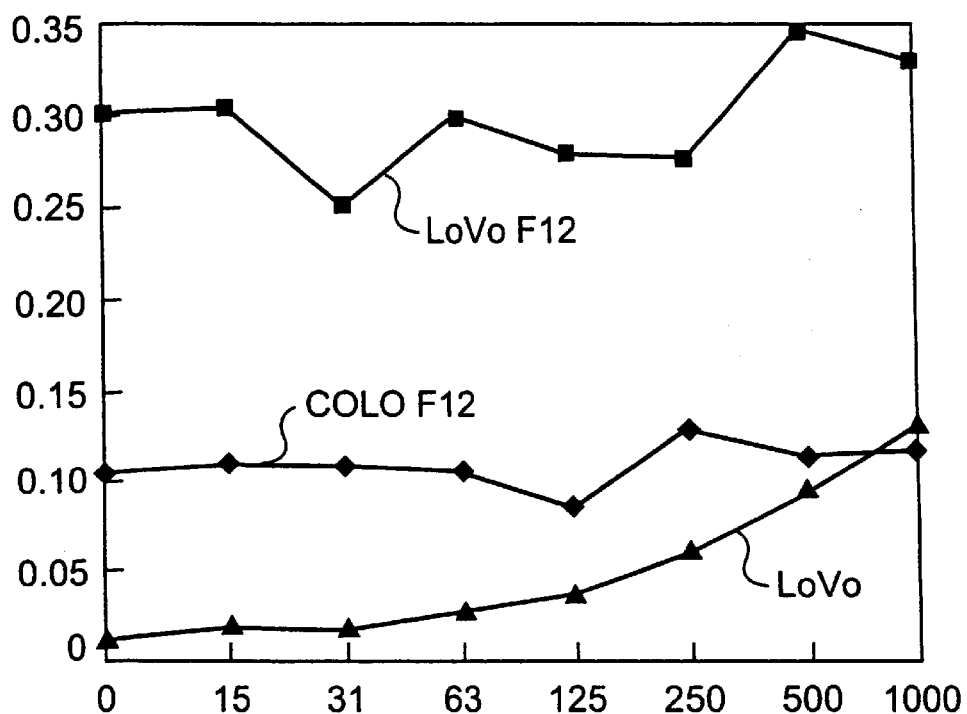
FIG. 4 shows retention of secreted fusion protein to recombinant LoVo tumour cells. The vertical axis represents optical density readings measured at 490 nm and the horizontal axis the amount of added anti-CEA antibody (IIE6) measured in ng/ml of protein. The experiment was performed as described in Example 7 using three different cell lines, recombinant LoVo and Colo320DM lines (which themselves secrete fusion protein) and a contol parental LoVo line which does not secrete fusion protein. Firstly, the cell lines were fixed and washed to remove the existing supernatant and any unbound material after which increasing concentrations of the anti-CEA antibody (IIE6) were added to the fixed cells. The assay was developed as described in the text to determine the level of retention of any secreted material and whether further added antibody would increase the signal. The results showed that whithout added anti-CEA antibody the control parental Lovo line exhibited only a backgroundOD490 nm reading (as expected) whereas the recombinant LoVo line gave a very strong OD 490 nm reading indicating that the fusion protein material was being retained on the CEA positive LoVo cells. The CEA negative recombinant Colo320DM gave a much weaker reading than the LoVo cells but the signal was higher than background (possibly due to none fixing of the secreted antibody early in the assay method). Increasing concentrations of the anti-CEA antibody (IIE6) added to the fixed cells showed a dose related response in the case of the parental LoVo cells thus indicating that they are CEA positive and can bind CEA binding material (such as the fusion protein if present or added). The recombinant Colo320DM and LoVo cells showed little increase in overall OD490 signal with increasing amounts of added antibody with the exception of the LoVo cells which appear to show a slight response at the highest antibody dose. Since the recombinant Colo320DM are CEA negative no increase in signal due to anti-CEA antibody the results for these cells would be expected. In the case of the recombinant LoVo cells the addition signal due the amounts of antibody added in this assay may be swamped except at the highest dose due to the relative strength of the original signal.

EXAMPLE 7
Recombinant LoVo Tumour Cells Expressing Antibody-enzyme Fusion Protein Exhibit Retention of the Fusion Protein on the Cell Surface LoVo colorectal tumour cells transfected with the $(A5B7-CPG2)_2$ fusion protein gene have been shown both to secrete and to retain the fusion protein on their cell surface. This can be demonstrated by comparing parental and recombinant fusion protein expressing LoVo cells under the conditions set out in the cell based ELISA assay of secreted fusion protein (FIG. 4). On development of the colour reaction it could be seen that the recombinant LoVo cells had retained the expressed fusion protein (by showing a high level of colour). In control experiments, using Colo320DM fusion protein expressing cells, the assay showed some retention of the expressed fusion protein (probably non-specific) and the parental LoVo cells only exhibited background activity. Positive controls in which CEA binding antibody was added to test recombinant fusion protein expressing tumour cells and to the parental LoVo controls resulted in a signal being obtained from the parental LoVo (thus demonstrating that CEA was present on the parental cells) but no increased signal from the Colo320DM (CEA negative). The recombinant LoVo cells still gave such a strong initial signal that the added antibody made little difference to the overall signal obtained, which was considerably higher than any of the control experiments. Thus it appears that anti-CEA antibody enzyme-CPG2 fusion protein secreted from CEA positive tumour cell lines bind to the surface of the cells (via CEA) whereas the same protein expressed from CEA negative tumours shows no such binding.

EXAMPLE 8
LoVo Tumour Cells Expressing the Antibody-enzyme Fusion Protein are Selectively Killed in vitro by a Prodrug LoVo colorectal tumour cells, transfected with the $(A5B7-CPG2)_2$ fusion protein gene, can be selectively killed by a prodrug that is converted by CPG2 enzyme into an active drug.

To demonstrate this control non-transfected LoVo cells or LoVo cells transfected with an antibody-CPG2 fusion protein gene are incubated with either the prodrug, 4-[N,N-bis (2-chloroethyl)amino]-phenoxycarbonyl-L-glutamic acid (PGP; Blakey et al, (1995) Br. J. cancer 72, p1083) or the corresponding drug released by CPG2, 4-[N,N-bis(2-chloroethyl)amino] phenol as described in Example 2 with HCT116 cells.

The transfected cells which express the antibody-CPG2 fusion protein can convert the PGP prodrug into the more potent active drug while non-transfected LoVo cells are unable to convert the prodrug.

These studies demonstrate that transfecting tumour cells with a gene for an antibody-enzyme fusion protein can lead to selective tumour cell killing with a prodrug.

EXAMPLE 9
Establishment of Fusion Protein Expressing LoVo Tumour Xenografts in Athymic Mice Recombinant LoVo fusion protein $(A5B7-CPG2)_2$ expressing tumour cells or mixes of recombinant and parental LoVo cells were injected subcutaneously into athymic nude mice ($10^7$ tumour cells per mouse). The tumour growth rates for both 100% recombinant and 20%: 80% mixes of recombinant:parental LoVo cells were compared to those of parental cell only tumours. No significant differences were seen in the observed growth curves obtained showing no corrections were required during comparisons between the cell lines. The tumour growth rates observed showed that in each case for the xenograft tumours to reach a size of 10×10 mm takes about 12 days.

EXAMPLE 10
Determination of Enzyme Activity in Tumour Xenograft Samples

To act as a standard for the assay, a CPG2 enzyme standard curve was prepared in 20% homogenate of normal tumour (parental cell tumour). Subsequent dilutions of samples were made in the same 20% homogenate of normal tumour.

Excised tumour tissue is removed from −80° storage (previously flash frozen in liquid nitrogen) and allowed to thaw. Any residual skin tissue was removed before the tumour was cut up in to small fragments with a scalpel. The tumour tissue was transferred to a preweighed tube and the weight of tumour tissue measured. PBS containing 0.2 mM $ZnCl_2$ solution was added to each tumour sample to give a 20% (w/v) mix, homogenised and placed on ice. Dilutions of sample tumours (in 20% normal tumour homogenate) were prepared e.g. neat, 1/10, 1/20 and 1/40.

For the standard curve, dilutions of CPG2 enzyme were made to the following concentrations to a final volume of 400 μl. Similarly, 400 μl of each of the recombinant tumour sample dilutions were also prepared. After equilibration to 30°, 4 μl of 10 mM methotrexate (MTX) solution was added. The reaction was stopped after exactly 10 minutes by adding 600 μl ice cold methanol+0.2% TFA, centrifuged and the supematant collected. The substrate and product in the supernatant were then separated by HPLC (using a Cation Exchange Column, HICROM™ S5SCX-100 A, mobile phase=60% methanol, 40% 60 mM ammonium formate/ 0.1% TFA, detection 300 nm). To calculate enzyme activity in the tumour tissue, the standard curve was plotted as units of area of methotrexate metabolite (the standards are such that only 20–30% of the substrate is metabolised so ensuring this is not rate limiting). The test samples were analysed by comparing the unit area of metabolite against the standard curve and then multiplying by the dilution factor. Finally, making the working assumption that 1 ml=1 g the results were multiplied by 5 (as the samples were originally diluted to a 20% homogenate).

Results obtained with 20% recombinant: 80% parental LoVo cells expressing (A5B7 Fab-CPG2)$_2$ fusion protein showed the following results: tumours taken at day 5 had an average enzyme activity=0.26 U/g (range between 0.18–0.36 U/g) and at day 12 had an average enzyme activity=0.65 U/g (range between 0.19–1.1 U/g).

EXAMPLE 11
Determination Enzyme Activity in Plasma Samples

To act as a standard for the assay, a CPG2 enzyme standard curve was prepared in 20% normal plasma to the following concentrations: 0.2, 0.4, 0.6, 0.8 and 1.0 U/ml. Similarly all test plasma samples were also diluted to 20% normal plasma. Further dilutions of these samples e.g. neat 1/10, 1/20 and 1/50 were also made using 20% normal serum. 200 µl aliquots of each CPG2 standard and test sample dilutions were equilibrated to 30°. 2 µl of 10 mM MTX was added to each of the tubes and mixed well. to 30°. The reaction was stopped after exactly 10 minutes (to increase the sensitivity of the assay the incubation time can be increased to 30 minutes) by adding 500 µl ice cold methanol+0.2% TFA and assayed for product using HPLC detection as described above in Example 10.

No activity was seen in the plasma except in the rare cases when the level of enzyme activity in the tumour exceeded 2.0 U/g, in which case the plasma enzyme levels were measured in the range of 0.013 to 0.045 U/ml.

EXAMPLE 12
Anti-tumour Activity of PGP Prodrug in LoVo Tumours Expressing the Antibody-CPG2 Fusion Protein Recombinant LoVo (A5B7-CPG2)$_2$ fusion protein expressing tumour cells or mixes of recombinant and parental LoVo cells were injected subcutaneously into athymic nude mice as described in Example 9.

When the tumours are 5–7 mm in diameter the PGP prodrug is administered i.p. to the mice (3 doses in DMSO/ 0.15 M sodium bicarbonate buffer at hourly intervals over 2 h in dose ranges of 40–80 mg kg$^{-1}$).

Anti-tumour effects are judged by measuring the length of the tumours in two directions and calculating the tumour volume using the formula $$\text{Volume} = \pi/6 \times D^2 \times d$$

where D is the larger diameter and d is the smaller diameter of the tumour. Tumour volume may be expressed relative to the tumour volume at the time the PGP prodrug is administered or alternatively the median tumouT volumes may be calculated. The anti-tumour activity is compared to control groups receiving either transfected or non-transfected tumour cells and buffer without PGP prodrug.

Figure 5:
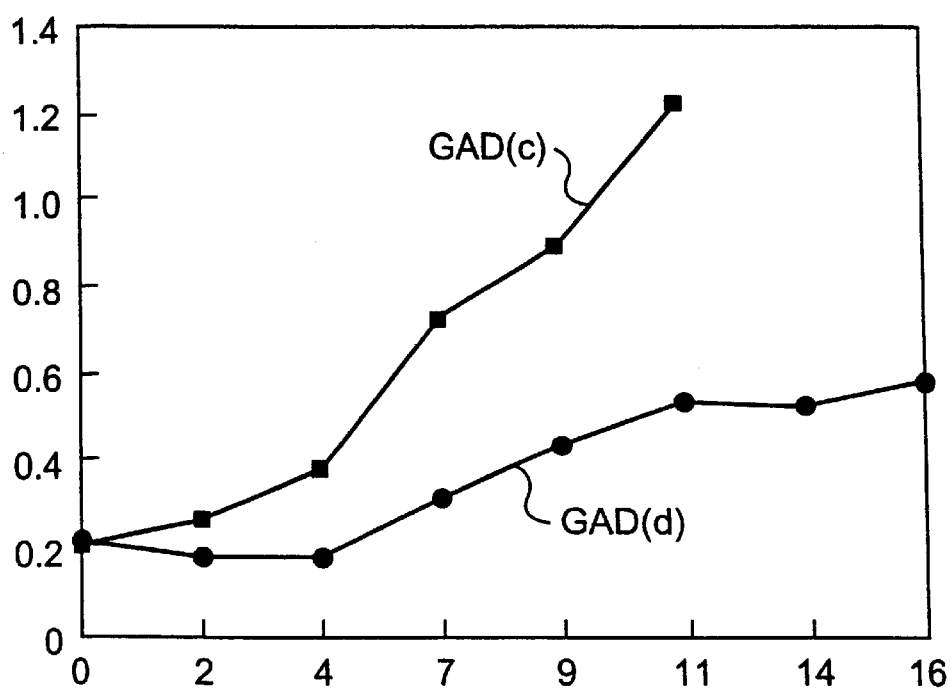
FIG. 5 shows retention of secreted fusion protein to recombinant LoVo tumour cells. The vertical axis represents median tumour volume ($cm^3$) and the horizontal axis time in day after dosing of the prodrug. The experiment was performed as described in Example 12 using 60 mg/kg doses of prodrug. The results show that the control GAD(c) (none prodrug treated) tumours grew to 6 times their initial size by 11 days (post-dose day) at which time the tumours were harvested. The prodrug treated tumours GAD(d) show a significantly slower growth rate and by day 16 (post-dose day) have only reached 3 times their initial size. This data indicates at least an 11 day tumour growth delay.

Administration of PGP to LoVo tumours established from recombinant LoVo cells or recombinant Lovo/Parental LoVo cell mixes results in a significant anti-tumour effect as shown by the PGP treated tumours decreasing in size compared with controls and it taking a significantly longer time for the PGP treated tumours to reach 4 times their initial tumour volume compared with controls (FIG. 5). Administration of PGP to LoVo tumours established from non-transfected cells resulted in no significant anti-tumour activity.

Similar studies can be used to demonstrate that the antibody-enzyme gene delivered in an appropriate gene delivery vector to established LoVo tumours produced from non-transfected parental LoVo cells when used in combination with the PGP prodrug can result in significant anti-tumour activity. Thus non-transfected LoVo cells are injected into athymic nude mice (1×10$^7$ tumour cells per mouse) and once the tumours are 5–7 mm in diameter the vector containing the antibody-enzyme fusion protein gene is injected intra-tumourally. After 1–3 days to allow the antibody-enzyme fusion protein to be expressed by, and bind to, the LoVo tumour cells, the PGP prodrug is administered as described above. This results in significant anti-tumour activity compared with controls.

EXAMPLE 13
Construction of an (806.077 Fab-CPG2)$_2$ Fusion Protein

The construction of a (806.077 Fab-CPG2)$_2$ enzyme fusion was planned with the aim of obtaining a bivalent human carcinoembryonic antigen (CEA) binding molecule which also exhibits CPG2 enzyme activity. To this end the initial construct was designed to contain an 806.077 antibody heavy chain Fd fragment linked at its C-terminus via a flexible (G$_4$S)$_3$ peptide linker to the N-terminus of the CPG2 polypeptide (as shown in FIG. 1 but substituting 806.077 in place of A5B7).

The antibody 806.077 (described in International Patent Application WO 97/42329, Zeneca Limited) binds with a very high degree of specificity to human CEA. Thus the 806.077 antibody is particularly suitable for targeting colorectal carcinoma or other CEA antigen bearing cells.

In general, antibody (or antibody fragment)-enzyme conjugate or fusion proteins should be at least divalent, that is to say capable of binding at least 2 tumour associated antigens (which may be the same or different). In the case of the (806.077 Fab-CPG2)$_2$ fusion protein, dimerisation of the enzyme component takes place (after expression, as with the native enzyme) thus forming an enzymatic molecule which contains two Fab antibody fragments (and is thus bivalent with respect to antibody binding sites) and two molecules of CPG2 (FIG. 2a).

a) Cloning of the 806.077 Antibody Genes

Methods for the cloning and characterisation of recombinant murine 806.077 F(ab')$_2$ antibody have been published (International Patent Application WO 97/42329, Example 7). Reference Example 7.5, describes cloning of the 806.077 antibody variable region genes into Bluescript™ KS+ vectors. These vectors were subsequently used as the source of the 806.077 variable region genes for the construction of 806.077 chimaeric light and heavy chain Fd genes.

b) Chimaeric 806.077 Antibody Vector Constructs

International Patent Application WO 97/42329, Example 8 describes the cloning of the 806.077 chimaeric light and heavy chain Fd genes in the vectors pNG3-Vkss-HuCk-NEO (NCIMB deposit no. 40799) and pNG4-VHss-HuIgG2CH1' (NCIMB deposit no. 40797) respectively. The resulting vectors were designated pNG4/VHss806.077VH-IgG2CH1' (806.077 chimaeric heavy chain Fd') and pNG3/ VKss806.077VK-HuCK-NEO (806.077 chimaeric light chain). These vectors were the source of the 806.077 antibody genes for the construction of the 806.077 Fab-CPG2 fusion protein.

c) Construction of the 806.077 Heavy Chain Fd-CPG2 Fusion Protein Gene

The cloning and construction of the CPG2 gene used are described in Example 1, sections c and d. Similarly, the construction of the pNG4/A5B7VH-IgG2CH1/CPG2 R6 vector, which was used for the constuction of the 806.077 heavy chain Fd-CPG2, is described in Example 1, section e. The 806.077 variable heavy chain gene was removed from the pNG4 Hss806.077VH-IgG2CH1' vector by digestion with restriction enzymes HindIII and NheI and a band of the expected size (approximately 300 b.p) which contained the variable region gene was purified. The same restriction enzymes (HindII/NheI) were used to digest the vector pNG4/A5B7VH-IgG2CHI/CPG2 R6 in preparation for the substitution of the 806.077 variable region for that of the A5B7 antibody. After digestion, the DNA was dephosphorylated then the larger vector band was separated and purified. The similarly restricted variable region gene fragment was then ligated in to this prepared vector and the ligation mix transformed into *E. coli*. DNA was prepared from the clones obtained and analysed by restriction digest analysis and subsequently sequenced to confirm the fusion gene sequence. A number of the clones were found to be correct and one of these clones, pNG4/VHss806VH-IgG2CH1/CPG2 R6, was chosen for further work. The sequence of the 806.077 heavy chain Fd-CPG2 fusion protein gene created is shown SEQ ID NOS 25 and 26.

d) Co-transfection, Transient Expression and Analysis of Fusion Protein

The plasmids pNG4/VHss806.077VH-IgG2CH1/CPG2 R6 (encoding the antibody chimaeric Fd-CPG2 fusion protein) and pNG3/VHss806.077VK-HuCK-NEO (encoding the antibody chimaeric light chain) were co-transfected into COS-7 cells using a LIPOFECTIN™ based procedure described in Example 1f above. Analysis of the fusion protein was performed as described in Example 1g. The HPLC based enzyme activity assay clearly showed CPG2 enzyme activity to be present in the cell supernatant and both the anti-CEA ELISA assays exhibited binding of protein at levels commensurate with a bivalent 806.077 antibody molecule. The fact that the anti-CEA ELISA detected with an anti-CPG2 reporter antibody also exhibited clear CEA binding indicated that not only antibody but also antibody-CPG2 fusion protein was binding CEA. Western blot analysis with both reporter antibody assays clearly displayed a (806.077 Fab-CPG2)$_2$ fusion protein subunit of the expected approximately 90 kDa size with only a small amount of degradation or smaller products (such as Fab or enzyme) observable. Since CPG2 is only known to exhibit enzyme activity when it is in a dimeric state it and since only antibody enzyme fusion protein is present, this indicates that the 90 kDa fusion protein (seen under SDS/PAGE conditions) dimerises via the natural CPG2 dimerisation mechanism to form a 180 kDa dimeric antibody-enzyme fusion protein molecule (FIG. 2a) in "native" buffer conditions. Furthermore, this molecule exhibits both CPG2 enzymatic activity and CEA antigen binding properties which do not appear to be significantly different in the fusion protein compared with enzyme or antibody alone.

e) Construction of a (806.077 Fab-CPG2)$_2$ Fusion Protein Coexpression Vector for Use in Transient and Stable Cell Line Expression For a simpler transfection methodology and the direct coupling of both expression cassettes to a single selection marker, a co-expression vector for fusion protein expression was constructed using the existing vectors pNG4/VHss806.077VH-IgG2CH1/CPG2 (encoding the antibody Fd-CPG2 fusion protein) and pNG3/VKss806.077VK-HuCK-NEO (encoding the antibody light chain). The pNG4/VHss806.077VH-IgG2CH1/CPG2 plasmid was first digested with the restriction enzyme ScaI, the linear vector band purified, digested with the restriction enzymes BglII and BamHI and a desired band (approximately 2700 b.p.) purified. The plasmid pNG3/VKss806.077VK-HuCK-NEO was digested with the restriction enzyme BamHI after which the DNA was dephosphorylated and the vector band purified. The heavy chain expression cassette fragment was ligated in to the prepared vector and the ligation mix transformed into *E. coli*. The orientation was checked by a variety of restriction digests and clones selected which had the heavy chain cassette in the same direction as that of the light chain. This plasmid was termed pNG3-806.077-CPG2/R6-coexp.-NEO.

EXAMPLE 14

Construction of a (55.1 scFv-CPG2)$_2$ Fusion Protein

The 55.1 antibody, described in the U.S. Pat. No. 5,665,357, recognises the CA55.1 tumour associated antigen which is expressed on the majority of colorectal tumours and is only weakly expressed or absent in normal colonic tissue. The determination of the 55.1 heavy and light chain cDNA sequences is described in Example 3 of the aforementioned U.S. patent. A plasmid expression vector allowing the secretion of antibody fragments into the periplasm of *E.coli* utilizing a single pelB leader sequence (pICI266) has been deposited as accession number NCIMB 40589 on Oct. 11, 1993 under the Budapest Treaty at the National Collections of Industrial and Marine Bacteria Limited (NCIMB), 23 St. Machar Drive, Aberdeen, AB2 1RY, Scotland, U.K. This vector was modified as described in Example 3.3a of U.S. Pat. No. 5,665,357 to create pICI1646; this plasmid was used for cloning of various 55.1 antibody fragments as described in further subsections of Example 3, including the production of a 55.1 scFv construct which was designated pICI1657.

The pICI1657 (otherwise known as pICI-55.1 scfv) was used as the starting point for the construction of the (55.1 scFv-CPG2)$_2$ fusion protein. The 55.1 scFv gene was amplified using the oligonucleotides CME 3270 and CME 3272 (SEQ ID NOS: 27 and 28 respectively) and the plasmid pICI1657 as the template DNA. The resulting PCR product band of about 790 b.p. was purified. Similarly the pNG4/A5B7VH-IgG2CH1/CPG2 R6 plasmid described in Example 1e above was used as the template DNA in a standard PCR reaction to amplify the CPG2 gene using the oligonucleotide primers CME 3274 and CME 3275 (SEQ ID NOS: 29 and 30 respectively). The expected PCR product band of about 1200 b.p. was purified.

A further PCR reaction was performed to join (or splice) the two purified PCR reaction products together. Standard PCR reaction conditions were used using varying amounts (between 0.5 to 2 µl) of each PCR product but utilising 25 cycles (instead of the usual 15 cycles) with the oligonucleotides CME 3270 and CME 3275 (SEQ ID NOS: 27 & 30). A reaction product of the expected size (approximately 2000 b.p.) was excised, purified and eluted in 20 µl H$_2$O, digested using the restriction enzyme EcoRI and purified. The vector pNG4/VHss806.077VH-IgG2CH1/CPG2 was prepared to receive the above PCR product by digestion with restriction enzyme EcoRI, dephosphorylated, the larger vector band separated from the smaller fragment and purified. The similarly restricted PCR product was ligated in to the prepared vector and the ligation mix transformed into *E. coli*. DNA was prepared from the clones obtained and analysed by HindIII/NotI restriction digestion to check for correct fragment orientation and appropriate clones subsequently sequenced to confirm the fusion gene sequence. A number of the clones with the correct sequence were obtained and one of these clones was given the plasmid designation pNG4/55.1scFv/CPG2 R6. The DNA and amino acid sequences of the fusion protein are shown in SEQ ID NOS: 31 and 32.

EXAMPLE 15

Modification of the Plasmid pNG4/55.1scFv/CPG2 R6 to Facilitate scFv Gene Exchange During the construction of pNG4/55.1scFv/CPG2 R6 a unique BspEI (isoschizomer of AccIII) was introduced into the flexible (G₄S)₃ linker coding sequence, situated between the antibody and CPG2 genes. To facilitate cloning of alternative scFv constructs the EcoRI site 3' of the CPG2 gene in the pNG4/55.1scFv/CPG2 R6 was deleted in order to enable insertion of alternative scFv antibody genes in frame, both behind the plasmid signal sequence and 5' of the CPG2 gene, via a EcoRI/BspEI fragment cloning. This modification was achieved by PCR mutagenesis in which first the pNG4/55.1scFv/CPG2 R6 was amplified using oligonucleotides CME 3903 and CME 3906 (SEQ ID NOS: 33 and 34 respectively). Secondly, the pNG4/55.1scFv/CPG2 R6 was again amplified but using oligonucleotides CME 4040 and CME 3905 (SEQ ID NOS: 35 and 36 respectively). The first expected PCR product band of about 420 b.p. was purified. The second PCR reaction was similarly treated and the expected PCR product band of about 450 b.p. purified.

A further PCR reaction was performed to join (or splice) the two purified PCR reaction products together. Standard PCR reaction conditions were used using varying amounts (between 0.5 to 2 µl) of each PCR product but utilising between 15 and 25 cycles with oligonucleotides CME 3905 and CME 3906 (SEQ ID NOS: 36 & 34). A reaction product of the expected size (approximately 840 b.p.) was purified, digested using the restriction enzymes NotI and XbaI and the expected fragment band of ca.460 b.p. was purified. The original pNG4/55.1scFv/CPG2 R6 was prepared to receive the above PCR product by digestion with restriction enzymes NotI and XbaI, dephosphorylated and the larger vector band separated from the smaller fragment. The vector band was purified and subsequently the similarly restricted PCR product was ligated in to the prepared vector and the ligation mix transformed into E. coli. DNA was prepared from the clones obtained and analysed by EcoRI restriction digestion to check for insertion of the modified fragment and appropriate clones subsequently sequenced to confirm the sequence change. A number of clones with the correct sequence were obtained and one of these clones was given the plasmid designation pNG4/55.1scFv/CPG2 R6/del EcoRI. This mutation removes the EcoRI site which was 3' of the CPG2 gene and simultaneously introduces an additional stop codon. The DNA sequence of the fusion protein gene up to, and including the two stop codons, are shown in SEQ ID NO: 37.

EXAMPLE 16
Construction of an 806.077 scFv Antibody Gene

The 806.077 scFv was created using vectors pNG4/VHss806.077VH-IgG2CH1' and pNG3/VKss806.077VK-HuCK-NEO which are sources for 806.077 VH and VK variable region genes. The 806.077 VH gene was amplified from the pNG4/VHss806.077VH-IgG2CH1' plasmid using standard PCR conditions with the oligonucleotides CME 3260 and CME 3266 (SEQ ID NOS: 39 and 40 respectively). The 806.077 VK was amplified from the pNG3/VKss806.077VK-HuCK-NEO plasmid using oligonucleotides CME 3262 and CME 3267 (SEQ ID NOS: 41 and 42 respectively). The VH and VK PCR reaction products were purified.

A further PCR reaction was performed to join (or splice) the two purified PCR reaction products together. Standard PCR reaction conditions were used using varying amounts (between 0.5 to 2 µl) of each PCR product but utilising between 15 and 25 cycles with the flanking oligonucleotides oligonucleotides CME 3260 and CME 3262 (SEQ ID NOS: 39 & 41). A reaction product of the expected size (approximately 730 b.p.) was purified, digested using the restriction enzymes NcoI and XhoI and an expected fragment band of about 720 b.p. purified.

The pICI1657 plasmid (otherwise known as pICI-55.1 scFv) had been further modified by the insertion of a double stranded DNA cassette produced from the two oligonucleotides CME 3143 and CME 3145 (SEQ ID NOS: 45 and 46) between the existing XhoI and EcoR restriction sites by standard cloning techniques to create the vector pICI266-55.1 scFv tag/his (the DNA sequence of the resulting 55.1 scFv tag/his gene is shown in SEQ ID NO: 47). This vector was prepared to receive the above PCR product by digestion with restriction enzymes NcoI and XhoI, dephosphorylated and the larger vector band separated from the smaller fragment. The vector band was purified and subsequently the similarly restricted PCR product was ligated in to the prepared vector and the ligation mix transformed into E. coli. DNA was prepared from the clones obtained and analysed by EcoRI restriction digestion to check for insertion of the modified fragment and appropriate clones subsequently sequenced to confirm the sequence change. A number of the clones with the correct sequence were obtained and one of these clones was given the plasmid designation pICI266/806IscFvtag/his (alternatively known as pICI266-806VH/VLscFvtag/his). The DNA and protein sequences of the 806I scFvtag/his gene are shown in (SEQ ID NOS: 25 and 26).

EXAMPLE 17
Construction of an (806.077 scFv-CPG2)₂ Fusion Protein

The pICI266/806IscFvtag/his plasmid was used as the source for the 806scFv. The gene was amplified using oligonucleotides CME 3907 and CME 3908 (SEQ ID NOS: 48 and 49) and a band of the expected size purified. This fragment was then digested using the restriction enzymes EcoRI and BspEI after which an expected fragment band of about 760 b.p. was purified.

The pNG4/55.1scFv/CPG2 R6/del EcoRI plasmid was prepared to receive the above fragment by digestion with restriction enzymes EcoRI and BspEI, dephosphorylated and the larger vector band separated from the smaller fragment. The vector band was purified and subsequently the similarly restricted fragment ligated in to the prepared vector and the ligation mix was transformed into E. coli. DNA was prepared from the clones obtained and analysed by EcoRI restriction digestion to check for insertion of the modified fragment. Appropriate clones were subsequently sequenced to confirm the gene sequence. A number of the clones with the correct sequence were obtained and one of these clones was given the plasmid designation pNG4/806IscFv/CPG2 R6/del EcoRI. The DNA and protein sequence of the fusion protein gene 806IscFv/CPG2 R6 are shown in (SEQ ID NOS: 50 and 51).

EXAMPLE 18
Co-transfection, Transient Expression of Antibody-CPG2 Fusion Proteins As described in Example 1f, plasmids encoding other fusion protein variants can be transfected using the given standard conditions in order to obtain transient expression of their encoded fusion protein from COS7 cells. In the case of(Fab-CPG2)₂ fusion proteins both co-transfection of appropriate plasmids or transfection of co-expression proteins can be performed. Similarly, the single expression plasmids of (scFv-CPG2)₂ fusion proteins can be also be transfected by the same protocol. In each case a maximum total of 4 mg DNA are used in an individual transfection.

EXAMPLE 19
Gene Switches for Protein Expression

As described in Example 1j, the use of tightly controlled but inducible gene switch systems such as the "TET on" or "TET off" (Grossen, M. et al (1995) Science 268: 1766–1769) or the ecdysone/muristerone A (No, D. et al (1996) PNAS 93 :3346–3351) may be used for the expression of fusion proteins. Appropriate methodology and cloning strategies as described in Example 5 may be used for antibody Fab-enzyme fusions requiring an IRES sequence for expression. Insertion of the appropriate gene cassette in to the switchable expression vectors may be used if the fusion protein product is a single polypeptide chain such as in scFv-enzyme constructs.

EXAMPLE 20
Determination of the Properties of COS7 Cell Secreted Antibody-enzyme Fusion Proteins The COS7 cell supernatant material can be analysed for the presence of antibody fusion proteins as described in Example 1g. Similarly the use of expressed fusion protein and CPG2 prodrug in an in vitro cytotoxicity assay can be performed as previously described in Example 1h. The HPLC based enzyme activity assay can show CPG2 enzyme activity to be present in the cell supernatant and anti-CEA ELISA can be detected with an anti-CPG2 reporter antibody to confirm binding of protein at levels commensurate with a bivalent A5B7 antibody molecule and also to demonstrate that antibody-CPG2 fusion protein (not only just the antibody component) is binding CEA.

Western blot analysis with both reporter antibody assays clearly display a fusion protein subunit of the expected size. Since CPG2 is only known to exhibit enzyme activity when it is in a dimeric state it and since only antibody enzyme fusion protein is present, this indicates that the fusion protein (seen under SDS/PAGE conditions) dimerises via the natural CPG2 dimerisation mechanism to form a dimeric antibody-enzyme fusion protein molecule in "native" buffer conditions. Furthermore, this molecule exhibits both CPG2 enzymatic activity and CEA antigen binding properties which do not appear to be significantly different in the fusion protein compared with enzyme or antibody alone. Results obtained from the cytotoxicity assay can demonstrate that antibody-enzyme fusion protein (together with prodrug) causes at least equivalent cell kill and resulted in lower numbers of cells at the end of the assay period than the equivalent levels of A5B7 F(ab')$_2$-CPG2 conjugate (with the same prodrug). Since cell killing (above basal control levels) can only occur if the prodrug is converted to active drug by the CPG2 enzyme (and since the cells are washed to remove unbound protein, only cell bound enzyme will remain at the stage where the prodrug is added). Thus this experiment can demonstrate that at least as much of the (A5B7-CPG2 R6)$_2$ fusion protein remains bound compared with conventional A5B7 F(ab)$_2$-CPG2 conjugate as a greater degree of cell killing (presumably due to higher prodrug to drug conversion) occurs.

EXAMPLE 21
In vitro and in vivo Determination of the Properies of Antibody-enzyme Fusion Proteins Expressed from Recombinant Tumour Cells The construction of fusion protein expressing tumour cell lines can be performed as described in Example 4.

Retention of the fusion protein on the cell surface of recombinant LoVo tumour cells expressing antibody-enzyme fusion protein can be shown using the techniques described in Example 7. Selective killing of cultured LoVo tumour cells transfected with an antibody-CPG2 fusion protein gene by a prodrug that is converted by the enzvme into an active drug can be demonstrated as described in Example 8. Establishment of antibody-enzyme fusion protein expressing LoVo tumours xenografts in athymic mice can be performed as described in Example 9. Determination of enzyme activity in tumour xenograft samples can also be determined as described in Example 10.

Determination enzyme activity in plasma samples performed as described in Example 11. The anti-tumour activity of PGP prodrug in LoVo tumours expressing the antibody-CPG2 fusion protein can be evaluated using the method described in Example 12.

The results from these experiments can be used to show that the antibody-CPG2 fusion protein secreted from CEA positive tumour cell lines bind to the surface of the cells (via CEA) whereas the same protein expressed from CEA negative tumours shows no such binding. These results can demonstrate that the transfected cells which express the antibody-CPG2 fusion protein can convert the PGP prodrug into the more potent active drug while non-transfected LoVo cells are unable to convert the prodrug. Consequently the transfected LoVo cells will be over 100 fold more sensitive to the PGP prodrug in terms of cell killing compared to the non-transfected LoVo cells, thus demonstrating that transfecting tumour cells with a gene for an antibody-enzyme fusion protein can lead to selective tumour cell killing with a prodrug.

Administration of PGP to LoVo tumours established from recombinant LoVo cells or recombinant Lovo/Parental LoVo cell mixes can result in a significant anti-tumour effect as judged by the PGP treated tumours decreasing in size compared to the formulation buffer only treated tumours and it taking a significantly longer time for the PGP treated tumours to reach 4 times their initial tumour volume compared with formulation buffer treated tumours. In contrast, administration of PGP to LoVo tumours established from non-transfected cells would result in no significant anti-tumour activity.

Similar studies can be used to demonstrate that the antibody-enzyme gene delivered in an appropriate gene delivery vector to established LoVo tumours produced from non-transfected parental LoVo cells when used in combination with the PGP prodrug can result in significant anti-tumour activity. Thus non-transfected LoVo cells are injected into athymic nude mice ($1 \times 10^7$ tumour cells per mouse) and once the tumours are 5–7 mm in diameter the vector containing the antibody-enzyme fusion protein gene is injected intra-tumourally. After 1–7 days to allow the antibody-enzyme fusion protein to be expressed by, and bind to, the LoVo tumour cells, the PGP prodrug is administered as previously described. This results in significant anti-tumour activity compared with control mice receiving formulation buffer instead of PGP prodrug.

EXAMPLE 22
Preparation of (Murine A5B7 Fab-CPG2)$_2$ Fusion Protein (Murine A5B7 Fab-CPG2)$_2$ is expressed from COS-7 and CHO cells essentially as described in part (d) of Example 48 of International Patent Application WO 97/42329 (Zeneca Limited, published Nov. 13, 1997) by cloning the genes for A5B7 light chain and A5B7 Fd linked at its C-terminus via a flexible (G$_4$S)$_3$ peptide linker to CPG2 in the pEE14 co-expression vector.

The murine A5B7 light chain is isolated from pAF8 (described in part g of Reference Example 5 in International Patent Application WO 96/20011, Zeneca Limited ). Plasmid pAF8 is cut with EcoRI and the resulting 732 bp fragment isolated by electrophoresis on a 1% agarose gel. This fragment is cloned into pEE14 (described by Bebbington in METHODS: A Companion to Methods in Enzymology (1991) 2, 136–145) similarly cut with EcoRI and the resulting plasmid used to transform *E. coli* strain DH5α. The transformed cells are plated onto L agar plus ampicillin (100 μg/ml). A clone containing a plasmid with the correct sequence and orientation is confirmed by DNA sequence analysis (SEQ ID NO: 57) and the plasmid named pEE14/ASB7muVkmuCK. The amino acid sequence of the encoded signal sequence (amino acid residues 1 to 22) and murine light chain (amino acid residues 23 to 235) is shown in SEQ ID NO: 58.

The murine Fd-CPG2 gene is prepared from the R6 variant of the CPG2 gene (d of Example 1) and the murine A5B7 Fd sequence in pAF1 (described in part d of Reference Example 5 in International Patent Application WO 96/20011, Zeneca Limited ). A PCR reaction with oligonucleotides SEQ ID NOS: 53 and 54 on pAF1 gives a 247 bp fragment. This is cut with HindIII and BamHI and cloned into similarly cut pUC19. The resulting plasmid is used to transform *E. coli* strain DH5a. The transformed cells are plated onto L agar plus ampicillin (100 μg/ml). A clone containing a plasmid with the correct sequence is named pUC19/muCH1/NcoI-AccIII(Fd). A second PCR with oligonucleotides SEQ ID NOS: 55 and 56 on pNG/VKss/CPG2/R6-neo (Example 1) gives a 265 bp fragment which is cut with HindIII and EcoRI and cloned into similarly cut pUC19 as above to give plasmid pUC19/muCH1-linker-CPG2/AccIII-SacII. Plasmid pUC19/muCH1/NcoI-AccIII (Fd) is cut with HindIII and AccIII and the 258 bp fragment isolated by electrophoresis on a 1% agarose gel. This fragment is cloned into HindIII and AccII cut pUC19/muCH1-linker-CPG2/AccIII-SacII to give plasmid pUC19/muCH1-linker-CPG2/NcoI-SacII. A 956 bp fragment is isolated from pNG/VKss/CPG2/R6-neo by cutting it with SacII and EcoRI. This is cloned into SacII and EcoRI cut pUC19/muCH1-linker-CPG2/NcoI-SacII to give plasmid pUC19/muCH1-linker-RC/CPG2(R6). The complete gene construct is prepared by isolating a 498 bp HindIII to NcoI fragment from pAF1 and cloning it into HindIII and NcoI cut pUC19/muCH1-linker-RC/CPG2(R6). The resulting plasmid is used to transform DH5α. The transformed cells are plated onto L agar plus ampicillin (100 μg/ml). A clone containing a plasmid with the correct sequence and orientation is confirmed by DNA sequence analysis (SEQ ID NO: 59) and the plasmid named pUC19/muA5B7-RC/CPG2 (R6). The amino acid sequence of the encoded signal sequence (amino acid residues 1 to 19) and murine Fd-linker-CPG2 (amino acid residues 20 to 647) is shown in SEQ ID NO: 60. Alternatively, the CPG2 gene sequence described in Example 1 can be obtained by total gene synthesis and converted to the R6 variant as described in d of Example 1. In this case, the base residue C at position 933 in SEQ ID NO: 59 is changed to G. The amino acid sequence of SEQ ID NO: 60 remains unaltered.

For expression in the pEE14 vector, the gene is first cloned into pEE6 (this is a derivative of pEE6.hCMV—Stephens and Cockett, 1989, Nucleic Acids Research 17, 7110, in which a HindIII site upstream of the hCMV promoter has been converted to a BglII site). Plasmid pUC19/muA5B7-RC/CPG2(R6) is cut with HindIII and EcoRI and the 1974 bp fragment isolated by electrophoresis on a 1% agarose gel. This is cloned into HindIII and EcoRI cut pEE6 in *E. coli* strain DH5α to give plasmid pEE6/muA5B7-RC/CPG2(R6). The pEE14 co-expression vector is made by first cutting pEE6/muA5B7-RC/CPG2(R6) with BglII and BamHI and isolating the 4320 bp fragment on a 1% agarose gel. This fragment is cloned into BglII and BamHI cut pEE14/A5B7muVkmuCK. The resulting plasmid is used to transform *E. coli* strain DH5α. The transformed cells are plated onto L agar plus ampicillin (100 μg/ml). A clone containing a plasmid with the correct sequence and orientation is confirmed by DNA sequence analysis and the plasmid named pEE14/muA5B7-RC/CPG2 (R6).

For expression of (murine A5B7 Fab-CPG2)$_2$, plasmid pEE14/muA5B7-RC/CPG2(R6) is used to transfect COS-7 or CHO cells as described in Example 48 of International Patent Application WO 97/42329, Zeneca Limited, published Nov. 13, 1997. COS cell supernatants and CHO clone supernatants are assayed for activity as described in Example 1 and shown to have CEA binding and CPG2 enzyme activity.

EXAMPLE 23

Pharmaceutical Composition

The following illustrate a representative pharmaceutical dosage form containing a gene construct of the invention which may be used for therapy in combination with a suitable prodrug.

A sterile aqueous solution, for injection either parenterally or directly into tumour tissue, containing $10^7$–$10^{11}$ adenovirus particles comprising a gene construct as described in Example 1. After 3–7 days, three 1 g doses of prodrug are administered as sterile solutions at hourly intervals. Prodrug is selected from N-(4-[N,N-bis(2-iodoethyl)amino]-phenoxycarbonyl)-L-glutamic acid, N-(4-[N,N-bis(2-chloroethyl)amino]-phenoxycarbonyl)-L-glutamic-gamma-(3,5-dicarboxy)anilide or N-(4-[N,N-bis(2-chloroethyl)amino]-phenoxycarbonyl)-L-glutamic acid or a pharmaceutically acceptable salt thereof.

What is claimed is:

1. A matched two component system designed for use in a mammalian host in which the components comprise:
   (i) a first component that comprises a gene construct encoding a cell targeting moiety and a heterologous prodrug activating enzyme and a secretory leader sequence for use as a medicament in a mammalian host wherein the gene construct is capable of expressing the cell targeting moiety and heterologous prodrug activating enzyme and the secretory leader sequence as a conjugate within a cell in the mammalian host and wherein the conjugate is directed by the secretory leader sequence to leave the cell thereafter for selective localisation at a cell surface antigen recognised by the cell targeting moiety; and
   (ii) a second component that comprises a prodrug which can be converted into a cytotoxic drug by the heterologous enzyme encoded by the first component.

2. The matched two component system according to claim 1 in which the heterologous prodrug activating enzyme is a heterologous enzyme CPG2; and the second component prodrug is selected from N-(4-[N,N-bis(2-iodoethyl)amino]-phenoxycarbonyl)-L-glutamic acid, N-(4-[N,N-bis(2-chloroethyl)amino]-phenoxycarbonyl)-L-glutamic-gamma-(3,5-dicarboxy)anilide or N-(4-[N,N-bis(2-chloroethyl)amino]-phenoxycarbonyl)-L-glutamic acid or a pharmaceutically acceptable salt thereof.

3. The matched two component system according to claim 1 wherein the cell targeting moiety is selectively localised to a cell surface antigen, and the cell surface antigen is specific for at least one human solid tumor.

4. The matched two component system according to claim 1 wherein the cell targeting moiety is an antibody or fragment thereof.

5. The matched two component system according to claim 4 wherein the cell targeting moiety is an anti-CEA antibody selected from antibody A5B7 or 806.077 antibody.

6. The matched two component system according to claim 1 wherein the heterologous prodrug activating enzyme has mutated glycosylation sites.

7. The matched two component system according to claim 1 wherein the heterologous prodrug activating enzyme is a carboxypeptidase.

8. The matched two component system according to claim 1 wherein the heterologous prodrug activating enzyme is a heterologous enzyme CPG2.

9. The matched two component system according to claim 8 in which the conjugate is a fusion protein in which the enzyme is fused to the C terminus of an antibody through the heavy or light chain thereof whereby dimerisation of the encoded conjugate when expressed can take place through a dimerisation domain on CPG2.

10. The matched two component system according to claim 9 wherein the fusion protein is formed through linking a C-terminus of an antibody Fab heavy chain to an N-terminus of a CPG2 molecule to form a Fab-CPG2 whereby two Fab-CPG2 molecules when expressed dimerise through CPG2 to form a (Fab-CPG2)$_2$ conjugate.

11. The matched two component system according to claim 1 wherein the heterologous prodrug activating enzyme is a carboxypeptidase mutant selected from the group consisting of [D253K]HCPB, [G251T,D253K]HCPB, and [A248S,G251T,D253K]HCPB.

12. The matched two component system according to claim 1 wherein the gene construct comprises a transcriptional regulatory sequence comprising a promoter and a control element which comprises a genetic switch to control expression of the gene construct.

13. The matched two component system according to claim 12 wherein the transcriptional regulatory sequence comprises a genetic switch control element regulated by presence of tetracycline or ecdysone.

14. The matched two component system according to claim 12 wherein the promoter is dependent on cell type and is selected from the group consisting of promoters of genes encoding carcinoembryonic antigen (CEA), alpha-foetoprotein (AFP), tyrosine hydroxylase, choline acetyl transferase, neurone specific enolase, insulin, glial fibro acidic protein, HER-2/neu, c-erbB2, and N-myc.

15. The matched two component system according to claim 1 wherein the gene construct is packaged within an adenovirus.

16. A method for making the two component system according to claim 1 which comprises inserting genes encoding the cell targeting moiety, the heterologous prodrug activating enzyme, and the secretory leader sequence into a vector.

17. A method for the delivery of a cytotoxic drug to a site which comprises administering to a mammalian host the first component and the second component of the matched two component system according to claim 15 to the mammalian host; wherein a prodrug of the second component can be converted into a cytotoxic drug in the mammalian host by the heterologous enzyme encoded by the first component.

18. The method according to claim 17 in which the heterologous prodrug activating enzyme is a heterologous enzyme CPG2; and the second component prodrug is selected from N-(4-[N,N-bis(2-iodoethyl)amino]-phenoxycarbonyl)-L-glutamic acid, N-(4-[N,N-bis(2-chloroethyl)amino]-phenoxycarbonyl)-L-glutamic-gamma-(3,5-dicarboxy)anilide or N-(4-[N,N-bis(2-chloroethyl)amino]-phenoxycarbonyl)-L-glutamic acid or a pharmaceutically acceptable salt thereof.

19. The method according to claim 17 wherein the cell targeting moiety is selectively localised to a cell surface antigen, and the cell surface antigen is specific for at least one human solid tumor.

20. The method according to claim 17 wherein the cell targeting moiety is an antibody or fragment thereof.

21. The method according to claim 20 wherein the cell targeting moiety is an anti-CEA antibody selected from antibody A5B7 or 806.077 antibody.

22. The method according to claim 17 wherein the heterologous prodrug activating enzyme has mutated glycosylation sites.

23. The method according to claim 17 wherein the heterologous prodrug activating enzyme is a carboxypeptidase.

24. The method according to claim 17 wherein the heterologous prodrug activating enzyme is a heterologous enzyme CPG2.

25. The method according to claim 24 in which the antibody-enzyme CPG2 conjugate is a fusion protein in which the enzyme is fused to the C terminus of the antibody through the heavy or light chain thereof whereby dimerisation of the encoded conjugate when expressed can take place through a dimerisation domain on CPG2.

26. The method according to claim 25 wherein the fusion protein is formed through linking a C-terminus of an antibody Fab heavy chain to an N-terminus of a CPG2 molecule to form a Fab-CPG2 whereby two Fab-CPG2 molecules when expressed dimerise through CPG2 to form a (Fab-CPG2)$_2$ conjugate.

27. The method according to claim 17 wherein the heterologous prodrug activating enzyme is a carboxypeptidase mutant selected from the group consisting of [D253K] HCPB, [G251T,D253K]HCPB, and [A248S,G251T, D253K] HCPB.

28. The method according to claim 17 wherein the gene construct comprises a transcriptional regulatory sequence comprising a promoter and a control element which comprises a genetic switch to control expression of the gene construct.

29. The method according to claim 28 wherein the transcriptional regulatory sequence comprises a genetic switch control element regulated by presence of tetracycline or ecdysone.

30. The method according to claim 28 wherein the promoter is dependent on cell type and is selected from the group consisting of promoters of genes encoding carcinoembryonic antigen (CEA), alpha-foetoprotein (AFP), tyrosine hydroxylase, choline acetyl transferase, neurone specific enolase, insulin, glial fibro acidic protein, HER-2/neu, c-erbB2, and N-myc.

31. The method according to claim 17 wherein the gene construct is packaged within an adenovirus.

32. A matched two component system comprising:
   (i) a first component that comprises a gene construct encoding a cell targeting moiety, a heterologous prodrug activating enzyme, and a secretory leader sequence expressed as a conjugate; and
   (ii) a second component that comprises a prodrug which is converted into a cytotoxic drug by the conjugate.

33. The matched two component system according to claim 32 wherein the cell targeting moiety is an antibody or fragment thereof which is selectively localised to a cell surface antigen, and the cell surface antigen is specific for at least one human solid tumor.

34. A method for the delivery of a cytotoxic drug which comprises administering to a mammalian host: the first component and the second component of the matched two component system according to claim 32 to the mammalian host; wherein the prodrug of the second component is converted into a cytotoxic drug in the mammalian host by the heterologous enzyme encoded of the gene construct.

* * * * *